United States Patent
Andersson et al.

(10) Patent No.: US 8,501,784 B2
(45) Date of Patent: *Aug. 6, 2013

(54) 2-PYRIDONE DERIVATIVES AS NEUTROPHIL ELASTASE INHIBITORS AND THEIR USE

(75) Inventors: Marjana Andersson, Lund (SE); Peter Hansen, Lund (SE); Hans Lonn, Lund (SE); Antonios Nikitidis, Lund (SE); Petter Sjölin, Lund (SE)

(73) Assignee: Astrazeneca AB, Sodertalje (SE)

(*) Notice: Subject to any disclaimer, the term of this patent is extended or adjusted under 35 U.S.C. 154(b) by 0 days.

This patent is subject to a terminal disclaimer.

(21) Appl. No.: 13/273,860

(22) Filed: Oct. 14, 2011

(65) Prior Publication Data

US 2012/0035157 A1 Feb. 9, 2012

Related U.S. Application Data

(63) Continuation of application No. 10/572,706, filed as application No. PCT/SE2004/001335 on Sep. 15, 2004, now Pat. No. 8,063,073.

(30) Foreign Application Priority Data

Sep. 18, 2003 (SE) ...................................... 0302486

(51) Int. Cl.
A61K 31/44 (2006.01)
C07D 401/02 (2006.01)

(52) U.S. Cl.
USPC ........................................ 514/333; 546/256

(58) Field of Classification Search
None
See application file for complete search history.

(56) References Cited

U.S. PATENT DOCUMENTS

| | | | |
|---|---|---|---|
| 4,181,658 A | 1/1980 | Hitzel et al. | |
| 4,186,200 A | 1/1980 | Kubo et al. | |
| 5,441,960 A | 8/1995 | Bernstein et al. | |
| 5,521,179 A | 5/1996 | Bernstein et al. | |
| 6,028,081 A | 2/2000 | Sada et al. | |
| 6,977,266 B2 | 12/2005 | Tada et al. | |
| 6,979,690 B2 | 12/2005 | Gymer et al. | |
| 8,063,073 B2 * | 11/2011 | Hansen et al. | 514/333 |
| 2004/0023973 A1 | 2/2004 | Nagato et al. | |
| 2004/0082619 A1 | 4/2004 | Tada et al. | |
| 2004/0235761 A1 | 11/2004 | Furuta et al. | |
| 2005/0101590 A1 | 5/2005 | Yasui et al. | |
| 2006/0035938 A1 | 2/2006 | Bladh et al. | |
| 2006/0052411 A1 | 3/2006 | Tada et al. | |
| 2006/0100249 A1 | 5/2006 | Smith | |
| 2006/0211695 A1 | 9/2006 | Borzilleri et al. | |
| 2006/0270666 A1 | 11/2006 | Bladh et al. | |
| 2007/0010551 A1 | 1/2007 | Bladh et al. | |
| 2007/0043036 A1 | 2/2007 | Hansen et al. | |
| 2007/0203129 A1 | 8/2007 | Andersson et al. | |
| 2007/0213323 A1 | 9/2007 | Imogai et al. | |
| 2009/0105239 A1 | 4/2009 | Brimert et al. | |
| 2009/0131483 A1 | 5/2009 | Hansen et al. | |
| 2009/0131486 A1 | 5/2009 | Hansen et al. | |
| 2009/0209555 A1 | 8/2009 | Hansen et al. | |
| 2010/0216843 A1 | 8/2010 | Briggner et al. | |
| 2010/0280048 A1 | 11/2010 | Ainge et al. | |
| 2011/0003858 A1 | 1/2011 | Bergstrom et al. | |

FOREIGN PATENT DOCUMENTS

| | | |
|---|---|---|
| EP | 0008864 A1 | 3/1980 |
| EP | 1300396 B1 | 4/2003 |
| EP | 1357111 B1 | 10/2003 |
| EP | 1465626 B1 | 9/2008 |
| GB | 2383326 A | 6/2003 |
| GB | 2392910 A | 3/2004 |
| JP | 02152966 A | 6/1990 |
| WO | 98/24780 A2 | 6/1998 |
| WO | 2001/096308 A1 | 12/2001 |
| WO | 2002/053543 A1 | 7/2002 |
| WO | 03/047577 A2 | 6/2003 |
| WO | WO 03/047577 A2 * | 6/2003 |
| WO | 03/070277 A1 | 8/2003 |
| WO | 2004/020410 A2 | 3/2004 |
| WO | 2004/043924 A1 | 5/2004 |
| WO | 2005/021509 A1 | 3/2005 |

(Continued)

OTHER PUBLICATIONS

Eistert B et al "Synthese und Reaktionen substituierter Pyrrolin-2,33-dione mit Diazoalkanene" Liebigs Ann. Chem (1976) pp. 1023-1030.

Wright J L et al "A neutrophil elastase inhibitor reduces cigarette smoke-induced remodelling of lung vessels" Eur Respi J (2003) vol. 22 pp. 77-81.

Bauer & Weber "Benzodiazepines with psychotropic activity V.1,5-Benzondiazepinetriones and their precursors" Justus Liebigs Annalen de Chemie 762: 73-82 (1972) as abstracted by CAS on STN (File CAPLUS, Accession No. 1973: 16148).

Beilstein Registry No. 7995731, Beilstein Institute for Organic Chemistry XP002481053 & Khim Geterotsikl Sodedin vol. 34 (1) : 73-76 (1998).

(Continued)

*Primary Examiner* — Zinna Northington Davis

(57) ABSTRACT

There are provided novel compounds of formula (I),

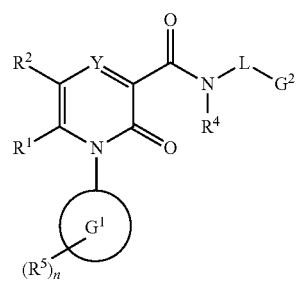

(I)

wherein $R^1$, $R^2$, $R^4$, $G^1$, $G^2$, L, Y and n are as defined in the Specification and optical isomers, racemates and tautomers thereof, and pharmaceutically acceptable salts thereof; together with processes for their preparation, compositions containing them and their use in therapy. The compounds are inhibitors of neutrophil elastase.

9 Claims, No Drawings

FOREIGN PATENT DOCUMENTS

| | | |
|---|---|---|
| WO | 2005/021512 A1 | 3/2005 |
| WO | 2005/026123 A1 | 3/2005 |
| WO | 2005/026124 A1 | 3/2005 |
| WO | 2005/080372 A1 | 9/2005 |
| WO | 2005/082864 A1 | 9/2005 |
| WO | 2006/030032 A1 | 3/2006 |
| WO | 2006/082412 A2 | 8/2006 |
| WO | 2006/098683 A1 | 9/2006 |
| WO | 2006/098684 A1 | 9/2006 |
| WO | 2006/116713 A1 | 11/2006 |
| WO | 2006/136857 A1 | 12/2006 |
| WO | 2007/107706 A2 | 9/2007 |
| WO | 2007/129060 A1 | 11/2007 |
| WO | 2007/129962 A1 | 11/2007 |
| WO | 2007/129963 A1 | 11/2007 |
| WO | 2008/003158 A1 | 1/2008 |
| WO | 2008/104752 A1 | 9/2008 |
| WO | 2009/058076 A1 | 5/2009 |
| WO | 2009/061271 A1 | 5/2009 |
| WO | 2010/094964 A1 | 8/2010 |

OTHER PUBLICATIONS

Chughtai et al "Potential Role of Inhibitors of Neurophil Elastase in Treating Diseases of the Airway" Journal of Aerosol Medicine 17(4) 289-298 (2004).

Europ Resp Soc Feb. 13, 2007 http://www.newtocopd.com/currentaffairsnews/list 751_item17680.aspx,downloaded Jan. 16, 2008.

Friedman "Future Treatment Strategies for COPD" Clinical Cornerstone COPD, 5(1): 45-51 (2004).

Ohbayashi "Current synthetic inhibitors of human neutrophil elastase in 2005" Expert Opinion on Therapeutic Patents 15(7) 759-771 (2005).

Okayama et al "Clinical effects of a neutrophil elastase inhibitor, sivelestat in patients with acute respiratory distress syndrome" J Anesth 20:6-10 (2006).

Shimizu et al "A mechanism of antigen-induced mucus production in nasal epithelium of sensitized rats. A comparison with lipopolysaccaride-induced mucus production" Am J Respi Crit Care Med 161 1648-1654 (2000).

STN International file CAPLUS, CAPLUS Accession No. 1990:611864 Document No. 113:211864, Otsuka Pharmaceutical Co. Ltd "4-Hydroxycarbostyrils as anti-inflammatory and antiallergy agents" & JP A2 02152966 (1990).

STN International file CAPLUS, CAPLUS Accession No. 1995:456529 Document No. 123:198678 Ukrainets I.V et al "4-Hydroxy-2 quinolones. 23.N-(2-Thiazolyl)amides of 1-substitued 4-hydroxy-2-oxoquinoline-3-carboxyclic acids-a new group of potential anti-inflammatory drugs & Khimiya 2-oxoquinoline-3-carboxyclic acids—a new group of potential anti-inflammatory drugs" & Khimiya Geterotsiklicheskikh Soedinenii 10: 1397-1399 (1994).

Harayama et al "Hydrolysis product of flavins (isoalloxazines)"J Chem Soc Perkin Trans 75-83 (1987).

Ohbayashi "Neutrophil elastase inhibitors as treatment for COPD" Expert Opin Drugs 11(7)965-980 (2002).

Ohbayashi et al novel neutrophil elastase inhibitors as a treatment for neutrophil-predominant inflammatory lung disease 2idRUGS 5(9):910-923 (2002).

Sato et al "Neutrophil elastase and cancer" Surgical Oncology 15: 217-222(2006).

Ukrainets et al "4-Hydroxy-2-quinolones 23. N-(2-Thiazolyl)amides of 1-substitued 4-hydroxy-2-oxoquinoline-3-carboxylic acids-a new group of potential antiiflammatory drugs" Chemistry of Heterocyclic Compounds, A translation of Khimiya Geterotsiklicheskikh Soedinenii 30(10):1211-1213(1994).

U.S. Appl. No. 12/895,995, filed Oct. 1, 2010.

\* cited by examiner

2-PYRIDONE DERIVATIVES AS NEUTROPHIL ELASTASE INHIBITORS AND THEIR USE

CROSS-REFERENCE TO RELATED APPLICATIONS

This application is a continuation of U.S. patent application Ser. No. 10/572,706, filed Mar. 17, 2006, now U.S. Pat. No. 8,063,073, which is a national phase application under 35 U.S.C. §371 of International Application No. PCT/SE04/01335, filed Sep. 15, 2004, which claims the benefit of Swedish Patent App. No. 0302486-6, filed Sep. 18, 2003, all of which are incorporated herein by reference in their entireties.

FIELD OF THE INVENTION

This invention relates to novel 2-pyridone derivatives, processes for their preparation, pharmaceutical compositions comprising them, and their use in therapy.

BACKGROUND OF THE INVENTION

Elastases are possibly the most destructive enzymes in the body, having the ability to degrade virtually all connective tissue components. The uncontrolled proteolytic degradation by elastases has been implicated in a number of pathological conditions. Human neutrophil elastase (hNE), a member of the chymotrypsin superfamily of serine proteases is a 33-KDa enzyme stored in the azurophilic granules of the neutrophils. In neutrophils the concentration of NE exceeded 5 mM and its total cellular amount has been estimated to be up to 3 pg. Upon activation, NE is rapidly released from the granules into the extracellular space with some portion remaining bound to neutrophil plasma membrane (See Kawabat et al. 2002, Eur. J. Pharmacol. 451, 1-10). The main intracellular physiological function of NE is degradation of foreign organic molecules phagocytosed by neutrophils, whereas the main target for extracellular elastase is elastin (Janoff and Scherer, 1968, J. Exp. Med. 128, 1137-1155). NE is unique, as compared to other proteases (for example, proteinase 3) in that it has the ability to degrade almost all extracellular matrix and key plasma proteins (See Kawabat et al., 2002, Eur. J. Pharmacol. 451, 1-10). It degrades a wide range of extracellular matrix proteins such as elastin, Type 3 and type 4 collagens, laminin, fibronectin, cytokines, etc. (Ohbayashi, H., 2002, Expert Opin. Investig. Drugs, 11, 965-980). NE is a major common mediator of many pathological changes seen in chronic lung disease including epithelial damage (Stockley, R. A. 1994, Am. J. Resp. Crit. Care Med. 150, 109-113).

The destructive role of NE was solidified almost 40 years ago when Laurell and Eriksson reported an association of chronic airflow obstruction and emphysema with deficiency of serum $\alpha_1$-antitrypsin (Laurel and Eriksson, 1963, Scand. J. Clin. Invest. 15, 132-140). Subsequently it was determined that $\alpha_1$-antitrypsin is the most important endogenous inhibitor of human NE. The imbalance between human NE and endogenous antiprotease is believed to cause excess human NE in pulmonary tissues which is considered as a major pathogenic factor in chronic obstructive pulmonary disease (COPD). The excessive human NE shows a prominent destructive profile and actively takes part in destroying the normal pulmonary structures, followed by the irreversible enlargement of the respiratory airspaces, as seen mainly in emphysema. There is an increase in neutrophil recruitment into the lungs which is associated with increased lung elastase burden and emphysema in $\alpha_1$-proteinase inhibitor-deficient mice (Cavarra et al., 1996, Lab. Invest. 75, 273-280). Individuals with higher levels of the NE-$\alpha_1$ protease inhibitor complex in bronchoalveolar lavage fluid show significantly accelerated decline in lung functions compared to those with lower levels (Betsuyaku et al. 2000, Respiration, 67, 261-267). Instillation of human NE via the trachea in rats causes lung haemorrhage, neutrophil accumulation during acute phase and emphysematous changes during chronic phase (Karaki et al., 2002, Am. J. Resp. Crit. Care Med., 166, 496-500). Studies have shown that the acute phase of pulmonary emphysema and pulmonary haemorrhage caused by NE in hamsters can be inhibited by pre-treatment with inhibitors of NE (Fujie et al., 1999, Inflamm. Res. 48, 160-167).

Neutrophil-predominant airway inflammation and mucus obstruction of the airways are major pathologic features of COPD, including cystic fibrosis and chronic bronchitis. NE impairs mucin production, leading to mucus obstruction of the airways. NE is reported to increase the expression of major respiratory mucin gene, MUC5AC (Fischer, B. M. & Voynow, 2002, Am. J. Respir. Cell Biol., 26, 447-452). Aerosol administration of NE to guinea pigs produces extensive epithelial damage within 20 minutes of contact (Suzuki et al., 1996, Am. J. Resp. Crit. Care Med., 153, 1405-1411). Furthermore NE reduces the ciliary beat frequency of human respiratory epithelium in vitro (Smallman et al., 1984, Thorax, 39, 663-667) which is consistent with the reduced mucociliary clearance that is seen in COPD patients (Currie et al., 1984, Thorax, 42, 126-130). The instillation of NE into the airways leads to mucus gland hyperplasia in hamsters (Lucey et al., 1985, Am. Resp. Crit. Care Med., 132, 362-366). A role for NE is also implicated in mucus hypersecretion in asthma. In an allergen sensitised guinea pig acute asthma model an inhibitor of NE prevented goblet cell degranulation and mucus hypersecretion (Nadel et al., 1999, Eur. Resp. J., 13, 190-196).

NE has been also shown to play a role in the pathogenesis of pulmonary fibrosis. NE: $\alpha_1$-protenase inhibitor complex is increased in serum of patients with pulmonary fibrosis, which correlates with the clinical parameters in these patients (Yamanouchi et al., 1998, Eur. Resp. J. 11, 120-125). In a murine model of human pulmonary fibrosis, a NE inhibitor reduced bleomycin-induced pulmonary fibrosis (Taooka et al., 1997, Am. J. Resp. Crit. Care Med., 156, 260-265). Furthermore investigators have shown that NE deficient mice are resistant to bleomycin-induced pulmonary fibrosis (Dunsmore et al., 2001, Chest, 120, 35S-36S). Plasma NE level was found to be elevated in patients who progressed to ARDS implicating the importance of NE in early ARDS disease pathogenesis. (Donnelly et al., 1995, Am. J. Res. Crit. Care Med., 151, 4284433). The antiproteases and NE complexed with antiprotease are increased in lung cancer area (Marchandise et al., 1989, Eur. Resp. J. 2, 623-629). Recent studies have shown that polymorphism in the promoter region of the NE gene are associated with lung cancer development (Taniguchi et al., 2002, Clin. Cancer Res., 8, 1115-1120.

Acute lung injury caused by endotoxin in experimental animals is associated with elevated levels of NE (Kawabata, et al., 1999, Am. J. Resp. Crit. Care, 161, 2013-2018). Acute lung inflammation caused by intratracheal injection of lipopolysaccharide in mice has been shown to elevate the NE activity in bronchoalveolar lavage fluid which is significantly inhibited by a NE inhibitor (Fujie et al., 1999, Eur. J. Pharmacol., 374, 117-125; Yasui, et al., 1995, Eur. Resp. J., 8, 1293-1299). NE also plays an important role in the neutrophil-induced increase of pulmonary microvascular permeability observed in a model of acute lung injury caused by tumour necrosis factor $\alpha$ (TNF$\alpha$) and phorbol myristate acetate (PMA) in isolated perfused rabbit lungs (Miyazaki et al., 1998, Am. J. Respir. Crit. Care Med., 157, 89-94).

A role for NE has also been suggested in monocrotoline-induced pulmonary vascular wall thickening and cardiac hypertrophy (Molteni et al., 1989, Biochemical Pharmacol. 38, 2411-2419). Serine elastase inhibitor reverses the monocrotaline-induced pulmonary hypertension and remodelling in rat pulmonary arteries (Cowan et al., 2000, Nature Medicine, 6, 698-702). Recent studies have shown that serine elastase, that is, NE or vascular elastase are important in cigarette smoke-induced muscularisation of small pulmonary arteries in guinea pigs (Wright et al., 2002, Am. J. Respir. Crit. Care Med., 166, 954-960).

NE plays a key role in experimental cerebral ischemic damage (Shimakura et al., 2000, Brain Research, 858, 55-60), ischemia-reperfusion lung injury (Kishima et al., 1998, Ann. Thorac. Surg. 65, 913-918) and myocardial ischemia in rat heart (Tiefenbacher et al., 1997, Eur. J. Physiol., 433, 563-570). Human NE levels in plasma are significantly increased above normal in inflammatory bowel diseases, for example, Crohn's disease and ulcerative colitis (Adeyemi et al., 1985, Gut, 26, 1306-1311). In addition NE has also been assumed to be involved in the pathogenesis of rheumatoid arthritis (Adeyemi et al., 1986, Rheumatol. Int., 6, 57). The development of collagen induced arthritis in mice is suppressed by a NE inhibitor (Kakimoto et al., 1995, Cellular Immunol. 165, 26-32).

Thus, human NE is known as one of the most destructive serine proteases and has been implicated in a variety of inflammatory diseases. The important endogenous inhibitor of human NE is $\alpha_1$-antitrypsin. The imbalance between human NE and antiprotease is believed to give rise to an excess of human NE resulting in uncontrolled tissue destruction. The protease/antiprotease balance may be upset by a decreased availability of $\alpha_1$-antitrypsin either through inactivation by oxidants such as cigarette smoke, or as a result of genetic inability to produce sufficient serum levels. Human NE has been implicated in the promotion or exacerbation of a number of diseases such as pulmonary emphysema, pulmonary fibrosis, adult respiratory distress syndrome (ARDS), ischemia reperfusion injury, rheumatoid arthritis and pulmonary hypertension.

WO 02/053543 discloses pyridone derivatives having affinity for cannabinoid 2-type receptor.

The present invention discloses novel 2-pyridione derivatives that are inhibitors of human neutrophil elastase and homologous serine proteases such as proteinase 3 and pancreatic elastase, and are thereby useful in therapy.

DISCLOSURE OF THE INVENTION

The present invention provides a compound of formula (I)

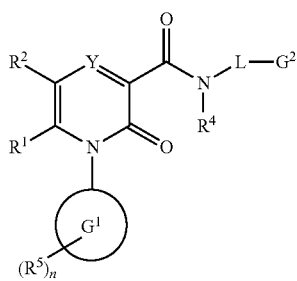

(I)

wherein:
Y represents $CR^3$ or N;
$R^1$ represents H or C1 to 6 alkyl;
$R^2$ represents phenyl or a five- or six-membered heteroaromatic ring containing 1 to 4 heteroatoms independently selected from O, S and N; said aromatic ring being optionally substituted by 1 to 3 substituents selected independently from OH, halogen, C1 to 6 alkyl, C1 to 6 alkoxy, $NR^{58}COR^{50}$, $COOR^{51}$, $COR^{52}$, $CONR^{53}R^{54}$ and $NR^{47}R^{48}$; said alkyl being optionally further substituted by OH, C1 to 6 alkoxy, CN or $CO_2R^{49}$;
$R^{47}$ and $R^{48}$ independently represent H, C1 to 6 alkyl or C2 to 6 alkanoyl;
$R^3$ represents H or F;
$G^1$ represents phenyl or a five- or six-membered heteroaromatic ring containing 1 to 3 heteroatoms independently selected from O, S and N;
$R^5$ represents H, halogen, C1 to 6 alkyl, CN, C1 to 6 alkoxy, $NO_2$, $NR^{14}R^{15}$, C1 to 3 alkoxy substituted by one or more F atoms or C1 to 3 alkoxy substituted by one or more F atoms;
$R^{14}$ and $R^{15}$ independently represent H or C1 to 3 alkyl; said alkyl being optionally further substituted by one or more F atoms;
n represents an integer 1, 2 or 3 and when n represents 2 or 3, each $R^5$ group is selected independently;
$R^4$ represents H or C1 to 6 alkyl; said alkyl being optionally further substituted by OH or C1 to 6 alkoxy;
or $R^4$ and L are joined together such that the group —$NR^4$L represents a 5 to 7 membered azacyclic ring optionally incorporating one further heteroatom selected from O, S and $NR^{16}$;
L represents a bond, O, S(O)p, $NR^{29}$ or C1 to 6 alkyl; said alkyl optionally incorporating a heteroatom selected from O, S and $NR^{16}$; and said alkyl being optionally further substituted by OH or OMe;
$G^2$ represents a monocyclic ring system selected from:
i) phenyl or phenoxy,
ii) a 5 or 6 membered heteroaromatic ring containing one to three heteroatoms independently selected from O, S and N,
iii) a C3 to 6 saturated or partially unsaturated cycloalkyl, or
iv) a C4 to 7 saturated or partially unsaturated heterocyclic ring containing one or two heteroatoms independently selected from O, $S(O)_p$ and $NR^{17}$ and optionally further incorporating a carbonyl group; or
$G^2$ represents a bicyclic ring system in which each of the two rings is independently selected from:
i) phenyl,
ii) a 5 or 6 membered heteroaromatic ring containing one to three heteroatoms independently selected from O, S and N,
iii) a C3 to 6 saturated or partially unsaturated cycloalkyl, or
iv) a C4 to 7 saturated or partially unsaturated heterocyclic ring containing one or two heteroatoms independently selected from O, $S(O)_p$ and $NR^{17}$ and optionally further incorporating a carbonyl group;
and the two rings are either fused together, or are bonded directly together or are separated by a linker group selected from O, $S(O)_q$ or $CH_2$,
said monocyclic or bicyclic ring system being optionally further substituted by one to three substituents independently selected from CN, OH, C1 to 6 alkyl, C1 to 6 alkoxy, halogen, $NR^{18}R^{19}$, $NO_2$, $OSO_2R^{38}$, $CO_2R^{20}$, C(=NH)$NH_2$, C(O)$NR^{21}R^{22}$, C(S)$NR^{23}R^{24}$, SC(=NH)$NH_2$, $NR^{31}$C(=NH)$NH_2$, $S(O)_sR^{25}$, $SO_2NR^{26}R^{27}$, C1 to 3 alkoxy substituted by one or more F atoms and C1 to 3 alkyl substituted by $SO_2R^{39}$, $NR^{56}R^{57}$ or by one or more F atoms;
or
when L does not represent an bond, $G^2$ may also represent H;

At each occurrence, p, q, s and t independently represent an integer 0, 1 or 2;

$R^{18}$ and $R^{19}$ independently represent H, C1 to 6 alkyl, formyl, C2 to 6 alkanoyl, $S(O)_rR^{32}$ or $SO_2NR^{33}R^{34}$; said alkyl group being optionally further substituted by halogen, CN, C1 to 4 alkoxy or $CONR^{41}R^{42}$;

$R^{25}$ represents H, C1 to 6 alkyl or C3 to 6 cycloalkyl; said alkyl group being optionally further substituted by one or more substituents selected independently from OH, CN, $CONR^{35}R^{36}$, $CO_2R^{37}$, $OCOR^{40}$, C3 to 6 cycloalkyl, a C4 to 7 saturated heterocyclic ring containing one or two heteroatoms independently selected from O, $S(O)_p$ and $NR^{43}$ and phenyl or a 5 or 6 membered heteroaromatic ring containing one to three heteroatoms is independently selected from O, S and N; said aromatic ring being optionally further substituted by one or more substituents selected independently from halogen, CN, C1 to 4 alkyl, C1 to 4 alkoxy, OH, $CONR^{44}R^{45}$, $CO_2R^{46}$, $S(O)_sR^{55}$ and $NHCOCH_3$;

$R^{32}$ represents H, C1 to 6 alkyl or C3 to 6 cycloalkyl;

$R^{16}$, $R^{17}$, $R^{20}$, $R^{21}$, $R^{22}$, $R^{23}$, $R^{24}$, $R^{26}$, $R^{27}$, $R^{29}$, $R^{31}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{49}$, $R^{50}$, $R^{51}$, $R^{52}$, $R^{53}$, $R^{54}$, $R^{55}$, $R^{56}$, $R^{57}$ and $R^{58}$ independently represent H or C1 to 6 alkyl;

and pharmaceutically acceptable salts thereof.

The compounds of formula (I) may exist in enantiomeric and/or tautomeric forms. It is to be understood that all enantiomers, diastereomers, racemates, tautomers and mixtures thereof are included within the scope of the invention.

Unless otherwise indicated, the term "C1 to 6 alkyl" referred to herein denotes a straight or branched chain alkyl group having from 1 to 6 carbon atoms. Examples of such groups include methyl, ethyl, n-propyl, i-propyl, n-butyl, i-butyl, t-butyl, pentyl and hexyl. The terms "C1 to 3 alkyl" and "C1 to 4 alkyl" are to be interpreted analogously.

Examples of "C1 to 3 alkyl substituted by one or more F atoms" include fluoromethyl, difluoromethyl, trifluoromethyl, 2,2,2-trifluoroethyl, 1,1-difluoroethyl, pentafluoroethyl and 3,3,3-trifluoropropyl.

Unless otherwise indicated, the term "C1 to 6 alkoxy" referred to herein denotes an oxygen substituent bonded to a straight or branched chain alkyl group having from 1 to 6 carbon atoms. Examples of such groups include methoxy, ethoxy, n-propoxy, i-propoxy, n-butoxy, i-butoxy and s-butoxy. The terms "C1 to 3 alkoxy" and "C1 to 4 alkoxy" are to be interpreted analogously.

Examples of "C1 to 3 alkoxy substituted by one or more F atoms" include fluoromethoxy, trifluoromethoxy, 2,2,2-trifluoroethoxy and 3,3,3-trifluoropropoxy.

Unless otherwise indicated, the term "C2 to 6 alkanoyl" referred to herein denotes a straight or branched chain alkyl group having from 1 to 5 carbon atoms bonded to the molecule via a carbonyl group. Examples of such groups include acetyl, propionyl and pivaloyl.

Unless otherwise indicated, the term "halogen" referred to herein denotes fluorine, chlorine, bromine and iodine.

Examples of a five or six membered heteroaromatic ring containing 1 to 4 heteroatoms independently selected from O, S and N include furan, thiophene, pyrrole, oxazole, 1,2,4-oxadiazole, 1,3,4-oxadiazole, isoxazole, imidazole, pyrazole, thiazole, triazole, thiadiazole, pyridine, pyrimidine, pyrazine and tetrazole. Examples of a five or six membered heteroaromatic ring containing 1 to 3 heteroatoms independently selected from O, S and N include furan, thiophene, pyrrole, oxazole, 1,2,4-oxadiazole, 1,3,4-oxadiazole, isoxazole, imidazole, pyrazole, thiazole, triazole, thiadiazole, pyridine, pyrimidine and pyrazine.

Unless otherwise indicated, the term "C3 to 6 saturated or partially unsaturated cycloalkyl" referred to herein denotes a 3 to 6 membered non-aromatic carbocyclic ring optionally incorporating one or more double bonds. Examples include cyclopropyl, cyclopentyl, cyclopentenyl, cyclohexyl and cyclohexenyl. The term "five- or six-membered saturated or partially unsaturated cycloalkyl ring" is to be interpreted analogously.

Unless otherwise indicated, the term "C4 to 7 saturated or partially unsaturated heterocyclic ring containing one or two heteroatoms independently selected from O, $S(O)_p$ and $NR^{17}$ and optionally further incorporating a carbonyl group" referred to herein denotes a 4 to 7 membered non-aromatic heterocyclic ring optionally incorporating one or more double bonds and optionally incorporating a carbonyl group. Examples include tetrahydrofuran, thiolane 1,1-dioxide, tetrahydropyran, 4-oxo-4H-pyran, pyrrolidine, pyrroline, imidazolidine, dihydro-oxazole, dihydropyrazole, 1,3-dioxolane, piperidine, piperazine, morpholine, perhydroazepine, pyrrolidone and piperidone. The term "five- or six-membered saturated or partially unsaturated heterocyclic ring containing one heteroatom selected from O, S and $NR^{13}$" is to be interpreted analogously.

Examples of a "5 to 7 membered azacyclic ring optionally incorporating one further heteroatom selected from O, S and $NR^{16}$" include pyrrolidine, piperidine, morpholine, thiomorpholine and piperazine.

In the definition of L, "C1 to 6 alkyl; said alkyl optionally incorporating a heteroatom selected from O, S and $NR^{16}$" embraces a straight or branched chain arrangement of 1 to 6 carbon atoms in which any two carbon atoms are optionally separated by O, S or $NR^{16}$. The definition thus includes, for example, methylene, ethylene, propylene, hexamethylene, ethylethylene, —$CH_2CH_2O$—$CH_2$—, —$CH_2CH_2O$—$CH_2$—$CH_2$—, —$CH_2CH_2S$— and —$CH_2CH_2NR^{16}$—.

Examples of bicyclic ring systems in which the two rings are either fused together, or are bonded directly together or are separated by a linker group selected from O, $S(O)_q$ or $CH_2$ include biphenyl, thienylphenyl, pyrazolylphenyl, phenoxyphenyl, phenylcyclopropyl, naphthyl, indanyl, quinolyl, tetrahydroquinolyl, benzofuranyl, indolyl, isoindolyl, indolinyl, benzofuranyl, benzothienyl, indazolyl, benzimidazolyl, benzthiazolyl, purinyl, isoquinolyl, chromanyl, indenyl, quinazolyl, quinoxalyl, chromanyl, isocromanyl, 3H-indolyl, 1H-indazolyl, quinuclidyl, tetrahydronaphthyl, dihydrobenzofuranyl, morpholine-4-ylphenyl, 1,3-benzodioxolyl, 1,1-dioxido-2,3-dihydro-1-benzothienyl, 2,3-dihydro-1,4-benzodioxinyl, 1,3-benzodioxinyl, and 3,4-dihydro-isochromenyl.

In one embodiment, Y in formula (I) represents $CR^3$. In another embodiment, Y represents N.

In one embodiment, $R^1$ in formula (I) represents C1 to 6 alkyl. In another embodiment, $R^1$ represents $CH_3$.

In one embodiment, $R^2$ in formula (I) represents optionally substituted phenyl. In another embodiment, $R^2$ in formula (I) represents an optionally substituted five- or six-membered heteroaromatic ring containing 1 to 4 heteroatoms selected independently from O, S and N. In another embodiment, $R^2$ in formula (I) represents an optionally substituted five- or six-membered heteroaromatic ring containing 1 to 3 heteroatoms selected independently from O, S and N. In another embodiment, $R^2$ in formula (I) represents an optionally substituted five-membered heteroaromatic ring containing 2 or 3 heteroatoms selected independently from O, S and N. In another embodiment, $R^2$ in formula (I) represents optionally substituted furan, pyridine, pyrimidine, pyrrole, thiophene, thiazolo, isoxazole, oxadiazole or thiadiazole. In another embodiment, $R^2$ in formula (I) represents optionally substituted isoxazole.

In one embodiment, $R^3$ in formula (I) represents H.

In one embodiment, $G^1$ in formula (I) represents phenyl or pyridyl. In another embodiment, $G^1$ in formula (I) represents phenyl.

In one embodiment, $R^5$ in formula (I) represents halogen, C1 to 6 alkyl, CN or C1 to 3 alkyl substituted by one or more F atoms. In another embodiment, $R^5$ in formula (I) represents Cl, $CH_3$, CN or $CF_3$.

In one embodiment, n represents the integer 1.

In another embodiment, $G^1$ in formula (I) represents phenyl, $R^5$ represents $CF_3$ and n represents the integer 1.

In one embodiment, $R^4$ represents H.

In one embodiment, L represents C1 to 6 alkyl. In another embodiment, L represents —$CH_2$—. In another embodiment, L represents $NR^{29}$ and $R^{29}$ represents H.

In one embodiment, $G^2$ represents an optionally substituted monocyclic ring system selected from:
i) phenyl,
ii) a 5 or 6 membered heteroaromatic ring containing one to three heteroatoms independently selected from O, S and N,
iii) a C3 to 6 saturated or partially unsaturated cycloalkyl, or
iv) a C4 to 7 saturated or partially unsaturated heterocyclic ring containing one or two heteroatoms independently selected from O, $S(O)_p$ and $NR^{17}$ and optionally further incorporating a carbonyl group.

In another embodiment, $G^2$ represents optionally substituted phenyl. In another embodiment, $G^2$ represents phenyl substituted by $OSO_2R^{38}$, $S(O)_sR^{25}$, $SO_2NR^{26}R^{27}$, $NR^{18}R^{19}$ (wherein at least one of $R^{18}$ and $R^{19}$ represents $S(O)_rR^{32}$ or $SO_2NR^{33}R^{34}$) or C1 to 3 alkyl substituted by $SO_2R^{39}$. In another embodiment, $G^2$ represents phenyl substituted by $S(O)_sR^{25}$ and $R^{25}$ represents C1 to 6 alkyl or C3 to 6 cycloalkyl and s represents the integer 2.

In another embodiment, $G^2$ represents an optionally substituted bicyclic ring system in which each of the two rings is independently selected from:
i) phenyl,
ii) a 5 or 6 membered heteroaromatic ring containing one to three heteroatoms independently selected from O, S and N,
iii) a C3 to 6 saturated or partially unsaturated cycloalkyl, or
iv) a C4 to 7 saturated or partially unsaturated heterocyclic ring containing one or two heteroatoms independently selected from O, $S(O)_p$ and $NR^{17}$ and optionally further incorporating a carbonyl group;
and the two rings are either fused together, or are bonded directly together or are separated by a linker group selected from O, $S(O)_q$ or $CH_2$.

In one embodiment, Y in formula (I) represents $CR^3$ and $R^3$ represents H; $R^1$ represents C1 to 6 alkyl; $R^2$ represents an optionally substituted five- or six-membered heteroaromatic ring containing 1 to 3 heteroatoms selected independently from O, S and N; $G^1$ represents phenyl; $R^5$ represents halogen, C1 to 6 alkyl, CN or C1 to 3 alkyl substituted by one or more F atoms; $R^4$ represents H; L represents C1 to 6 alkyl; and $G^2$ represents an optionally substituted monocyclic ring system selected from:
i) phenyl,
ii) a 5 or 6 membered heteroaromatic ring containing one to three heteroatoms independently selected from O, S and N,
iii) a C3 to 6 saturated or partially unsaturated cycloalkyl, or
iv) a C4 to 7 saturated or partially unsaturated heterocyclic ring containing one or two heteroatoms independently selected from O, $S(O)_p$ and $NR^{17}$ and optionally further incorporating a carbonyl group.

In one embodiment, Y in formula (I) represents $CR^3$ and $R^3$ represents H; $R^1$ represents C1 to 6 alkyl; $R^2$ represents an optionally substituted five-membered heteroaromatic ring containing 1 to 3 heteroatoms selected independently from O, S and N; $G^1$ represents phenyl; $R^5$ represents halogen, C1 to 6 alkyl, CN or C1 to 3 alkyl substituted by one or more F atoms; $R^4$ represents H; L represents C1 to 6 alkyl; and $G^2$ represents phenyl substituted by $OSO_2R^{38}$, $S(O)_sR^{25}$, $SO_2NR^{26}R^{27}$, $NR^{18}R^{19}$ (wherein at least one of $R^{18}$ and $R^{19}$ represents $S(O)_rR^{32}$ or $SO_2NR^{33}R^{34}$) or C1 to 3 alkyl substituted by $SO_2R^{39}$.

In one embodiment, Y in formula (I) represents $CR^3$ and $R^3$ represents H; $R^1$ represents methyl; $R^2$ represents an optionally substituted five-membered heteroaromatic ring containing 2 or 3 heteroatoms selected independently from O, S and N; $G^1$ represents phenyl; $R^5$ represents Cl, $CH_3$, CN or $CF_3$; $R^4$ represents H; L represents C1 to 6 alkyl; and $G^2$ represents phenyl substituted by $OSO_2R^{38}$, $S(O)_sR^{25}$, $SO_2NR^{26}R^{27}$, $NR^{18}R^{19}$ (wherein at least one of $R^{18}$ and $R^{19}$ represents $S(O)_rR^{32}$ or $SO_2NR^{33}R^{34}$) or C1 to 3 alkyl substituted by $SO_2R^{39}$.

In one embodiment, Y in formula (I) represents $CR^3$ and $R^3$ represents H; $R^1$ represents methyl; $R^2$ represents an optionally substituted isoxazole ring; $G^1$ represents phenyl; $R^5$ represents Cl, $CH_3$, CN or $CF_3$; $R^4$ represents H; L represents C1 to 3 alkyl; and $G^2$ represents phenyl substituted by $OSO_2R^{38}$, $S(O)_sR^{25}$, $SO_2NR^{26}R^{27}$, $NR^{18}R^{19}$ (wherein at least one of $R^{18}$ and $R^{19}$ represents $S(O)_rR^{32}$ or $SO_2NR^{33}R^{34}$) or C1 to 3 alkyl substituted by $SO_2R^{39}$.

In one embodiment, Y in formula (I) represents $CR^3$ and $R^3$ represents H; $R^1$ represents methyl; $R^2$ represents an optionally substituted five-membered heteroaromatic ring containing 2 or 3 heteroatoms selected independently from O, S and N; $G^1$ represents phenyl; $R^5$ represents Cl, $CH_3$, CN or $CF_3$; $R^4$ represents H; L represents C1 to 6 alkyl; and $G^2$ represents phenyl substituted by $S(O)_sR^{25}$ and $R^{25}$ represents C1 to 6 alkyl or C3 to 6 cycloalkyl and s represents the integer 2.

In one embodiment, Y in formula (I) represents $CR^3$ and $R^3$ represents H; $R^1$ represents methyl; $R^2$ represents an optionally substituted isoxazole ring; $G^1$ represents phenyl; $R^5$ represents Cl, $CH_3$, CN or $CF_3$; $R^4$ represents H; L represents C1 to 3 alkyl; and $G^2$ represents phenyl substituted by $S(O)_sR^{25}$ and $R^{25}$ represents C1 to 6 alkyl or C3 to 6 cycloalkyl and s represents the integer 2.

In one embodiment, Y in formula (I) represents $CR^3$ or N; $R^1$ represents H or C1 to 6 alkyl; $R^2$ represents phenyl or a five- or six-membered heteroaromatic ring containing 1 to 4 heteroatoms independently selected from O, S and N; said aromatic ring being optionally substituted by 1 to 3 substituents selected independently from OH, halogen, C1 to 6 alkyl, C1 to 6 alkoxy, $NCOR^{50}$, $COOR^{51}$, $COR^{52}$, $CONR^{53}R^{54}$ and $NR^{47}R^{48}$; said alkyl being optionally further substituted by OH, CN or $CO_2R^{49}$; $R^{47}$ and $R^{48}$ independently represent H, C1 to 6 alkyl or C2 to 6 alkanoyl; $R^3$ represents H or F; $G^1$ represents phenyl or a five- or six-membered heteroaromatic ring containing 1 to 3 heteroatoms independently selected from O, S and N; $R^5$ represents H, halogen, C1 to 6 alkyl, CN, C1 to 6 alkoxy, $NO_2$, $NR^{14}R^{15}$, C1 to 3 alkyl substituted by one or more F atoms or C1 to 3 alkoxy substituted by one or more F atoms; $R^{14}$ and $R^{15}$ independently represent H or C1 to 3 alkyl; said alkyl being optionally further substituted by one or more F atoms; n represents an integer 1, 2 or 3 and when n represents 2 or 3, each $R^5$ group is selected independently; $R^4$ represents H or C1 to 6 alkyl; said alkyl being optionally further substituted by OH or C1 to 6 alkoxy; or $R^4$ and L are joined together such that the group —$NR^4L$ represents a 5 to 7 membered azacyclic ring optionally incorporating one further heteroatom selected from O, S and $NR^{16}$; L represents a bond, O, $NR^{29}$ or C1 to 6 alkyl; said alkyl optionally incorporating a heteroatom selected from O, S and $NR^{16}$; and said alkyl being optionally further substituted by OH or OMe; $G^2$ represents a monocyclic ring system selected from:
i) phenyl or phenoxy,
ii) a 5 or 6 membered heteroaromatic ring containing one to three heteroatoms independently selected from O, S and N,
iii) a C3 to 6 saturated or partially unsaturated cycloalkyl, or
iv) a C4 to 7 saturated or partially unsaturated heterocyclic ring containing one or two heteroatoms independently selected from O, $S(O)_p$ and $NR^{17}$ and optionally further incorporating a carbonyl group; or $G^2$ represents a bicyclic ring system in which each of the two rings is independently selected from:
i) phenyl,
ii) a 5 or 6 membered heteroaromatic ring containing one to three heteroatoms independently selected from O, S and N,
iii) a C3 to 6 saturated or partially unsaturated cycloalkyl, or
iv) a C4 to 7 saturated or partially unsaturated heterocyclic ring containing one or two heteroatoms independently selected from O, $S(O)_p$ and $NR^{17}$ and optionally further incorporating a carbonyl group;
and the two rings are either fused together, or are bonded directly together or are separated by a linker group selected from O, $S(O)_q$ or $CH_2$; said monocyclic or bicyclic ring system being optionally further substituted by one to three substituents independently selected from CN, OH, C1 to 6 alkyl, C1 to 6 alkoxy, halogen, $NR^{18}R^{19}$, $NO_2$, $OSO_2R^{38}$, $CO_2R^{20}$, $C(=NH)NH_2$, $C(O)NR^{21}R^{22}$, $C(S)NR^{23}R^{24}$, $SC(=NH)NH_2$, $NR^{31}C(=NH)NH_2$, $S(O)_sR^{25}$, $SO_2NR^{26}R^{27}$, C1 to 3 alkoxy substituted by one or more F atoms and C1 to 3 alkyl substituted by $SO_2R^{39}$ or by one or more F atoms; or when L does not represent an bond, $G^2$ may also represent H; p, q, s and t independently represent an integer 0, 1 or 2; $R^{18}$ and $R^{19}$, independently represent H, C1 to 6 alkyl, formyl, C2 to 6 alkanoyl, $S(O)_tR^{32}$ or $SO_2NR^{33}R^{34}$; said alkyl group being optionally further substituted by halogen, CN, C1 to 4 alkoxy or $CONR^{41}R^{42}$; $R^{25}$ represents H, C1 to 6 alkyl or C3 to 6 cycloalkyl; said alkyl group being optionally further substituted by one or more substituents selected independently from OH, CN, $CONR^{35}R^{36}$, $CO_2R^{37}$, $OCOR^{40}$, C3 to 6 cycloalkyl, a C4 to 7 saturated heterocyclic ring containing one or two heteroatoms independently selected from O, $S(O)_p$ and $NR^{43}$ and phenyl or a 5 or 6 membered heteroaromatic ring containing one to three heteroatoms independently selected from O, S and N; said aromatic ring being optionally further substituted by one or more substituents selected independently from halogen, CN, C1 to 4 alkyl, C1 to 4 alkoxy, OH, $CONR^{44}R^{45}$, $CO_2R^{46}$, $S(O)_sR^{55}$ and $NHCOCH_3$; $R^{32}$ represents H, C1 to 6 alkyl or C3 to 6 cycloalkyl; and $R^{16}$, $R^{17}$, $R^{20}$, $R^{21}$, $R^{22}$, $R^{23}$, $R^{24}$, $R^{26}$, $R^{27}$, $R^{29}$, $R^{31}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{49}$, $R^{50}$, $R^{51}$, $R^{52}$, $R^{53}$, $R^{54}$ and $R^{55}$ independently represent H or C1 to 6 alkyl.

In another aspect, the invention specifically provides any compound as described in the Examples herein, or the free base thereof or a pharmaceutically acceptable salt thereof. Particular compounds include:

6-methyl-N-[4-(methylsulfonyl)benzyl]-2-oxo-5-phenyl-1-[3-(trifluoromethyl)phenyl]-1,2-dihydropyridine-3-carboxamide;

5-[4-(hydroxymethyl)phenyl]-6-methyl-N-[4-(methylsulfonyl)benzyl]-2-oxo-1-[3-(trifluoromethyl)phenyl]-1,2-dihydropyridine-3-carboxamide;

5-furan-3-yl-6-methyl-2-oxo-1-(3-trifluoromethylphenyl)-1,2-dihydro-pyridine-3-carboxylic acid 4-methanesulfonyl-benzylamide;

6'-methoxy-2-methyl-N-[4-(methylsulfonyl)benzyl]-6-oxo-1-[3-(trifluoromethyl)phenyl]-1,6-dihydro-3,3'-bipyridine-5-carboxamide;

5-(2-methoxypyrimidin-5-yl)-6-methyl-N-[4-(methylsulfonyl)benzyl]-2-oxo-1-[3-(trifluoromethyl)phenyl]-1,2-dihydropyridine-3-carboxamide;

5-[4-(acetylamino)phenyl]-6-methyl-N-[4-(methylsulfonyl)benzyl]-2-oxo-1-[3-(trifluoromethyl)phenyl]-1,2-dihydropyridine-3-carboxamide;

6-methyl-2-oxo-5-(1H-pyrrol-3-yl)-1-(3-trifluoromethylphenyl)-1,2-dihydro-pyridine-3-carboxylic acid 4-methanesulfonyl-benzylamide;

5-furan-2-yl-6-methyl-2-oxo-1-(3-trifluoromethylphenyl)-1,2-dihydro-pyridine-3-carboxylic acid 4-methanesulfonyl-benzylamide;

6-methyl-2-oxo-5-thiophen-3-yl-1-(3-trifluoromethylphenyl)-1,2-dihydro-pyridine-3-carboxylic acid 4-methanesulfonyl-benzylamide;

6-methyl-2-oxo-5-thiophen-2-yl-1-(3-trifluoromethylphenyl)-1,2-dihydro-pyridine-3-carboxylic acid 4-methanesulfonyl-benzylamide;

5-(3,5-dimethyl-isoxazol-4-yl)-6-methyl-2-oxo-1-(3-trifluoromethylphenyl)-1,1-dihydro-pyridine-3-carboxylic acid 4-methanesulfonyl-benzylamide;

5-(2,4-dimethoxy-pyrimidin-5-yl)-6-methyl-2-oxo-1-(3-trifluoromethylphenyl)-1,2-dihydro-pyridine-3-carboxylic acid 4-methanesulfonyl-benzylamide;

5-(2,4-dioxo-1,2,3,4-tetrahydro-pyrimidin-5-yl)-6-methyl-2-oxo-1-(3-trifluoromethyl-phenyl)-1,2-dihydro-pyridine-3-carboxylic acid 4-methanesulfonyl-benzylamide;

6-methyl-5-(5-methyl-[1,3,4]oxadiazol-2-yl)-2-oxo-1-(3-trifluoromethylphenyl)-1,2-dihydro-pyridine-3-carboxylic acid 4-methanesulfonyl-benzylamide;

6-methyl-2-oxo-5-(5-propyl-[1,3,4]oxadiazol-2-yl)-1-(3-trifluoromethylphenyl)-1,2-dihydro-pyridine-3-carboxylic acid 4-methanesulfonyl-benzylamide;

{5-[5-(4-methanesulfonyl-benzylcarbamoyl)-2-methyl-6-oxo-1-(3-trifluoromethyl-phenyl)-1,6-dihydro-pyridin-3-yl]-[1,3,4]oxadiazol-2-yl}-acetic acid ethyl ester;

5-(5-cyanomethyl-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

5-(5-amino-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

5-(5-amino-[1,3,4]thiadiazol-2-yl)-6-methyl-2-oxo-1-(3-trifluoromethylphenyl)-1,2-dihydro-pyridine-3-carboxylic acid 4-methanesulfonyl-benzylamide;

5-(5-ethylamino-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

5-(5-N,N-dimethylamino-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide;

6-methyl-N-[4-(methylsulfonyl)benzyl]-2-oxo-5-pyrazin-2-yl-1-[3-(trifluoro-methyl)phenyl]-1,2-dihydropyridine-3-carboxamide;

6-methyl-5-oxazol-2-yl-2-oxo-1-(3-trifluoromethylphenyl)-1,2-dihydro-pyridine-3-carboxylic acid 4-methanesulfonyl-benzylamide;

6-methyl-5-(1-methyl-1H-imidazol-2-yl)-2-oxo-1-(3-trifluoromethylphenyl)-1,2-dihydro-pyridine-3-carboxylic acid 4-methanesulfonyl-benzylamide;

6-methyl-2-oxo-5-(1H-pyrazol-4-yl)-1-(3-trifluoromethylphenyl)-1,2-dihydro-pyridine-3-carboxylic acid 4-methanesulfonyl-benzylamide;

6-methyl-N-[4-(methylsulfonyl)benzyl]-2-oxo-5-pyrimidin-2-yl-1-[3-(trifluoro-methyl)phenyl]-1,2-dihydropyridine-3-carboxamide;

6-methyl-5-(2-methyl-2H-pyrazol-3-yl)-2-oxo-1-(trifluoromethylphenyl)-1,2-dihydro-pyridine-3-carboxylic acid 4-methanesulfonyl-benzylamide;

6-methyl-5-(3-methylisoxazol-4-yl)-N-[4-(methylsulfonyl)benzyl]-2-oxo-1,3-(trifluoromethyl)phenyl)-1,2-dihydro-pyridine-3-carboxamide;

6-methyl-5-(3-methyl-[1,2,4]oxadiazol-5-yl)-2-oxo-1-(3-trifluoromethylphenyl)-1,2-dihydro-pyridine-3-carboxylic acid 4-methanesulfonyl-benzylamide;

6-methyl-5-(3-methylisoxazol-5-yl)-N-[4-(methylsulfonyl)benzyl]-2-oxo-1-[3-(trifluoromethyl)phenyl]-1,2-dihydropyridine-3-carboxamide;

5-(3,5-dimethylisoxazol-4-yl)-N-[4-(isopropylsulfonyl)benzyl]-6-methyl-2-oxo-1-[3-(trifluoromethyl)phenyl]-1,2-dihydropyridine-3-carboxamide;

5-(3,5-dimethylisoxazol-4-yl)-N-[4-(ethylsulfonyl)benzyl]-6-methyl-2-oxo-1-[3-(trifluoromethyl)phenyl]-1,2-dihydropyridine-3-carboxamide;

N-[4-(cyclopropylsulfonyl)benzyl]-5-(3,5-dimethylisoxazol-4-yl)-6-methyl-2-oxo-1-[3-(trifluoromethyl)phenyl]-1,2-dihydropyridine-3-carboxamide;

1-(3-cyanophenyl)-5-(3,5-dimethylisoxazol-4-yl)-6-methyl-N-[4-(methylsulfonyl)benzyl]-2-oxo-1,2-dihydropyridine-3-carboxamide;

1-(3-chlorophenyl)-5-(3,5-dimethyl-isoxazol-4-yl)-6-methyl-2-oxo-1,2-dihydro-pyridine-3-carboxylic acid 4-Methanesulfonyl-benzylamide;

5-(3,5-dimethyl-isoxazol-4-yl)-6-methyl-2-oxo-1-m-tolyl-1,2-dihydro-pyridine-3-carboxylic acid 4-methanesulfonyl-benzylamide;

5-(5-isopropyl-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

6-methyl-5-[1,3,4]oxadiazol-2-yl)-2-oxo-1-(3-trifluoromethylphenyl)-1,2-dihydro-pyridine-3-carboxylic acid 4-methanesulfonyl-benzylamide;

5-(5-hydroxy-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

6-methyl-5-(5-methyl-4H-[1,2,4]triazol-3-yl)-2-oxo-1-(3-trifluoromethylphenyl)-1,2-dihydro-pyridine-3-carboxylic acid 4-methylsulfonyl-benzylamide;

5-(4,5-dimethyl-4H-[1,2,4]triazol-3-yl)-6-methyl-2-oxo-1-(3-trifluoromethylphenyl)-1,2-dihydro-pyridine-3-carboxylic acid 4-methanesulfonyl-benzylamide;

5-(5-methoxymethyl-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

N-[4-(isopropylsulfonyl)benzyl]-6-methyl-5-(5-methyl-1,3,4-oxadiazol-2-yl)-2-oxo-1-[3-(trifluoromethyl)phenyl]-1,2-dihydropyridine-3-carboxamide;

N-[4-(ethylsulfonyl)benzyl]-6-methyl-5-(5-methyl-1,3,4-oxadiazol-2-yl)-2-oxo-1-[3-(trifluoromethyl)phenyl]-1,2-dihydropyridine-3-carboxamide;

N-[4-(cyclopropylsulfonyl)benzyl]-6-methyl-5-(5-methyl-1,3,4-oxadiazol-2-yl)-2-oxo-1-[3-(trifluoromethyl)phenyl]-1,2-dihydropyridine-3-carboxamide;

6-methyl-5-[1,3,4]oxadiazol-2-yl-2-oxo-1-(3-trifluoromethylphenyl)-1,2-dihydro-pyridine-3-carboxylic acid 4-(propane-2-sulfonyl)-benzylamide;

6-methyl-5-[1,3,4]oxadiazol-2-yl-2-oxo-1-(3-trifluoromethylphenyl)-1,2-dihydro-pyridine-3-carboxylic acid 4-cyclopropanesulfonyl-benzylamide;

6-methyl-5-(2-methyl-1,3-oxazol-4-yl)-N-[4-(methylsulfonyl)benzyl]-2-oxo-1-[3-(trifluoromethyl)phenyl]-1,2-dihydropyridine-3-carboxamide;

6-methyl-N-[4-(methylsulfonyl)benzyl]-5-(1,3-oxazol-4-yl)-2-oxo-1-[3-(trifluoromethyl)phenyl]-1,2-dihydropyridine-3-carboxamide;

5-(2-amino-thiazol-4-yl)-6-methyl-2-oxo-1-(3-trifluoromethylphenyl)-1,2-dihydro-pyridine-j-carboxylic acid 4-methanesulfonyl-benzylamide;

5-(2,5-dimethyl-1,3-oxazol-4-yl)-6-methyl-N-[4-(methylsulfonyl)benzyl]-2-oxo-1-[3-(trifluoromethyl)phenyl]-1,2-dihydropyridine-3-carboxamide;

6-methyl-5-(5-methyl-1,3-oxazol-4-A-N-[4-(methylsulfonyl)benzyl]-2-oxo-1-[3-(trifluoromethyl)phenyl]-1,2-dihydropyridine-3-carboxamide;

5-(2-amino-5-methyl-thiazol-4-yl)-6-methyl-2-oxo-1-(3-trifluoromethylphenyl)-1,2-dihydro-pyridine-3-carboxylic acid 4-methanesulfonyl-benzylamide;

5-(2-hydroxymethyl-5-methyl-thiazol-4-yl)-6-methyl-2-oxo-1-(3-trifluoromethylphenyl)-1,2-dihydro-pyridine-3-carboxylic acid 4-methanesulfonyl-benzylamide;

6-methyl-5-(5-methyl-[1,2,4]oxadiazol-3-yl)-2-oxo-1-(3-trifluoromethylphenyl)-1,2-dihydro-pyridine-3-carboxylic acid 4-methanesulfonyl-benzylamide;

6-methyl-5-[1,2,4]oxadiazol-3-yl-2-oxo-1-(3-trifluoromethylphenyl)-1,2-dihydro-pyridine-3-carboxylic acid 4-methanesulfonyl-benzylamide;

6-methyl-2-oxo-5-(1H-tetrazol-5-yl)-1-(3-trifluoromethylphenyl)-1,2-dihydro-pyridine-3-carboxylic acid 4-methanesulfonyl-benzylamide;

6-methyl-5-(4-methyl-oxazol-2-yl)-2-oxo-1-(3-trifluoromethylphenyl)-1,2-dihydro-pyridine-3-carboxylic acid 4-methanesulfonyl-benzylamide;

5-(4,5-dimethyl-oxazol-2-yl)-6-methyl-2-oxo-1-(3-trifluoromethylphenyl)-1,2-dihydro-pyridine-3-carboxylic acid 4-methanesulfonyl-benzylamide;

N-(cyclohexylmethyl)-6-methyl-2-oxo-5-phenyl-1-[3-(trifluoromethyl)phenyl]-1,2-dihydropyridine-3-carboxamide;

6-methyl-N-(2-morpholin-4-ylethyl)-2-oxo-5-phenyl-1-[3-(trifluoromethyl)phenyl]-1,2-dihydropyridine-3-carboxamide;

6-methyl-2-oxo-5-phenyl-N-1H-1,2,4-triazol-3-yl-1-[3-(trifluoromethyl)phenyl]-1,2-dihydropyridine-3-carboxamide;

N-[2-(1H-indol-3-yl)ethyl]-6-methyl-2-oxo-5-phenyl-1-[3-(trifluoromethyl)phenyl]-1,2-dihydropyridine-3-carboxamide;

6-methyl-2-oxo-5-phenyl-N-(1-phenylethyl)-1-[3-(trifluoromethyl)phenyl]-1,2-dihydropyridine-3-carboxamide;

6-methyl-2-oxo-5-phenyl-N-(2-phenylethyl)-1-[3-(trifluoromethyl)phenyl]-1,2-dihydropyridine-3-carboxamide;

6-methyl-2-oxo-5-phenyl-N-[(2R)-2-phenylcyclopropyl]-1-[3-(trifluoromethyl)phenyl]-1,2-dihydropyridine-3-carboxamide;

N-(2,3-dihydro-1H-inden-2-yl)-6-methyl-2-oxo-5-phenyl-1-[3-(trifluoromethyl)phenyl]-1,2-dihydropyridine-3-carboxamide;

N-[(1-ethylpyrrolidin-2-yl)methyl]-6-methyl-2-oxo-5-phenyl-1-[3-(trifluoromethyl)-phenyl]-1,2-dihydropyridine-3-carboxamide;

6-methyl-N-(1-naphthylmethyl)-2-oxo-5-phenyl-1-[3-(trifluoromethyl)phenyl]-1,2-dihydropyridine-3-carboxamide;

N-(1,3-benzodioxol-5-ylmethyl)-6-methyl-2-oxo-5-Phenyl-1-[3-(trifluoromethyl)phenyl]-1,2-dihydropyridine-3-carboxamide;
N-(2-chloro-4-fluorobenzyl)-6-methyl-2-oxo-5-phenyl-1-[3-(trifluoromethyl)phenyl]-1,2-dihydropyridine-3-carboxamide;
6-methyl-2-oxo-5-phenyl-N-(2-thienylmethyl)-1-[3-(trifluoromethyl)phenyl]-1,2-dihydropyridine-3-carboxamide;
N-(2-cyclohex-1-en-1-ylethyl)-6-methyl-2-oxo-5-phenyl-1-[3-(trifluoromethyl)phenyl]-1,2-dihydropyridine-3-carboxamide;
6-methyl-2-oxo-N-(4-phenoxybenzyl)-5-phenyl-1-[3-(trifluoromethyl)phenyl]-1,2-dihydropyridine-3-carboxamide;
N-[(2,5-dimethyl-3-furyl)methyl]-6-methyl-2-oxo-5-phenyl-1-[3-(trifluoromethyl)-phenyl]-1,2-dihydropyridine-3-carboxamide;
N-{2-[4-(aminosulfonyl)phenyl]ethyl}-6-methyl-2-oxo-5-phenyl-1-[3-(trifluoromethyl)-phenyl]-1,2-dihydropyridine-3-carboxamide;
6-methyl-2-oxo-5-phenyl-N-[4-(1H-pyrazol-1-yl)benzyl]-1-[3-(trifluoromethyl)phenyl]-1,2-dihydropyridine-3-carboxamide;
6-methyl-2-oxo-N-phenoxy-5-phenyl-1-[3-(trifluoromethyl)phenyl]-1,2-dihydro-pyridine-3-carboxamide;
N-[(6-fluoro-4H-1,3-benzodioxin-8-yl)methyl]-6-methyl-2-oxo-5-phenyl-1-[3-(trifluoromethyl)phenyl]-1,2-dihydropyridine-3-carboxamide;
6-methyl-2-oxo-5-phenyl-N-[2-(tetrahydro-2H-pyran-4-yl)ethyl]-1-[3-(trifluoromethyl)-phenyl]-1,2-dihydropyridine-3-carboxamide;
6-methyl-2-oxo-5-phenyl-N-[3-(1H-pyrazol-1-yl)propyl]-1-[3-(trifluoromethyl)phenyl]-1,2-dihydropyridine-3-carboxamide;
6-methyl-N-[(1-methyl-1H-pyrazol-4-yl)methyl]-2-oxo-5-phenyl-1-[3-(trifluoromethyl)-phenyl]-1,2-dihydropyridine-3-carboxamide;
6-methyl-2-oxo-5-phenyl-N-[(1-phenyl-1H-pyrazol-4-yl)methyl]-1-[3-(trifluoromethyl)-phenyl]-1,2-dihydropyridine-3-carboxamide;
N-[(5-methoxy-4-oxo-4H-pyran-2-yl)methyl]-6-methyl-2-oxo-5-phenyl-1-[3-(trifluoromethyl)phenyl]-1,2-dihydropyridine-3-carboxamide;
N-(3-azepan-1-ylpropyl)-6-methyl-2-oxo-5-phenyl-1-[3-(trifluoromethyl)phenyl]-1,2-dihydropyridine-3-carboxamide;
N-(4-cyanobenzyl)-6-methyl-2-oxo-5-phenyl-1-[3-(trifluoromethyl)phenyl]-1,2-dihydropyridine-3-carboxamide;
6-methyl-2-oxo-N-[3-(5-oxo-4,5-dihydro-1H-pyrazol-4-yl)propyl]-5-phenyl-1-[3-(trifluoromethyl)phenyl]-1,2-dihydropyridine-3-carboxamide;
6-methyl-5-(2-methyl-2H-pyrazol-3-yl)-2-oxo-1-(3-trifluoromethylphenyl)-1,2-dihydro-pyridine-3-carboxylic acid (3-methyl-isoxazol-5-ylmethyl)-amide;
6-methyl-5-(2-methyl-2H-pyrazol-3-yl)-2-oxo-1-(3-trifluoromethylphenyl)-1,2-dihydro-pyridine-3-carboxylic acid (5-methanesulfonylmethyl-[1,2,4]oxadiazol-3-ylmethyl)-amide;
6-methyl-5-(2-methyl-2H-pyrazol-3-yl)-2-oxo-1-(3-trifluoromethylphenyl)-1,2-dihydro-pyridine-3-carboxylic acid ([1,2,4]oxadiazol-3-ylmethyl)-amide;
6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide;
5-(3,5-dimethylisoxazol-4-yl)-6-methyl-N-{[5-(methylsulfonyl)pyridin-2-yl]methyl}-2-oxo-1-[3-(trifluoromethyl)phenyl]-1,2-dihydropyridine-3-carboxamide; acceptable salts thereof.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

In a further aspect the invention provides a process for the preparation of a compound of formula (I) which comprises:

a) reacting a compound of forula (II)

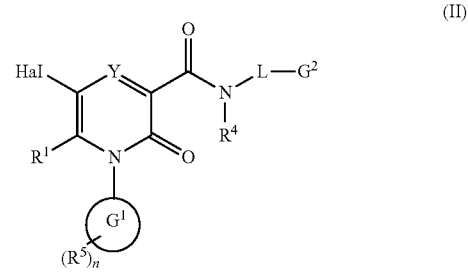

(II)

wherein $R^1$, $R^4$, $R^5$, Y, $G^1$, $G^2$, L and n are as defined in formula (I) and Hal represents a halogen atom, preferably bromo or iodo;

with a nucleophile $R^2$-M wherein $R^2$ is as defined in formula (I) and M represents an organo-tin or organo boronic acid group; or b) when $R^2$ represents a 1,3,4-oxadiazol-2-yl or a 1,3,4-thiadiazol-2-yl ring, reacting a compound of formula (III)

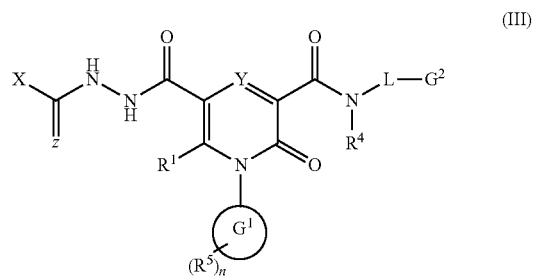

(III)

wherein $R^1$, $R^4$, $R^5$, Y, $G^1$, $G^2$, L and n are as defined in formula (I), Z represents O or S and X represents C1 to 6 alkyl or $NR^{47}R^{48}$ and $R^{47}$ and $R^{48}$ are as defined in formula (I); with a suitable dehydrating agent such as phosphoryl chloride or trimethylsilyl polyphosphate; or c) reacting a compound of formula (XV)

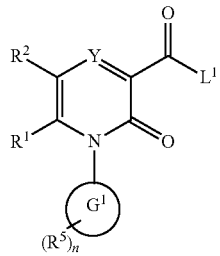

wherein $R^1$, $R^2$, $R^5$, n, $G^1$, and Y are as defined in formula (I) and $L^1$ represents a leaving group, with a compound of formula (IX) or a salt thereof

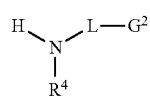

wherein $R^4$, $G^2$ and L are as defined in formula (I);

and where desired or necessary converting the resultant compound of formula (I), or another salt thereof, into a pharmaceutically acceptable salt thereof; or converting one compound of formula (I) into another compound of formula (I); and where desired converting the resultant compound of formula (I) into an optical isomer thereof.

In process (a), the reaction is carried out at a suitable temperature, generally between 50° C. and 150° C. in a suitable solvent such as toluene in the presence of a transition metal catalyst such as palladium. Optionally, the reaction may be carried out in the presence of a base such as potassium carbonate.

In process (b), the reaction is carried out at a suitable temperature, generally between 20° C. and 100° C. in a suitable solvent such as dichloromethane, if necessary, using a sealed vial.

The man skilled in the art will readily appreciate that compounds of formula (I) wherein $R^2$ represents a five-membered heteroaromatic ring other than a 1,3,4-oxadiazol-2-yl or a 1,3,4-thiadiazol-2-yl ring may also be prepared by processes in which the final step is the ring closure of the five-membered heteroaromatic ring. Specific examples of such processes are described in the Examples section of this specification. Such processes form another aspect of the present invention.

In process (c), the reaction is carried out at a suitable temperature, generally between 0° C. and the boiling point of the solvent, in a suitable solvent such as dichloromethane or N-methylpyrrolidinone. The process is optionally carried out in the presence of a base and/or a coupling reagent such as HATU, HOAT, HOBT or DIEA. Suitable leaving groups $L^1$ include OH and halogen.

Compounds of formula (III) may be prepared by reacting a compound of formula (IV)

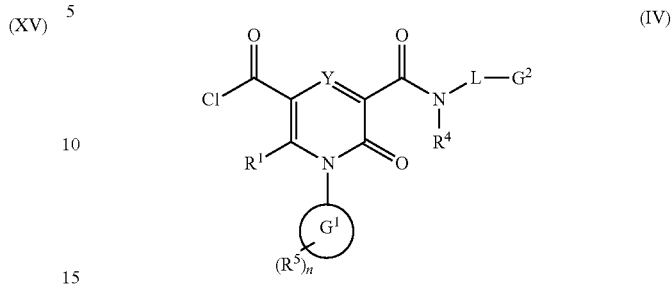

wherein $R^1$, $R^4$, $R^5$, Y, $G^1$, $G^2$, L and n are as defined in formula (I);

with a compound of the general formula (V)

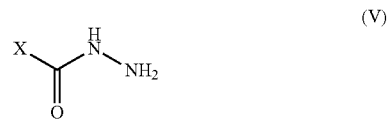

wherein X is defined in formula (III). This reaction may be carried out at a suitable temperature, generally between 0° C. and 50° C. in a suitable solvent such as 1,4-dioxane.

Compounds of formula (IV) may be prepared by reacting a compound of formula (VI)

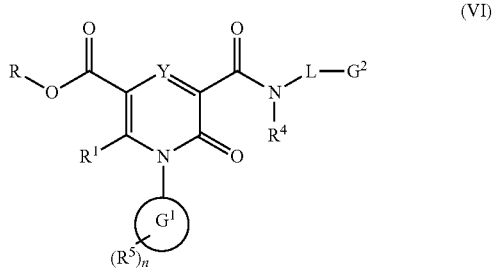

wherein $R^1$, $R^4$, $R^5$, Y, $G^1$, $G^2$, L and n are as defined in formula (I) and R represents C1 to 6 alkyl;

with an aqueous base such as sodium hydroxide, followed by subsequent treatment of the product with a chlorinating agent such as thionyl chloride. This process may be carried out at a suitable temperature; generally between 10° C. and 50° C. in a suitable solvent such as tetrahydrofuran or dichloromethane.

Compounds of formula (VI) may be prepared by reacting a compound of formula (II) with carbon monoxide in the presence of an alcohol such as methanol or ethanol and in the presence of a suitable transition metal catalyst. This process may be carried out at a suitable temperature, generally between 50° C. and 150° C. in a suitable solvent such as methanol or ethanol in a carbon monoxide atmosphere at elevated pressure, generally between 2 and 10 atmospheres. The reaction is performed in the presence of a transition metal catalyst such as palladium.

Compounds of formula (II) may be prepared by reacting a compound of forula (VII)

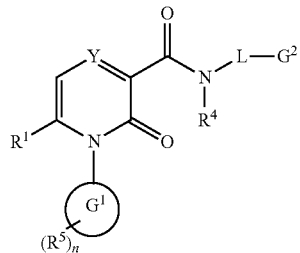
(VII)

wherein $R^1$, $R^4$, $R^5$, Y, $G^1$, $G^2$, L and n are as defined in formula (I), with a halogenating agent, such as N-iodosuccinimide. This process is carried out at a suitable temperature, generally between 0° C. and 50° C. in a suitable solvent such as acetonitrile in the presence of an acid such as trifluoromethanesulfonic acid.

Compounds of formula (VII) can be prepared by reacting a compound of formula (VIII)

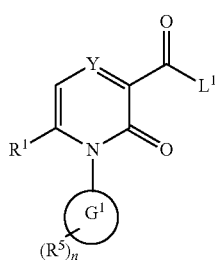
(VIII)

wherein $R^1$, $R^5$, Y, $G^1$ and n are as defined in formula (I) and $L^1$ represents a leaving group, with an amine of formula (IX) or a salt thereof

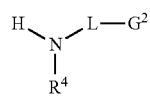
(IX)

wherein $R^4$, $G^2$ and L are as defined in formula (I). The process is carried out at a suitable temperature, generally between 0° C. and the boiling point of the solvent, in a suitable solvent such as dichloromethane or N-methylpyrrolidinone. The process is optionally carried out in the presence of a base and/or a coupling reagent such as HATU, HOAT, HOBT or DIEA. Suitable leaving groups $L^1$ include OH and halogen.

Compounds of formula (VIII) wherein Y is $CR^3$, $L^1$ is OH and $R^3$ is hydrogen can be prepared by condensing a compound of formul (X)

(X)

wherein $R^1$ is as defined in formula (I); with a compound of formula (XI)

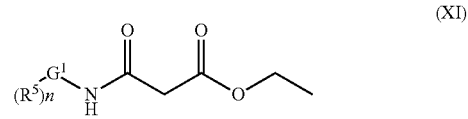
(XI)

wherein $G^1$, $R^5$ and n are as defined in formula (I), in the presence of a suitable base, such as sodium methoxide, in a suitable solvent, such as ethanol, followed by hydrolysis using a suitable base such as sodium hydroxide.

In general, compounds of formulae (X) and (XI) are either known or may be prepared using methods that will be readily apparent to the man skilled in the art. For example, compounds of formula (X) can be prepared according to the methods of S. M. Brombridge et al., *Synthetic Communications*, 1993, 23, 487-494. And compounds of formula (XI) can be prepared according to the methods of Igor V. Ukrainets et al., *Tetrahedron*, 1994, 50, 10331-10338.

Compounds of formula (VIII) wherein Y is $CR^3$, $L^1$ is OH and $R^1$ is hydrogen can be prepared by reacting a compound of formula (XII).

(XII)

wherein $G^1$, $R^5$ and n are as defined in formula (I), with a compound of formula (XIII)

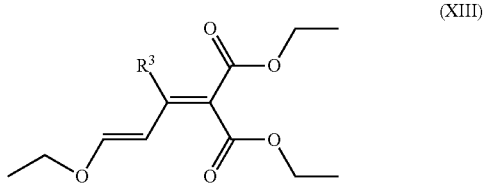
(XIII)

wherein $R^3$ is as defined in formula (I), at a suitable temperature, such as 160° C., followed by base promoted cyclisation and acid hydrolysis. Compounds of formula (XIII) can be prepared according to U.S. Pat. No. 3,838,155.

Compounds of formula (VIII) wherein Y is $CR^3$, $L^1$ is OH, $R^1$ is methyl and $R^3$ is hydrogen can be prepared by condensing a compound of formula (XIV).

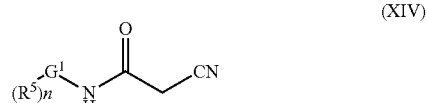
(XIV)

wherein $G^1$, $R^5$ and n are as defined in formula (I), with 4-methoxy-3-buten-2-one in the presence of a suitable base, such as 1,4-diazabicyclo[2.2.2]octane, at a suitable temperature in a suitable solvent such as diethyleneglycol monomethyl ether, followed by acid hydrolysis.

Salts of compounds of formula (I) may be formed by reacting the free base or a salt, enantiomer, tautomer or protected derivative thereof, with one or more equivalents of the appropriate acid. The reaction may be carried out in a solvent or medium in which the salt is insoluble, or in a solvent in which the salt is soluble followed by subsequent removal of the solvent in vacuo or by freeze drying. Suitable solvents include, for example, water, dioxane, ethanol, 2-propanol, tetrahydrofuran or diethyl ether, or mixtures thereof. The reaction may be a metathetical process or it may be carried out on an ion exchange resin.

Compounds of formula (I) and intermediate compounds thereto may be prepared as such or in protected form. The protection and deprotection of functional groups is, for example, described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

The compounds of the invention and intermediates may be isolated from their reaction mixtures, and if necessary further purified, by using standard techniques.

The compounds of formula (I) may exist in enantiomeric or diastereoisomeric forms or mixtures thereof, all of which are included within the scope of the invention. The various optical isomers may be isolated by separation of a racemic mixture of the compounds using conventional techniques, for example, fractional crystallisation or HPLC. Alternatively, the individual enantiomers may be made by reaction of the appropriate optically active starting materials under reaction conditions that will not cause racemisation.

Intermediate compounds may also exist in enantiomeric forms and may be used as purified enantiomers, diastereomers, racemates or mixtures thereof.

According to a further aspect of the invention we provide a compound of formula (I) or a pharmaceutically acceptable salt thereof, for use as a medicament.

The compounds of formula (I), and their pharmaceutically acceptable salts, are useful because they possess pharmacological activity in animals. The compounds of formula (I) have activity as pharmaceuticals, in particular as modulators of human neutrophil elastase and homologous serine proteases such as proteinase 3 and pancreatic elastase, and as such are predicted to be useful in therapy. The compounds of formula (I) are particularly useful as inhibitors of human neutrophil elastase. They may thus be used in the treatment or prophylaxis of inflammatory diseases and conditions.

Examples of these conditions are: adult respiratory distress syndrome (ARDS), cystic fibrosis, pulmonary emphysema, chronic obstructive pulmonary disease (COPD) and ischaemic-reperfusion injury. The compounds of this invention may also be useful in the modulation of endogenous and/or exogenous biological irritants which cause and/or propagate atherosclerosis, diabetes, myocardial infarction; hepatic disorders including but not limited to cirrhosis, systemic lupus erythematous, inflammatory disease of lymphoid origin, including but not limited to T lymphocytes, B lymphocytes, thymocytes; autoimmune diseases, bone marrow; inflammation of the joint (especially rheumatoid arthritis, osteoarthritis and gout); inflammation of the gastro-intestinal tract (especially inflammatory bowel disease, ulcerative colitis, pancreatitis and gastritis); inflammation of the skin (especially psoriasis, eczema, dermatitis); in tumour metastasis or invasion; in disease associated with uncontrolled degradation of the extracellular matrix such as osteoarthritis; in bone resorptive disease (such as osteoporosis and Paget's disease); diseases associated with aberrant angiogenesis; the enhanced collagen remodelling associated with diabetes, periodontal disease (such as gingivitis), corneal ulceration, ulceration of the skin, post-operative conditions (such as colonic anastomosis) and dermal wound healing; demyelinating diseases of the central and peripheral nervous systems (such as multiple sclerosis); age related illness such as dementia, inflammatory diseases of cardiovascular origins; granulomatous diseases; renal diseases including but not limited to nephritis and polyarteritis; cancer; pulmonary hypertension, ingested poisons, skin contacts, stings, bites; asthma; rhinitis; HIV disease progression; for minimising the effects of organ rejection in organ transplantation including but not limited to human organs; and replacement therapy of proteinase inhibitors.

Thus, another aspect of the invention provides the use of a compound of formula (I) or a pharmaceutically acceptable salt thereof, in the manufacture of a medicament for the treatment or prophylaxis of diseases or conditions in which inhibition of neutrophil elastase activity is beneficial; and a method of treating, or reducing the risk of, diseases or conditions in which inhibition of neutrophil elastase activity is beneficial which comprises administering to a person suffering from or at risk of, said disease or condition, a therapeutically effective amount of a compound of formula (I) or a pharmaceutically acceptable salt thereof.

In another aspect, the invention provides the use of a compound of formula (I) or a pharmaceutically acceptable salt thereof, in the manufacture of a medicament for the treatment or prophylaxis of inflammatory diseases or conditions; and a method of treating, or reducing the risk of, inflammatory diseases or conditions which comprises administering to a person suffering from or at risk of, said disease or condition, a therapeutically effective amount of a compound of formula (I) or a pharmaceutically acceptable salt thereof.

In particular, the compounds of this invention may be used in the treatment of adult respiratory distress syndrome (ARDS), cystic fibrosis, pulmonary emphysema, chronic obstructive pulmonary disease (COPD), pulmonary hypertension, asthma, rhinitis, ischemia-reperfusion injury, rheumatoid arthritis, osteoarthritis, cancer, atherosclerosis and gastric mucosal injury.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dose of the compound to be administered will depend on the compound employed, the disease being treated, the mode of administration, the age, weight and sex of the patient. Such factors may be determined by the attending physician. However, in general, satisfactory results are obtained when the compounds are administered to a human at a daily dosage of between 0.1 mg/kg to 100 mg/kg (measured as the active ingredient).

The compounds of formula (I) may be used on their own, or in the form of appropriate pharmaceutical formulations comprising the compound of the invention in combination with a pharmaceutically acceptable diluent, adjuvant or carrier. Particularly preferred are compositions not containing material capable of causing an adverse reaction, for example, an allergic reaction. Conventional procedures for the selection and preparation of suitable pharmaceutical formulations are described in, for example, "Pharmaceuticals—The Science of Dosage Form Designs", M. E. Aulton, Churchill Livingstone, 1988.

According to the invention, there is provided a pharmaceutical formulation comprising preferably less than 95% by weight and more preferably less than 50% by weight of a compound of formula (I) in admixture with a pharmaceutically acceptable diluent or carrier.

We also provide a method of preparation of such pharmaceutical formulations that comprises mixing the ingredients.

The compounds may be administered topically, for example, to the lungs and/or the airways, in the form of solutions, suspensions, HFA aerosols or dry powder formulations, for example, formulations in the inhaler device known as the Turbuhaler®; or systemically, for example, by oral administration in the form of tablets, pills, capsules, syrups, powders or granules; or by parenteral administration, for example, in the form of sterile parenteral solutions or suspensions; or by rectal administration, for example, in the form of suppositories.

Dry powder formulations and pressurized HFA aerosols of the compounds of the invention may be administered by oral or nasal inhalation. For inhalation, the compound is desirably finely divided. The finely divided compound preferably has a mass median diameter of less than 10 μm, and may be suspended in a propellant mixture with the assistance of a dispersant, such as a $C_8$-$C_{20}$ fatty acid or salt thereof, (for example, oleic acid), a bile salt, a phospholipid, an alkyl saccharide, a perfluorinated or polyethoxylated surfactant, or other pharmaceutically acceptable dispersant.

The compounds of the invention may also be administered by means of a dry powder inhaler. The inhaler may be a single or a multi dose inhaler, and may be a breath actuated dry powder inhaler.

One possibility is to mix the finely divided compound with a carrier substance, for example, a mono-, di- or polysaccharide, a sugar alcohol, or an other polyol. Suitable carriers are sugars, for example, lactose, glucose, raffinose, melezitose, lactitol, maltitol, trehalose, sucrose, mannitol; and starch. Alternatively the finely divided compound may be coated by another substance. The powder mixture may also be dispensed into hard gelatine capsules, each containing the desired dose of the active compound.

Another possibility is to process the finely divided powder into spheres which break up during the inhalation procedure. This spheronized powder may be filled into the drug reservoir of a multidose inhaler, for example, that known as the Turbuhaler® in which a dosing unit meters the desired dose which is then inhaled by the patient. With this system the active compound, with or without a carrier substance, is delivered to the patient.

For oral administration the active compound may be admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum, titanium dioxide, and the like. Alternatively, the tablet may be coated with a suitable polymer dissolved in a readily volatile organic solvent.

For the preparation of soft gelatine capsules, the compound may be admixed with, for example, a vegetable oil or polyethylene glycol. Hard gelatine capsules may contain granules of the compound using either the above mentioned excipients for tablets. Also liquid or semisolid formulations of the drug may be filled into hard gelatine capsules.

Liquid preparations for oral application may be in the form of syrups or suspensions, for example, solutions containing the compound, the balance being sugar and a mixture of ethanol, water, glycerol and propylene glycol. Optionally such liquid preparations may contain colouring agents, flavouring agents, saccharine and/or carboxymethylcellulose as a thickening agent or other excipients known to those skilled in art.

The compounds of the invention may also be administered in conjunction with other compounds used for the treatment of the above conditions.

The following Examples are intended to illustrate, but in no way limit the scope of the invention.

General Methods $^1$H NMR and $^{13}$C NMR spectra were recorded on a Varian Inova 400 MHz or a Varian Mercury-VX 300 MHz instrument. The central peaks of chloroform-d ($\delta_H$ 7.27 ppm), dimethylsulfoxide-$d_6$ ($\delta_H$ 2.50 ppm), acetonitrile-$d_3$ ($\delta_H$ 1.95 ppm) or methanol-$d_4$ ($\delta_H$ 3.31 ppm) were used as internal references. Column chromatography was carried out using silica gel (0.040-0.063 mm, Merck). Unless stated otherwise, starting materials were commercially available. All solvents and commercial reagents were of laboratory grade and were used as received.

The following abbreviations are used:
HBTU O-(Benzotriazol-1-yl)-N,N,N',N'-tetramethyluronium hexafluorophosphate;
HATU O-(7-Azabenzotriazol-1-yl)-N,N,N',N'-tetramethyluronium hexafluorophosphate;
HOBT 1-Hydroxybenzotriazole;
HOAT 1-Hydroxy-7-azabenzotriazole;
DIEA N,N-Diisopropylethylamine;
NMP 1-N-Methyl-2-pyrrolidinone;
DME 1,2-Dimethoxyethane;
THF Tetrahydrofuran;
TFA Trifluoroacetic acid;
DMF N,N-Dimethylformamide;
DCM Dichloromethane.

The following method was used for LC/MS analysis:
Instrument Agilent 1100; Column Waters Symmetry 2.1× 30 mm; Mass APCI; Flow rate 0.7 mL/min; Wavelength 254 nm; Solvent A: water+0.1% TFA; Solvent B: acetonitrile+ 0.1% TFA; Gradient 15-95%/B 8 min, 95% B 1 min.

Analytical chromatography was run on a Symmetry $C_{18}$-column, 2.1×30 mm with 3.5 μm particle size, with acetonitrile/water/0.1% trifluoroacetic acid as mobile phase in a gradient from 5% to 95% acetonitrile over 8 minutes at a flow of 0.7 ml/min.

EXAMPLE 1

6-Methyl-N-[4-(methylsulfonyl)benzyl]-2-oxo-5-phenyl-1-[3-(trifluoromethyl)phenyl]-1,2-dihydropyridine-3-carboxamide a) Ethyl 3-oxo-3-{[3-(trifluoromethyl) phenyl}amino]propanoate To an ice-cooled solution of 3-(trifluoromethyl)aniline (64.5 g, 0.40 mol) and triethylamine (60 ml) in acetone (700 ml) was added dropwise, ethyl 3-chloro-3-oxopropanoate (63.6 g, 0.42 mol) in acetone (50 ml). After the addition (approx. 30 minutes) stirring was continued at room temperature overnight. The solvents were removed and water (1200 ml) was added. The resulting precipitate was filtered off, thoroughly washed twice with water and then dried to afford the title compound as yellow powder (109 g, 99%).

$^1$H NMR (CDCl$_3$): δ 9.52 (1H, s); 7.87 (1H, s); 7.78 (1H, d); 7.46 (1H, t); 7.39 (1H, d); 4.29 (2H, q); 3.50 (2H, s); 1.35 (3H, t).

APCI-MS m/z: 276.1 [MH$^+$].

b) 6-Methyl-2-oxo-1-[3-(trifluoromethyl)phenyl]-1,2-dihydropyridine-3-carboxylic acid To a solution of ethyl 3-oxo-3-{[3-(trifluoromethyl)phenyl]amino}propanoate (19.2 g, 70 mmol) and sodium methoxide (7.6 g, 140 mmol) in EtOH (250 ml) was added 4-methoxybut-3-en-2-one (90%) (7.72 g, 77 mmol). After the addition, the reaction mixture was refluxed for 2 h and then cooled. Water (50 ml) and 2M NaOH were added and the mixture was stirred at room temperature overnight. The organic solvents were removed and the reaction mixture was extracted (washed) with EtOAc. The water phases were acidified with hydrochloric acid to pH 3-4, an orange coloured precipitate appeared and was filtered off, washed with water and dried. Recrystallisation twice from heptane/EtOAc (4:1) afforded the title compound (12 g, 58%) as a white powder.

$^1$H NMR (CDCl$_3$): δ 13.68 (1H, s); 8.54 (1H, d); 7.86 (1H, d); 7.79 (1H, t); 7.55 (1H, brs); 7.48 (1H, d); 6.58 (1H, d); 2.16 (3H, s).

APCI-MS m/z: 298.1 [MH$^+$].

c) 6-Methyl-N-[4-(methylsulfonyl)benzyl]-2-oxo-1-[3-(trifluoromethyl)phenyl]-1,2-dihydropyridine-3-carboxamide A mixture of 6-methyl-2-oxo-1-[3-(trifluoromethyl)phenyl]-1,2-dihydropyridine-3-carboxylic acid (7.43 g, 25 mmol), HATU (10.5 g, 27.5 mmol), HOAT (3.75 g, 27.5 mmol) and DIEA (14.2 ml, 82.5 mmol) in NMP (65 ml) was reacted for 1 h, then 4-methylsulphonylbenzyl amine hydrochloride (5.8 g, 26 mmol) was added. After 1 h, the reaction mixture was slowly poured into stirred ice water (1 L). A powder was formed, and the water mixture was acidified to pH 3 with citric acid (0.5 M), and stirring was continued for 1 h. The precipitate was filtered off, washed with water and dried in vacuum overnight. Recrystallisation from EtOAc gave 8.1 g (70%).

$^1$H NMR (CDCl$_3$): δ 10.00 (1H, brt); 8.60 (1H, d); 7.88 (2H, d); 7.83 (1H, d); 7.76 (1H, t); 7.53 (3H, m); 7.46 (1H, d); 6.49 (1H, d); 4.68 (2H, m); 3.03 (3H, s); 2.10 (3H, s).

APCI-MS m/z: 465.1 [MH$^+$].

d) 5-Iodo-6-methyl-N-[4-(methylsulfonyl)benzyl]-2-oxo-1-[3-(trifluoromethyl)phenyl]-1,2-dihydropyridine-3-carboxamide To a solution of 6-methyl-N-[4-(methylsulfonyl)benzyl]-2-oxo-1-[3-(trifluoromethyl)phenyl]-1,2-dihydropyridine-3-carboxamide (200 mg, 0.43 mmol) in MeCN (1.5 ml) at room temperature and under argon was added trifluoromethanesulfonic acid (1 ml) followed by N-iodosuccinimide (97 mg, 0.43 mmol). After 45 min, the reaction mixture was diluted with DCM, washed with aqueous NaHCO$_3$, with aqueous NaS$_2$O$_4$ and water, dried (Na$_2$SO$_4$), and evaporated to give the title compound (200 mg).

$^1$H NMR (CDCl$_3$): δ 9.85 (1H, brt); 8.90 (1H, d); 7.88 (2H, d); 7.76 (2H, m); 7.50 (2H, d); 7.48 (1H, s); 7.40 (1H, d); 4.65 (2H, m); 3.03 (3H, s); 2.32 (3H, s).

APCI-MS m/z: 591.0 [MH$^+$].

e) 6-Methyl-N-[4-(methylsulfonyl)benzyl]-2-oxo-5-phenyl-1-[3-(trifluoromethyl)phenyl]-1,2-dihydropyridine-3-carboxamide A mixture of phenylboronic acid (25 mg, 0.20 mmol), 1,1'-bis(diphenylphosphino)ferrocenedichloropalladium(II) (4 mg, 0.005 mmol), 5-iodo-6-methyl-N-[4-(methylsulfonyl)benzyl]-2-oxo-1-[3-(trifluoromethyl)phenyl]-1,2-dihydropyridine-3-carboxamide (100 mg 0.17 mmol), toluene (1 ml), ethanol (99%, 0.25 ml) and Na$_2$CO$_3$ (2M, 0.25 ml) was stirred at 80° C. overnight, concentrated and the residue was purified by flash chromatography to give the title compound (70 mg, 76%).

$^1$H NMR (CDCl$_3$): δ 10.04 (1H, brt); 8.64 (1H, s); 7.88 (2H, d); 7.82 (1H, d); 7.76 (1H, t); 7.58 (1H, s); 7.54-7.39 (6H, m); 7.31 (2H, d); 4.69 (2H, m); 3.02 (3H, s); 2.03 (3H, s).

APCI-MS m/z: 541 [MH$^+$].

EXAMPLE 2

5-Furan-3-yl-6-methyl-2-oxo-1-(3-trifluoromethylphenyl)-1,2-dihydro-pyridine-3-carboxylic acid 4-methanesulfonyl-benzylamide A mixture of 5-iodo-6-methyl-N-[4-(methylsulfonyl)benzyl]-2-oxo-1-[3-(trifluoromethyl)phenyl]-1,2-dihydropyridine-3-carboxamide (Example 1 (d), 0.0413 g, 0.07 mmol), furan-3-boronic acid (0.009 g, 0.08 mmol), Pd(PPh$_3$)$_4$ (0.004 g, 3.46 nmol), DME (2 ml) and Na$_2$CO$_3$ (2 ml, 2M) was vigorously stirred under nitrogen in a sealed vial at 80° C. for 2 h. Another portion of furan-3-boronic acid (0.005 g) and Pd(PPh$_3$)$_4$ (0.004 g) was added and the reaction was allowed to go for another hour. The mixture was allowed to cool, and was then partitioned between EtOAc and water. The organic phase was collected and the aqueous phase was extracted with another portion of EtOAc (10 ml). The combined organic phases were washed with water, brine, and dried over Na$_2$SO$_4$. Filtration and evaporation gave a crude oil which was purified on silica (heptane:EtOAc 2:1 to 1:1 to 1:2), which after evaporation of pure fractions gave 0.023 g (62%) of the title compound as a white solid.

$^1$H NMR (DMSO-d$_6$): δ 9.94 (1H, t, J 6.0 Hz); 8.36 (1H, s); 7.96-7.73 (7H, m); 7.54 (2H, d, J 8.14 Hz); 7.46 (1H, d, J 7.4 Hz); 6.73 (1H, s); 4.59 (2H, d, J 6.13 Hz); 3.17 (3H, s); 2.06 (3H, s).

APCI-MS m/z: 531.3 [MH$^+$].

Using the general method of Example 1, the compounds of Examples 3 to 6 were prepared:

EXAMPLE 3

5-[4-(Hydroxymethyl)phenyl]-6-methyl-N-[4-(methylsulfonyl)benzyl]-2-oxo-1-[3-(trifluoromethyl)phenyl]-1,2-dihydropyridine-3-carboxamide $^1$H NMR (CDCl$_3$): δ 10.04 (1H, brs); 8.64 (1H, brs); 7.88-7.77 (4H, m); 7.58-7.47 (6H, m); 7.32 (2H, brs); 4.78 (2H, s) 4.70 (2H, brs); 3.02 (3H, s); 2.03 (3H, s).

APCI-MS m/z: 571 [MH$^+$].

EXAMPLE 4

6'-Methoxy-2-methyl-N-[4-(methylsulfonyl)benzyl]-6-oxo-1-[3-(trifluoromethyl)phenyl]-1,6-dihydro-3,3'-bipyridine-5-carboxamide $^1$H NMR (CDCl$_3$): δ 10.00 (1H, t); 8.58 (1H, s); 8.12 (1H, d); 7.89-7.74 (4H, m); 7.58-7.49 (5H, m); 6.85 (1H, d); 4.69 (2H, m); 4.00 (3H, s); 3.02 (3H, s); 2.02 (3H, s).
APCI-MS m/z: 572[MH$^+$].

EXAMPLE 5

5-(2-Methoxypyrimidin-5-yl)-6-methyl-N-[4-(methylsulfonyl)benzyl]-2-oxo-1-[3-(trifluoromethyl)phenyl]-1,2-dihydropyridine-3-carboxamide $^1$H NMR (CDCl$_3$): δ 9.93 (1H, brt); 8.56 (1H, s); 8.51 (2H, s); 7.89-7.75 (4H, m); 7.57-7.48 (4H, m); 4.69 (2H., m); 4.09 (3H, s); 3.02 (3H, s); 2.02 (3H, s).
APCI-MS m/z: 573[MH$^+$].

EXAMPLE 6

5-[4-(Acetylamino)phenyl]-6-methyl-N-[4-(methylsulfonyl)benzyl]-2-oxo-1-[3-(trifluoromethyl)phenyl]-1,2-dihydropyridine-3-carboxamide $^1$H NMR (CDCl$_3$): δ10.05 (1H, brt); 8.61 (1H, s); 7.89-7.73 (4H, m); 7.61-7.49 (6H, m); 7.39 (1H, s); 7.24 (1H, s) 4.69 (2H, m); 3.02 (3H, s); 2.21 (3H, s); 2.02 (3H, s).
APCI-MS m/z: 598 [MH$^+$].

EXAMPLE 7

6-Methyl-2-oxo-5-(1H-pyrrol-3-yl)-1-(3-trifluoromethyl-phenyl)-1,2-dihydro-pyridine-3-carboxylic acid 4-methanesulfonyl-benzylamide A mixture of 5-iodo-6-methyl-N-[4-(methylsulfonyl)benzyl]-2-oxo-1-[3-(trifluoromethyl)phenyl]-1,2-dihydropyridine-3-carboxamide (0.060 g, 0.10 mmol), 1-trimethylsilyl-1H-pyrrol-3-yl-boronic acid (0.033 g, 0.12 mmol), Pd(PPh$_3$)$_4$ (0.005 g, 4.34 nmol), DME (2 ml) and Na$_2$CO$_3$ (2 ml, 2M) was vigorously stirred under nitrogen in a sealed vial at 80° C. for 2 h. Another portion of 1-trimethylsilyl-1H-pyrrol-3-yl-boronic acid (0.005 g) and Pd(PPh$_3$)$_4$ (0.004 g) was added and the reaction was allowed to go for another hour. The mixture was allowed to cool and partitioned between EtOAc and water. The organic phase was collected and the aqueous phase was extracted with another portion of EtOAc. The combined organic phases were washed with water and brine, and were then dried over Na$_2$SO$_4$. Filtration and evaporation gave a crude oil which was purified on silica (heptane:EtOAc 2:1 to 1:1 to 1:2), which after evaporation of pure fractions gave 0.08 g (80%) of the intermediate as a white solid. A solution of this solid in THF (10 ml) containing tetrabutylammonium-fluoride trihydrate (0.025 g, 0.08 mmol) was stirred at room temperature for 1 h. Evaporation and purification on silica (heptane EtOAc 2:1 to 1:1 to 1:2) provided 0.02 g (47%) of the title compound as a white solid, which darkened on standing.
$^1$H NMR (CDCl$_3$): δ10.12 (1H, t, J 5.5 Hz); 8.68 (1H, s); 8.53 (1H, bs); 7.86 (2H, d, J 8.3 Hz); 7.79 (1H, d, J 7.8 Hz); 7.73 (1H, t, J 7.8 Hz); 7.55 (1H, s); 7.52 (2H, d, J 8.3 Hz); 7.47 (1H, d, J 7.8 Hz); 6.87-6.82 (2H, m); 6.28-6.24 (1H, m); 4.74-4.60 (2H, m); 3.00 (3H, s); 2.14 (3H, s).
APCI-MS m/z: 530.1 [MH$^+$].

Using the general method of Example 2, the compounds of Example's 8 to 12 were prepared:

EXAMPLE 8

5-Furan-2-yl-6-methyl-2-oxo-1-(3-trifluoromethyl-phenyl)-1,2-dihydro-pyridine-3-carboxylic acid 4-methanesulfonyl-benzylamide $^1$H NMR (CDCl$_3$): δ 9.96 (1H, t, J 5.8 Hz); 8.85 (1H, s); 7.89 (2H, d, J 8.7 Hz); 7.84 (1H, d, J 7.7 Hz); 7.77 (1H, t, J 7.7 Hz) 7.56 (1H, s); 7.54 (2H, d, J 8.0 Hz); 7.48 (1H, d, J 7.7 Hz); 6.55-6.49 (2H, m); 4.76-4.64 (2H, m); 3.03 (3H, s); 2.23 (3H, s).
APCI-MS m/z: 531.1 [MH$^+$].

EXAMPLE 9

6-Methyl-2-oxo-5-thiophen-3-yl-1-(3-trifluoromethyl-phenyl)-1,2-dihydro-pyridine-3-carboxylic acid 4-methanesulfonyl-benzylamide $^1$H NMR (CDCl$_3$): δ 10.02 (1H, t, J 5.9 Hz); 8.65 (1H, s); 7.88 (2H, d, J 8.2 Hz); 7.82 (1H, d, J 7.8 Hz); 7.76 (1H, t, J 7.8 Hz); 7.57 (1H, s); 7.53 (2H, d, J 8.2 Hz); 7.49 (1H, d, J 7.8 Hz); 7.46-7.42 (1H, m); 7.27-7.25 (1H, m); 7.10 (1H, dd, J 5.0 Hz and 1.2 Hz); 4.75-4.62 (2H, m); 3.02 (3H, s); 2.07 (3H, s).
APCI-MS m/z: 547 [MH$^+$].

EXAMPLE 10

6-Methyl-2-oxo-5-thiophen-2-yl-1-(3-trifluoromethyl-phenyl)-1,2-dihydro-pyridine-3-carboxylic acid 4-methanesulfonyl-benzylamide $^1$H NMR (CDCl$_3$): δ 9.95 (1H, t, J 5.8 Hz); 8.68, (1H, s); 7.87 (2H, d, J 8.5 Hz); 7.83 (1H, d, J 7.8 Hz); 7.75 (1H, t, J 7.8 Hz); 7.56 (1H, s); 7.51 (2H, d, J 8.5 Hz); 7.48 (1H, d, J 8.5 Hz); 7.42-7.39 (1H, m); 7.12-7.08 (1H, m); 7.04-7.01 (1H, m); 4.74-4.62 (2H, m); 3.01 (3H, s); 2.11 (3H, s).
APCI-MS m/z: 547 [MH$^+$].

EXAMPLE 11

5-(3,5-Dimethyl-isoxazol-4-yl)-6-methyl-2-oxo-1-(3-trifluoromethyl-phenyl)-1,2-dihydro-pyridine-3-carboxylic acid 4-methanesulfonyl-benzylamide $^1$H NMR (CDCl$_3$): δ 9.93 (1H, t, J 5.8 Hz); 8.41 (1H, s); 7.86 (2H, d, J 8.7 Hz); 7.82 (1H, d, J 7.7 Hz); 7.76 (1H, t, J 7.7 Hz); 7.54 (1H, bs); 7.50 (2H, d, J 8.7 Hz); 7.49-7.44 (1H, m); 4.73-4.60 (2H, m); 3.01 (3H, s); 2.34-2.28 (3H, ds); 2.20-2.14 (3H, ds); 1.90 (3H, s).
APCI-MS m/z: 560.1 [MH$^+$].

EXAMPLE 12

5-(2,4-Dimethoxy-pyrimidin-5-yl)-6-methyl-2-oxo-1-(3-trifluoromethyl-phenyl)-1,2-dihydro-pyridine-3-carboxylic acid 4-methanesulfonyl-benzylamide $^1$H NMR (CDCl$_3$): δ 9.98 (1H, t, J 5.8 Hz); 8.49 (1H, s); 8.16 (1H, s); 7.87 (2H, d, J 8.8 Hz); 7.83 (1H, d, J 7.8 Hz); 7.76

(1H, t, J 7.7 Hz); 7.58 (1H, s); 7.52 (2H, d, J 8.2 Hz); 7.49 (1H, s); 4.76-4.60 (2H, m); 4.07 (3H, s); 4.02 (3H, s); 3.02 (3H, s); 1.91 (3H, s).
APCI-MS m/z: 603.1 [MH$^+$].

EXAMPLE 13

5-(2,4-Dioxo-1,2,3,4-tetrahydro-pyrimidin-5-yl)-6-methyl-2-oxo-1-(3-trifluoromethylphenyl)-1,2-dihydro-pyridine-3-carboxylic acid 4-methanesulfonyl-benzylamide A mixture of 5-iodo-6-methyl-N-[4-(methylsulfonyl)benzyl]-2-oxo-1-[3-(trifluoromethyl)phenyl]-1,2-dihydropyridine-3-carboxamide (0.075 g, 0.127 mmol), 2,4-di-tert-butyloxy-pyrimidine-5-boronic acid (0.044 g, 0.152 mmol), Pd(PPh$_3$)$_4$ (0.010 g, 8.69 nmol), DME (2 ml) and Na$_2$CO$_3$ (2 ml, 2M aqueous solution) was vigorously stirred under nitrogen in a sealed vial at 80° C. for 2 h. Then another portion of 2,4-di-tert-butyloxy-pyrimidine-5-boronic acid (0.010 g) and Pd(PPh$_3$)$_4$ (0.004 g) were added. After an additional hour the mixture was allowed to cool and was then partitioned between EtOAc and water. The organic phase was collected and the aqueous phase was extracted with another portion of EtOAc. The combined organic phases were washed with water and brine, and dried over Na$_2$SO$_4$. Filtration and evaporation followed by purification on silica (heptane:EtOAc 2:1 to 1:1 to 1:2) gave 0.060 g (69%) of the tert-butyl protected intermediate as a white solid. To a solution of the solid in THF (5 ml), TFA (5 ml) was added in one portion and the mixture was stirred for 30 minutes. The reaction mixture was concentrated and EtOAc was added to the residue. The obtained suspension was stirred for 10 minutes and the title compound was collected by filtration. Yield 0.045 g (100%) as an off-white solid.
$^1$H NMR (DMSO-d$_6$): δ 11.31 (1H, s); 11.13 (1H, d, J 6.0); 9.91 (1H, t, J 6.2 Hz); 8.24 (1H, s); 7.90 (1H, d, J 8.0 Hz); 7.86 (2H, d, J 8.4 Hz); 7.81 (1H, d, J 7.8 Hz); 7.70 (1H, d, J 7.6 Hz); 7.65-7.59 (1H, m); 7.53 (2H, d, J 8.4 Hz); 7.52 (1H, d, J 6.0 Hz); 4.58 (2H, d, J 6.2 Hz); 3.17 (3H, s); 1.91 (3H, s).
APCI-MS m/z: 575.1 [MH$^+$].

EXAMPLE 14

6-Methyl-5-(5-methyl-[1,3,4]oxadiazol-2-yl)-2-oxo-1-(3-trifluoromethyl-phenyl)-1,2-dihydro-pyridine-3-carboxylic acid 4-methanesulfonyl-benzylamide a) Ethyl 2-methyl-5-({[4-(methylsulfonyl)benzyl]amino}carbonyl)-6-oxo-1-[3-(trifluoromethyl)phenyl]-1,6-dihydropyridine-3-carboxylate In a stainless-steel autoclave (100 ml) were placed 5-iodo-6-methyl-N-[4-(methylsulfonyl)benzyl]-2-oxo-1-[3-(trifluoromethyl)phenyl]-1,2-dihydropyridine-3-carboxamide (108.1 mg, 0.18 mmol), palladium(II)acetate (3.8 mg, 0.02 mmol), triphenylphosphine (10.3 mg, 0.04 mmol), triethylamine (2 ml, 14.4 mmol) and ethanol (6 ml). The reaction mixture was magnetically stirred at 100° C. under a carbon monoxide pressure of 4 atmospheres overnight. After cooling, the solvent was evaporated off and the residue was purified by preparative HPLC to give the title compound as a white solid (77.6 mg, 79%).
$^1$H NMR (CDCl$_3$): δ 9.73 (1H, t, J 5.9 Hz); 9.20 (1H, s); 7.90 (2H, d, J 8.3 Hz); 7.85 (1H, d, J 7.9 Hz); 7.78 (1H, t, J 7.8 Hz); 7.53 (2H, d, J 8.3 Hz); 7.50 (1H, s); 7.42 (1H, d, J 8.0 Hz); 4.69 (2H, t, J 5.9 Hz); 4.38 (2H, q, J 7.2 Hz); 3.03 (3H, s); 2.50 (3H, s); 1.42 (3H, t, j 7.2 Hz).
APCI-MS m/z: 537 [MH$^+$].

b) 5-(4-Methanesulfonyl-benzylcarbamoyl)-2-methyl-6-oxo-1-(3-trifluoromethyl-phenyl)-1,6-dihydro-pyridine-3-carboxylic acid To a solution of ethyl 2-methyl-5-({[4-(methylsulfonyl)benzyl]amino}carbonyl)-6-oxo-1-[3-(trifluoromethyl)phenyl]-1,6-dihydropyridine-3-carboxylate (0.70 g, 1.30 mmol) in THF (10 ml) and water (10 ml) was added NaOH (1M, 2 ml, 2 mmol), and the mixture was stirred for 1 h at room temperature, monitoring the progress of the reaction by LC-MS. 20% conversion was observed and another portion of NaOH (1M, 1 ml, 1 mmol) was added, and the reaction was allowed to run for another hour. This process was repeated until complete conversion of the ester was observed (normally 3-4 hours). The outcome of the reaction is two compounds with the same mass, in a 95:5 proportion. The main product is the subtitle compound, and the other is a regioisomer. The reaction mixture was evaporated in order to remove TIM, and the residual water solution was acidified and then extracted into EtOAc. The organic phase was collected and dried over Na$_2$SO$_4$. Filtration and evaporation gave a crude product 0.60 g (90%) of a yellowish solid, which was used further without purification. A portion of the product was purified using preparative HPLC.
$^1$H NMR (CDCl$_3$): δ 9.90 (1H, t, J 6.2 Hz); 9.31 (1H, s); 7.89 (2H, d, J 8.2 Hz); 7.84 (1H, d, J 8.0 Hz); 7.77 (1H, t, J 8.0 Hz); 7.51 (2H, d, J 8.5 Hz); 4.49 (1H, s); 7.41 (1H, d, J 8.0 Hz); 4.92 (1H, bs); 4.78-4.63 (2H, m); 3.01 (3H, s); 2.53 (3H, s).
APCI-MS m/z: 509.2 [MH$^+$].

c) 5-(N$^1$-Acetyl-hydrazinocarbonyl)-6-methyl-2-oxo-1-(3-trifluoromethyl-phenyl)-1,2-dihydro-pyridine-3-carboxylic acid 4-methanesulfonyl-benzylamide A solution of 5-(4-methanesulfonyl-benzylcarbamoyl)-2-methyl-6-oxo-1-(3-trifluoromethyl-phenyl)-1,6-dihydro-pyridine-3-carboxylic acid (0.071 g, 0.14 mmol) in DCM (5 ml) containing SOCl$_2$ (5 ml) was stirred in a sealed flask for 2 h and then concentrated. The obtained solid in 1,4-dioxane (5 ml, dried over molecular sieves) and acetylhydrazide (0.1 g, 1.35 mmol) were stirred for 10 minutes and concentrated. The residue was purified by preparative HPLC giving 0.041 g (52%) of the title compound as a white solid.
$^1$H NMR (DMSO-d$_6$): δ 10.26 (1H, s); 9.95 (1H, s); 9.79 (1H, t, J 6.0 Hz); 8.50 (1H, s); 7.93 (1H, s); 7.93-7.90 (1H, m); 7.87 (2H, d, J 8.4 Hz); 7.82 (1H, d, J 7.7 Hz); 7.74 (1H, d, J 8.0 Hz); 7.55 (2H, d, J 8.3 Hz); 4.59 (2H, d, J 6.2 Hz); 3.17 (3H, s); 2.18 (3H, s); 1.91 (3H, s).
APCI-MS m/z: 565.2 [MH$^{30}$].

d) 6-Methyl-5-(5-methyl-[1,3,4]oxadiazol-2-yl)-2-oxo-1-(3-trifluoromethyl-phenyl)-1,2-dihydro-pyridine-3-carboxylic acid 4-methanesulfonyl-benzylamide 5-(N$^1$-Acetyl-hydrazinocarbonyl)-6-methyl-2-oxo-1-(3-trifluoromethyl-phenyl)-1,2-dihydro-pyridine-3-carboxylic acid 4-methanesulfonyl-benzylamide (0.03 g, 0.053 mmol) and TMS-polyphosphate as a solution in DCM (prepared as described in *Synthesis* 1982, page 591-592) (3 ml) were stirred in a sealed vial at 70° C. for 3 h. The cooled solution was diluted with DCM and washed with water. The organic phase was collected and the aqueous phase was extracted with another portion of DCM. The combined organic phase was washed with brine, dried (Na$_2$SO$_4$), filtered, and concentrated. The solid material was purified by preparative HPLC to give the title compound as a white solid (0.019 g, 66%).

$^1$H NMR (DMSO-d$_6$): δ 9.74 (1H, t, J 6.2 Hz); 8.78 (1H, s); 8.01 (1H, s); 7.94 (1H, d, J 7.8 Hz); 7.87 (2H, d; J 8.1 Hz); 7.82 (1H, t, J 7.7 Hz); 7.55 (2H, d, J 8.3 Hz); 4.61 (2H, d, J 6.1 Hz); 3.13 (3H, s); 2.59 (3H, s); 2.43 (3H, s).

APCI-MS m/z: 547.2 [MH$^+$].

Using the general method of Example 14, the compounds of Examples 15 to 19 were prepared:

EXAMPLE 15

6-Methyl-2-oxo-5-(5-propyl-[1,3,4]oxadiazol-2-yl)-1-(3-trifluoromethyl-phenyl)-1,2-dihydro-pyridine-3-carboxylic acid 4-methanesulfonyl-benzylamide $^1$H NMR (DMSO-d$_6$): δ 9.75 (1H, t, J 6.33 Hz); 8.78 (1H, s); 8.00 (1H, s); 7.94 (1H, d, J 8.1 Hz); 7.87 (2H, d, J 8.2 Hz); 7.86-7.83 (1H, m); 7.82 (1H, t, J 8.4 Hz); 7.55 (2H, d, J 8.4); 4.60 (2H, d, J 6.1 Hz); 3.17 (3H, s); 2.92 (2H, t, J 7.3 Hz); 2.42 (3H, s); 1.78 (2H, sext, J 7.3 Hz); 0.99 (3H, t, J 7.3 Hz).

APCI-MS m/z: 575.2 [MH$^+$].

EXAMPLE 16

{5-[5-(4-Methanesulfonyl-benzylcarbamoyl)-2-methyl-6-oxo-1-(3-trifluoromethyl-phenyl)-1,6-dihydro-pyridin-3-yl]-[1,3,4]oxadiazol-2-yl}-acetic acid ethyl ester $^1$H NMR (DMSO-d$_6$): δ 9.73 (1H, t, J 6.0 Hz); 8.77 (1H, s); 8.01 (1H, s); 7.94 (1H, d, J 7.8 Hz); 7.87 (2H, d, J 8.1 Hz); 7.86-7.80 (2H, m); 7.55 (2H, d, J 8.1); 4.61 (2H, d, J 6.3 Hz); 4.30 (2H, s); 4.17 (2H, q, J 7.2 Hz); 3.17 (3H, s); 2.44 (3H, s); 1.22 (3H, t, J 7.2 Hz).

APCI-MS m/z: 619.2 [MH$^+$].

EXAMPLE 17

5-(5-Cyanomethyl-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide $^1$H NMR (DMSO-d$_6$): δ 9.73 (1H, t, J 6.2 Hz); 8.76 (1H, s); 8.02 (1H, s); 7.94 (1H, d, J 7.6 Hz); 7.87 (2H, d, J 8.1 Hz); 7.86-7.80 (2H, m); 7.55 (2H, d, J 8.3 Hz); 4.70 (2H, s); 4.61 (2H, d, J 6.1 Hz); 3.17 (3H, s); 2.42 (3H, s).

APCI-MS m/z: 572.2 [MH$^+$].

EXAMPLE 18

5-(5-Amino-[1,3,4]oxadiazol-2-yl)-6-methyl-2-oxo-1-(3-trifluoromethyl-phenyl)-1)-1,2-dihydro-1-benzylamide $^1$H NMR (DMSO-d$_6$): δ 9.81 (1H, t, J 6.1 Hz); 8.71 (1H, s); 8.00 (1H, s); 7.94 (1H, d, J 8.0 Hz); 7.88 (2H, d, J 8.0 Hz); 7.86-7.82 (1H, m); 7.80 (1H, d, J 8.3 Hz); 7.56 (2H, d, J 8.2 Hz); 7.29 (2H, s); 4.62 (2H, 6.09 Hz); 3.18 (3H, s); 2.40 (3H, s).

APCI-MS m/z: 548.2 [MH$^+$].

EXAMPLE 19

5-(5-Amino-[1,3,4]thiadiazol-2-yl)-6-methyl-2-oxo-1-(3-trifluoromethyl-phenyl)-1,2-dihydro-pyridine-3-carboxylic acid 4-methanesulfonyl-benzylamide $^1$H NMR (DMSO-d$_6$): δ 9.83 (1H, t, J 6.2 Hz); 8.46 (1H, s); 7.99 (1H, s); 7.92 (1H, d, J 7.4 Hz); 7.87 (2H, d, J 8.2); 7.83 (1H, d, J 7.6 Hz); 7.79 (1H, d, J 8.0 Hz); 7.55 (2H, d, J 8.3 Hz); 7.42 (2H, s); 4.60 (2H, d, J 6.1 Hz); 3.17 (3H, s); 2.21 (3H, s).

APCI-MS m/z: 564.1 [MH$^+$].

EXAMPLE 20

5-(5-Ethylamino-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide a) 5-Hydrazinocarbonyl-6-methyl-2-oxo-1-(3-trifluoromethyl-phenyl)-1,2-dihydro-1-benzylamide The title compound was prepared as described in Examples 14 (c) and 38 (a).

APCI-MS m/z: 523.2 [MH$^+$]. Retention time 1.72 minutes.

b) 5-({2-[(Ethylamino)carbonyl]hydrazino}carbonyl)-6-methyl-N-[4-(methylsulfonyl)benzyl]-2-oxo-1-[3-(trifluoromethyl)phenyl]-1,2-dihydropyridine-3-carboxamide To 5-hydrazinocarbonyl-6-methyl-2-oxo-1-(3-trifluoromethyl-phenyl)-1,2-dihydro-pyridine-3-carboxylic acid 4-methanesulfonyl-benzylamide (0.030 g, 0.057 mmol) in 1,4-dioxane (10 ml) was added ethyl isocyanate (0.016 g, 0.23 mmol) and the mixture was stirred at room temperature for 1 h. The mixture was evaporated and the residue was purified by preparative HPLC giving 0.015 g (44%) of the title compound.

$^1$H NMR (CDCl$_3$): δ 9.96-9.87 (1H, m); 8.82 (1H, s); 7.88 (1H, d, J 8.2 Hz); 7.84 (2H, d, J 7.9 Hz); 7.83-7.80 (1H, m); 7.77 (1H, t, J 7.9 Hz); 7.52 (1H, s); 7.47 (2H, d, J 8.2 Hz); 7.47-7.41 (1H, m); 4.70-4.55 (2H, m); 3.23 (2H, q, J 6.8 Hz); 3.01 (3H, s); 2.31 (3H, s); 1.11 (3H, t, J 7.1 Hz).

APCI-MS m/z: 594.2 [MH$^+$].

c) 5-(5-Ethylamino-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide The title compound was prepared from 5-({2-[(ethylamino)carbonyl]hydrazino}carbonyl)-6-methyl-N-[4-(methylsulfonyl)benzyl]-2-oxo-1-[3-(trifluoromethyl)phenyl]-1,2-dihydropyridine-3-carboxamide using an analogous method to that described in Example 14 (d).

$^1$H NMR (DMSO-d$_6$): δ 9:78 (1H, t, J 6.0 Hz); 8.69 (1H, s); 7.99 (1H, s); 7.93 (1H, d, J 7.5 Hz); 7.87 (2H, d, J 8.5 Hz); 7.84 (1H, d, J 8.0 Hz); 7.81-7.75 (2H, m); 7.55 (2H, d, J 8.1 Hz); 4.60 (2H, d, J 6.1 Hz); 3.26 (2H, p, J 6.6 Hz); 3.17 (3H, s); 2.38 (3H, s); 1.18 (3H, t, J 7.1 Hz).

APCI-MS m/z: 576.3 [MH$^+$].

EXAMPLE 21

5-(5-N,N-Dimethylamino-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide a) 5-({2-[(N,N-Dimethylamino)carbonyl]hydrazino}-carbonyl)-6-methyl-N-[4-(methylsulfonyl)benzyl]-2-oxo-1-[3-(trifluoromethyl)phenyl]-1,2-dihydropyridine-3-carboxamide To 5-hydrazinocarbonyl-6-methyl-2-oxo-1-(3-trifluoromethyl-phenyl)-1,2-dihydro-pyridine-3-carboxylic acid 4-methanesulfonyl-benzylamide (0.030 g, 0.057 mmol) in THF (10 ml) was added N,N-dimethylcarbamoyl chloride (0.0247 g, 0.23 mmol) and the mixture was stirred at 50° C. for 3 h. The mixture was evaporated and the residue was purified by preparative HPLC giving 0.020 g (60%) of the title compound.
$^1$H NMR (DMSO-d$_6$): δ 9.92 (1H, bs); 9.80 (1H, t, 6.2 Hz); 8.50 (1H, s); 8.48 (1H, s); 7.94-7.89 (2H, m); 7.87 (2H, d, J 8.5 Hz); 7.82 (1H, d, J 8.2 Hz); 7.73 (1H, d, J 7.8 Hz); 7.55 (2H, d, J 8.5 Hz); 4.59 (2H, d, J 6.0 Hz); 3.17 (3H, s); 2.8 (6H, s); 2.19 (3H, s).
APCI-MS m/z: 594.1 [MH$^+$].

b) 5-(5-N,N-Dimethylamino-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide The title compound was prepared from 5-({2-[(N,N-dimethylamino)carbonyl]hydrazino}carbonyl)-6-methyl-N-[4-(methylsulfonyl)benzyl]-2-oxo-1-[3-(trifluoromethyl)phenyl]-1,2-dihydropyridine-3-carboxamide using the general method described in Example 14 (d).
$^1$H NMR (DMSO-d$_6$): δ 9.79 (1H, t, J 6.2 Hz); 8.69 (1H, s); 8.00 (1H, s); 7.93 (1H, d, J 7.9 Hz); 7.87 (2H, d, J 8.4 Hz); 7.85 (1H, t, J 7.7 Hz); 7.80 (1H, d, J 7.7 Hz); 7.55 (2H, d, J 8.4 Hz); 4.59 (2H, d, J 6.2 Hz); 3.17 (3H, s); 3.06 (6H, s); 2.36 (3H, s).
APCI-MS m/z: 576.3 [MH$^+$].

EXAMPLE 22

6-Methyl-N-[4-(methylsulfonyl)benzyl]-2-oxo-5-(pyrazin-2-yl)-1-[3-trifluoro-methyl)phenyl]-1,2-dihydropyridine-3-carboxamide Tris(dibenzylidene-acetone)dipalladium(0) (1 mg) was added to 5-iodo-6-methyl-N-[4-(methylsulfonyl)benzyl]-2-oxo-1-[3-(trifluoro-methyl)phenyl]-1,2-dihydropyridine-3-carboxamide (Example 1 (d), 20 mg, 0.034 mmol), 2-(tributylstannyl)pyrazine (25 mg, 0.068 mmol) and triphenylphosphine (1.6 mg, 0.006 mmol) in toluene (1.5 ml) under argon and the mixture was stirred in a sealed vial at 100° C. overnight. After cooling, the mixture was filtered through celite and evaporated. The residue was dissolved in toluene and ether was added. The precipitate was filtered off and dried in vacuo (5 mg, 27%).
$^1$H NMR (CDCl$_3$): δ 9.93-9.85 (1H, m); 8.82-8.77 (2H, m); 8.68-8.64 (1H, m); 8.60 (1H, d, J 14.0 Hz); 7.91-7.73 (4H, m); 7.59-7.46 (4H, m); 4.76-4.62 (2H, m); 3.01 (3H, s); 2.18 (3H, s).
APCI-MS m/z 543.3 [MH$^+$].

EXAMPLE 23

6-Methyl-5-(oxazol-2-yl)-2-oxo-1-(3-trifluoromethyl-phenyl)-1,2-dihydro-pyridine-3-carboxylic acid 4-methanesulfonyl-benzylamide 5-Iodo-6-methyl-N-[4-(methylsulfonyl)benzyl]-2-oxo-1-[3-(trifluoro-methyl)phenyl]-1,2-dihydropyridine-3-carboxamide (0.10 g, 0.169 mmol), 2-tributylstannyl-oxazole (0.12 g, 0.33 mmol, prepared according to literature procedures), Pd(PPh$_3$)$_4$ (0.015 g, 0.012 mmol) and dimethoxyethane (DME, 2.5 ml) and a magnetic stirrer bar were placed in a vial. The suspension was degassed and the vial sealed, and subsequently heated (100° C.) with stirring for 4 h. LC-MS confirmed the conversion of the iodide to the desired product, and the solvents were removed in vacuo. Purification on preparative HPLC afforded the title compound (0.06 g, 67%) as a white solid after freeze-drying the pure fractions.
$^1$H NMR (DMSO-d$_6$): δ 9.79 (1H, t, J 6.2 Hz); 8.91 (1H, s); 8.28 (1H, s); 7.99 (1H, s); 7.93 (1H, d, J 7.9 Hz); 7.87 (2H, d, J 8.2 Hz); 7.85 (1H, t, J 7.9 Hz); 7.80 (1H, d, J 7.8 Hz); 7.55 (2H, d, J 8.2 Hz); 7.42 (1H, s); 4.67-4.55 (2H, m); 3.17 (3H, s); 2.46 (3H, s).
APCI-MS m/z: 532.2 [MH$^+$].

EXAMPLE 25

6-Methyl-5-(1-methyl-1H-imidazol-2-yl)-2-oxo-1-(3-trifluoromethyl-phenyl)-1,2-dihydro-pyridine-3-carboxylic acid 4-methanesulfonyl-benzylamide 5-Iodo-6-methyl-N-[4-(methylsulfonyl)benzyl]-2-oxo-1-[3-(trifluoro-methyl)phenyl]-1,2-dihydropyridine-3-carboxamide (0.06 g, 0.1 mmol), 1-methyl-2-tributylstannyl-1H-imidazole (0.11 g, 0.5 mmol, prepared according to literature procedures), Pd(PPh$_3$)$_4$ (0.015 g, 0.012 mmol), DME (2 ml) and a magnetic stirrer bar were placed in a vial. The suspension was degassed and the vial was sealed, and subsequently heated (100° C.) with stirring overnight. LC-MS confirmed the conversion of the iodide to the desired product, and the solvents were removed in vacuo. Purification on preparative HPLC afforded the title compound (0.005 g, 10%) as a white solid after freeze-drying the pure fractions.
$^1$H NMR (DMSO-d$_6$): δ 9.88 (1H, t, J 6.2 Hz); 8.30 (1H, s); 8.03 (1H, s); 7.94-7.89 (1H, m); 7.87 (2H, d, J 8.5 Hz); 7.85-7.81 (2H, m); 7.55 (2H, d, J 8.5 Hz); 7.31 (1H, s); 7.06 (1H, s); 4.66-4.55 (2H, m); 3.58 (3H, s); 3.17 (3H, s); 1.85 (3H, s).
APCI-MS m/z: 545.2 [MH$^+$].

EXAMPLE 26

6-Methyl-2-oxo-5-(1H-pyrazol-4-yl)-1-(3-trifluoromethyl-phenyl)-1,2-dihydro-pyridine-3-carboxylic acid 4-methanesulfonyl-benzylamide 5-Iodo-6-methyl-N-[4-(methylsulfonyl)benzyl]-2-oxo-1-[3-(trifluoromethyl)-phenyl]-1,2-dihydropyridine-3-carboxamide (0.080 g, 0.135 mmol), 4-tributylstannyl-1-trityl-1H-pyrazole (0.08 g, 0.13 mmol, prepared according to literature procedures), Pd(PPh$_3$)$_4$ (0.020 g, 0.017 mmol), DME (3 ml) and a magnetic stirrer bar were placed in a vial. The reactor was degassed, the vial sealed and the reaction was heated (95° C.) with stirring overnight. LC-MS showed that almost all starting iodide had been consumed to give a main product. The crude mixture was evaporated and the residual oil was purified on silica (heptane:EtOAc 1:2), giving 0.060 g of the intermediate trityl protected product. The intermediate was dissolved in DCM (3 ml) and TFA (3 ml) was added. The mixture was heated (50° C.) with stirring for 30 minutes. The reaction was quenched by the addition of methanol (5 ml). Purification on preparative HPLC gave the title compound (0.016 g, 22%) as a white solid after freeze-drying the pure fractions.

$^1$H NMR (DMSO-$d_6$): δ 9.98 (1H, t, J 6.2 Hz); 8.38 (1H, s); 7.94 (1H, s); 7.91 (1H, d, J 8.1 Hz); 7.87 (2H, d, J 8.3 Hz); 7.84-7.80 (2H, m); 7.75 (1H, d, J 7.9 Hz); 7.55 (2H, d, J 8.4 Hz); 5.76 (1H, s); 4.64-4.55 (2H, m); 3.17 (3H, s); 2.06 (3H, s).

APCI-MS m/z: 531.1 [MH$^+$].

EXAMPLE 27

6-Methyl-N-[4-(methylsulfonyl)benzyl]-2-oxo-5-pyrimidin-2-yl-1-[3-(trifluoro-methyl)phenyl]-1,2-dihydropyridine-3-carboxamide Tris(dibenzylideneacetone)-dipalladium(0) (1 mg) was added to 5-iodo-6-methyl-N-[4-(methylsulfonyl)benzyl]-2-oxo-1-[3-(trifluoromethyl)-phenyl]-1,2-dihydropyridine-3-carboxamide (20 mg, 0.034 mmol), 2-(tributyl-stannyl)pyrimidine (25 mg, 0.068 mmol) and triphenylphosphine (1.9 mg, 0.007 mmol) in toluene (1.6 ml) under argon and the mixture was stirred at 100° C. overnight. After cooling, the mixture was filtered through celite and evaporated. The residue was purified by preparative HPLC. Pure fractions were freeze-dried to give the title compound (5 mg, 27%).

$^1$H NMR (CDCl$_3$): δ 9.91-9.85 (1H, m); 9.28 (1H, s); 8.84 (2H, d, 15.2 Hz); 7.90-7.73 (4H, m); 7.57-7.45 (4H, m); 7.29-7.25 (1H, m); 4.76-4.62 (2H, m); 3.01 (3H, s); 2.40 (3H, s).

APCI-MS m/z: 543.1 [MH$^+$].

EXAMPLE 28

6-Methyl-5-(2-methyl-2H-pyrazol-3-yl)-2-oxo-1-(trifluoromethyl-phenyl)-1,2-dihydro-pyridine-3-carboxylic acid 4-methanesulfonyl-benzylamide 5-Iodo-6-methyl-N-[4-(methylsulfonyl)benzyl]-2-oxo-1-[3-(trifluoromethyl)-phenyl]-1,2-dihydropyridine-3-carboxamide (0.06 g, 0.1 mmol), 1-methyl-5-trimethylstannyl-1H-pyrazole (0.07 g, 0.3 mmol, prepared according to literature procedures), Pd(PPh$_3$)$_4$ (0.015 g, 0.012 mmol), DME (2 ml) and a magnetic stirrer bar were placed in a vial. The suspension was degassed and the vial was sealed, and subsequently heated (100° C.) with stirring overnight. LC-MS confirmed the conversion of the iodide to the desired product, and the solvents were removed in vacuo. Purification on silica (heptane:EtOAc 1:2 to 1:3) afforded the title compound (0.040 g, 75%) as a white solid, which was subsequently freeze-dried.

$^1$H NMR (DMSO-$d_6$): δ 9.89 (1H, t, J 6.2 Hz); 8.21 (1H, s); 8.02 (1H, s); 7.92 (1H, d, J 7.31 Hz); 7.87 (2H, d, 18.3 Hz); 7.85-7.80 (2H, m); 7.54 (2H, d, J 8.3 Hz); 7.53 (1H, d, J 1.8 Hz); 6.33 (1H, d, J 1.8 Hz); 4.66-4.55 (2H, m); 3.72 (3H, s); 3.17 (3H, s); 1.82 (3H, s).

APCI-MS m/z: 545.2 [MH$^+$].

EXAMPLE 29

6-Methyl-5-(3-methylisoxazol-4-yl)-N-[4-(methylsulfonyl)benzyl]-2-oxo-1-[3-(trifluoromethyl)phenyl]-1,2-dihydropyridine-3-carboxamide 5-Iodo-6-methyl-N-[4-(methylsulfonyl)benzyl]-2-oxo-1-[3-(trifluoromethyl)phenyl]-1,2-dihydropyridine-3-carboxamide (25 mg, 0.042 mmol), tetrakis(triphenylphosphine) palladium (2.5 mg, 0.0022 mmol) and 3-methyl-4-(tributylstannyl)isoxazole [synthesized as described by D. Uchiyama in Heterocycles, 43, 6, 1301, 1996] (32 mg, 0.086 mmol) were mixed in DME (0.45 ml) in an argon filled vial. The vial was closed and heated with stirring at 100° C. for 24 h. The reaction mixture was poured into a mixture of ethyl acetate and water. The mixture was shaken, the water phase was removed and the organic phase was dried over sodium sulphate. The product was purified by preparative HPLC. Yield: 12 mg, 0.022 mmol (52%).

$^1$H NMR (DMSO-$d_6$): δ 9.91 (1H, t, J 6.0 Hz); 8.24 (1H, s); 8.96 (1H, s); 7.98-7.77 (6H, m); 7.54 (2H, d, J 8.4 Hz); 4.59 (2H, d, J 6.2 Hz); 3.17 (3H, s); 2.21 (3H, s); 1.88 (3H, s).

APCI-MS m/z: 546.5 [MH$^+$].

EXAMPLE 30

6-Methyl-5-(3-methyl-[1,2,4]oxadiazol-5-yl)-2-oxo-1-(3-trifluoromethyl-phenyl)-1,2-dihydro-pyridine-3-carboxylic acid 4-methanesulfonyl-benzylamide 5-Iodo-6-methyl-N-[4-(methylsulfonyl)benzyl]-2-oxo-1-[3-(trifluoromethyl)phenyl]-1,2-dihydropyridine-3-carboxamide (0.236 g, 0.4 mmol), acetamide oxime (0.088 g, 1.2 mmol), Pd(PPh$_3$)$_2$Cl$_2$ (0.014 g, 0.020 mmol), triethylamine (0.081 g, 0.8 mmol), toluene (15 ml) and a magnetic stirrer bar were loaded into a pressure safe steel reactor. The reactor was degassed with CO, and when all air had been removed, a 4 atmospheres pressure of CO was applied, and the reactor was heated to 95° C. The reaction was allowed to proceed overnight. LC-MS showed that almost all starting iodide had been consumed to give a main product. The crude mixture was evaporated and the residual oil was partitioned between EtOAc and water. The organic phase was collected, and was dried and evaporated. Purification on silica (heptane:EtOAc 1:2) gave pure material (0.083 g, 38%) as a white solid.

$^1$H NMR (DMSO-$d_6$): δ 9.68 (1H, t, J 6.2 Hz); 8.91 (1H, s); 8.01 (1H, s); 7.95 (1H, d, J 8.1 Hz); 7.87 (2H, d, J 8.02 Hz); 7.86 (1H, t, J 7.16 Hz); 7.81 (1H, d, J 7.86 Hz); 7.55 (2H, d, J 8.3 Hz); 4.67-4.55 (2H, m); 3.17 (3H, s); 2.47 (3H, s); 2.41 (3H, s).

APCI-MS m/z: 547.0 [MH$^+$].

EXAMPLE 31

6-Methyl-5-(3-methylisoxazol-5-yl)-N-[4-(methylsulfonyl)benzyl]-2-oxo-1-[3-(trifluoromethyl)phenyl]-1,2-dihydropyridine-3-carboxamide The title compound was synthesized in the same way as Example 29 but starting from 5-iodo-6-methyl-N-[4-(methylsulfonyl)benzyl]-2-oxo-1-[3-(trifluoromethyl)phenyl]-1,2-dihydropyridine-3-carboxamide (50 mg, 0.085 mmol), tetrakis(triphenylphosphine)palladium (5 mg, 0.0043 mmol) and 3-methyl-5-(tributylstannyl)isoxazole [synthesized as described in Tetrahedron, 47, 28, 5111, 1991] (63 mg, 0.169 mmol) in DME (0.85 ml). Yield: 15 mg, 0.033 mmol (39%).

¹H NMR (DMSO-d₆): δ 9.79 (1H, t, J=6.0 Hz); 8.57 (1H, s); 7.99 (1H, s); 7.94-7.79 (5H, m); 7.55 (2H, d, J=8.4 Hz); 6.67 (1H, s); 4.60 (2H, d, J=6.2 Hz); 3.17 (3H, s); 2.30 (3H, s); 2.17 (3H, s).

APCI-MS m/z: 546.4 [MH⁺].

The compounds of Examples 32 to 37 were prepared using analogous methods to those described in Examples 1 (a) to 1 (d) and 2.

EXAMPLE 32

5-(3,5-Dimethylisoxazol-4-yl)-N-[4-(isopropylsulfonyl)benzyl]-6-methyl-2-oxo-1-[3-(trifluoromethyl)phenyl]-1,2-dihydropyridine-3-carboxamide ¹H NMR (CDCl₃): δ 10.12 (1H, bt); 8.44 (1H, s); 7.86-7.67 (4H, m); 7.56 (1H, bs); 7.51-7.47 (3H, m); 4.76-4.66 (2H, m); 3.21-3.11 (1H, m); 2.34 (3H, d, J 6.8 Hz); 2.20 (3H, d, J 6.8 Hz); 1.93 (3H, s): 1.27 (6H; d, J 7.0 Hz).

APCI-MS m/z: 588 [MH⁺].

EXAMPLE 33

5-(3,5-Dimethylisoxazol-4-yl)-N-[4-(ethylsulfonyl)benzyl]-6-methyl-2-oxo-1-[3-(trifluoromethyl)phenyl]-1,2-dihydropyridine-3-carboxamide ¹H NMR (CDCl₃): δ 10.15 (1H, bt); 8.43 (1H, s); 7.86-7.83 (3H, m); 7.78 (1H, bt); 7.57 (1H, bs) 7.53-7.47 (3H, m); 4.73-4.69 (2H, m); 3.09 (2H, q, J 7.4 Hz); 2.34 (3H, d, J 6.9 Hz); 2.20 (3H, d, J 6.9 Hz); 1.94 (3H, s): 1.26 (3H, t, J 7.4 Hz).

APCI-MS m/z: 574 [MH⁺].

EXAMPLE 34

N-[4-(Cyclopropylsulfonyl)benzyl]-5-(3,5-dimethylisoxazol-4-yl)-6-methyl-2-oxo-1-[3-(trifluoromethyl)phenyl]-1,2-dihydropyridine-3-carboxamide ¹H NMR (CDCl₃): δ 10.06 (1H, bt); 8.43 (1H, s); 7.88-7.76 (4H, m); 7.56 (1H, bs) 7.51-7.47 (3H, m); 4.74-4.63 (2H, m);); 2.45-2.38 (1H, m); 2.33 (3H, d, J 6.7 Hz); 2.19 (3H, d, J 6.7 Hz); 1.92 (3H, s): 1.35-1.30 (2H, m); 1.07-0.99 (2H, m).

APCI-MS m/z: 586 [MH⁺].

EXAMPLE 35

1-(3-Cyanophenyl)-5-(3,5-dimethylisoxazol-4-yl)-6-methyl-N-[4-(methylsulfonyl)benzyl]-2-oxo-1,2-dihydropyridine-3-carboxamide ¹H NMR (CDCl₃): δ 9.88 (1H, bt); 8.44 (1H, s); 7.90-7.86 (3H, m); 7.77 (1H, bt); 7.62-7.51 (4H, m); 4.74-4.63 (2H, m); 3.02 (3H, s); 2.33 (3H, d, J 5.7 Hz); 2.19 (3H, d, J 5.6 Hz); 1.93 (3H, s).

APCI-MS m/z: 517 [MH⁺].

EXAMPLE 36

1-(3-Chlorophenyl)-5-(3,5-dimethyl-isoxazol-4-yl)-6-methyl-2-oxo-1,2-dihydro-pyridine-3-carboxylic acid 4-methanesulfonyl-benzylamide ¹H NMR (CDCl₃): δ 9.98 (1H, bt); 8.42 (1H, s); 7.88 (2H, d, J 8.4 Hz); 7.57-7.52 (4H, m); 7.30-7.29 (1H, m); 7.19-7.17 (1H, m); 4.68 (2H, d, J 5.6 Hz); 3.02 (3H, s); 2.32 (3H, d, J 4.0 Hz); 2.18 (3H, d, J 4.2 Hz); 1.95 (3H, s).

APCI-MS m/z: 526 [MH⁺].

EXAMPLE 37

5-(3,5-Dimethyl-isoxazol-4-yl)-6-methyl-2-oxo-1-m-tolyl-1,2-dihydro-pyridine-3-carboxylic acid 4-methanesulfonyl-benzylamide ¹H NMR (CDCl₃): δ 10.11 (1H, bt); 8.40 (1H, s); 7.87 (2H, d, J 8.4 Hz); 7.54-7.47 (3H, m); 7.35 (1H, d, J 7.7 Hz); 7.06-7.03 (2H, m); 4.67 (2H, d, J 5.9 Hz); 3.02 (3H, s); 2.46 (3H, s); 2.32 (3H, d, J 2.5 Hz); 2.18 (3H, d, J 3.0 Hz); 1.93 (3H, s).

APCI-MS m/z: 506 [MH⁺].

EXAMPLE 38

5-(5-Isopropyl-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide a) 5-Hydrazinocarbonyl-6-methyl-2-oxo-1-(3-trifluoromethyl-phenyl)-1,2-dihydro-pyridine-3-carboxylic acid 4-methanesulfonyl-benzylamide The compound obtained in Example 14 (b) (0.051 g, 0.14 mmol) in DCM (5 ml) was treated with SOCl₂ (5 ml), and the flask was sealed and stirred magnetically for 2 h, when LC-MS showed that the reaction was complete. The crude mixture was evaporated in vacuo, giving the intermediate acid chloride as a yellow solid. The solid was dissolved in 1,4-dioxane (5 ml, dried over molecular sieves) and hydrazine hydrate (0.05 g, 1.0 mmol) was added. The mixture was stirred for 10 minutes, and LC-MS showed complete formation of the title compound. The mixture was concentrated in vacuo and the residue was purified by preparative HPLC giving the title compound (0.036 g, 70%) as a white solid after freeze-drying the pure fractions.

APCI-MS m/z: 523.2 [MH⁺].

b) 5-(N¹-Isobutyryl-hydrazinocarbonyl)-6-methyl-2-oxo-1-(3-trifluoromethyl-phenyl)-1,2-dihydro-pyridine-3-carboxylic acid 4-methanesulfonyl-benzylamide The compound obtained in step (a) (0.025 g, 0.047 mmol) in dry THF (10 ml) was stirred and isobutyric anhydride (0.040 g, 0.25 mmol) was added. The obtained mixture was stirred for 15 minutes, and LC-MS showed complete conversion of the starting material to the desired amide. The solvent was evaporated and the residue was purified by preparative HPLC giving the subtitle compound (0.024 g, 85%) as a white powder after freeze-drying the pure fractions.

¹H NMR (DMSO-d₆): δ 10.25 (1H, bs); 9.89 (1H, bs); 9.79 (1H, t, J 6.2 Hz); 8.50 (1H, s); 7.53 (1H, s); 7.94-7.90 (1H, m); 7.87 (2H, d, J 8.5 Hz); 7.84 (1H, t, J 7.7 Hz); 7.74 (1H, d, J 7.7 Hz); 7.55 (2H, d, J 8.3 Hz); 4.63-4.56 (2H, m); 3.18 (3H, s); 2.55-2.49 (1H, p, J 6.8 Hz); 2.18 (3H, s); 1.08 (6H, d, J 6.8 Hz).

APCI-MS m/z: 593.2 [MH⁺].

c) 5-(5-Isopropyl-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide The compound obtained in step (b) (0.02 g, 0.034 mmol) in TMS-polyphosphate (3 ml, PPSE in DCM, *Synthesis* 1982, page 591-592) was stirred in a sealed vial and heated at 70° C. for 3 h. LC-MS showed complete conversion of the linear starting material to a compound with the expected MW. The cooled solution was diluted with DCM (10 ml) and was washed with water (10 ml). The organic phase was collected and the aqueous phase was extracted with another portion of DCM (10 ml). The combined organic phase was washed with brine and was then dried with $Na_2SO_4$. Filtration and evaporation of the solution gave a white solid. Purification of this material by preparative HPLC provided pure fractions which were freeze-dried. The title compound was obtained as a white solid (0.015 g, 77%).

$^1$H NMR (DMSO-$d_6$): δ 9.76 (1H, t, J 6.29 Hz); 8.77 (1H, s); 8.01 (1H, s); 7.94 (1H, d, J 7.6 Hz); 7.87 (2H, d, J 8.6 Hz); 7.84-7.78 (2H, m); 7.55 (2H, d, J 8.4 Hz); 4.65-4.56 (2H, m); 3.30 (1H, p, J 6.9 Hz); 3.18 (3H, s); 2.41 (3H, s); 1.36 (6H, d, J 7.0 Hz).

APCI-MS Mk: 575.2 [MH$^+$].

EXAMPLE 39

6-Methyl-5-[1,3,4]oxadiazol-2-yl)-2-oxo-1-(3-trifluoromethyl-phenyl)-1,2-dihydro-pyridine-3-carboxylic acid 4-methanesulfonyl-benzylamide a) 5-[N$^1$-(Formyl-hydrazinocarbonyl]-6-methyl-2-oxo-1-(3-trifluoromethyl-phenyl)-1,2-dihydro-pyridine-3-carboxylic acid 4-methanesulfonyl-benzylamide The compound obtained in Example 38 (a) (0.025 g, 0.048 mmol) in dry THF (10 ml) was stirred and mixed formylacetyl anhydride (0.06 g, 0.68 mmol; prepared according to literature procedures) was added. The mixture was stirred for 20 minutes and LC-MS showed full conversion of the starting material. Evaporation and purification on preparative HPLC, and subsequent freeze-drying, afforded the sub-title compound (0.022 g, 83%) as a white powder.

$^1$H NMR (DMSO-$d_6$): δ 10.43 (1H, s); 10.13 (1H, s); 9.79 (1H, t, J 6.2 Hz); 8.52 (1H, s); 8.11 (1H, s); 7.93 (1H, s); 7.94-7.89 (1H, s); 7.87 (2H, d, J 8.65 Hz); 7.87 (1H, d, J 8.21); 7.74 (1H, d, J 8.21 Hz); 7.55 (2H, d, J 8.21 Hz); 4.63-4.54 (2H, m); 3.17 (3H, s); 2.18 (3H, s).

APCI-MS m/z: 551.2 [MH$^+$].

b) 6-Methyl-5-[1,3,4]oxadiazol-2-yl)-2-oxo-1-(3-trifluoromethyl-phenyl)-1,2-dihydro-pyridine-3-carboxylic acid 4-methanesulfonyl-benzylamide The title compound was prepared according to the procedure described in Example 38 (c) starting from 0.020 g (0.036 mmol) of the compound obtained in step (a). The title compound was obtained as a white solid (0.010 g, 52%) after purification on preparative HPLC and freeze-drying of the pure fractions.

$^1$H NMR (DMSO-$d_6$): δ 9.74 (1H, t, J 6.3 Hz); 9.38 (1H, s); 8.82 (1H, s); 8.01 (1H, s); 7.94 (1H, d, J 7.7 Hz); 7.87 (2H, d, J 8.0 Hz); 7.87-7.84 (1H, m); 7.81 (1H, d, J 7.9 Hz); 7.55 (2H, d, J 8.0 Hz); 4.65-4.55 (2H, m); 3.17 (3H, s); 2.45 (3H, s).

APCI-MS m/z: 533.2 [MH$^+$].

EXAMPLE 40

5-(5-Hydroxy-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide a) N$^1$-[5-(4-Methanesulfonyl-benzylcarbamoyl)-2-methyl-6-oxo-1-(3-trifluoromethyl-phenyl)-1,6-dihydro-pyridine-3-carbonyl]-hydrazinecarboxylic acid ethyl ester The compound obtained in Example 38 (a) (0.025 g, 0.048 mmol) in dry THF (2 ml) was stirred and diethyl pyrocarbonate (0.023 g, 0.14 mmol) was added. The vial was sealed and was stirred at 40° C. for 3 h, monitoring the reaction by LC-MS. The mixture was evaporated and was then purified by preparative HPLC, giving the sub-title compound (0.023 g, 80%) as a white solid after freeze-drying the pure fractions.

$^1$H NMR (DMSO-$d_6$): δ 10.23 (1H, s); 9.79 (1H, t, J 6.1 Hz); 9.23 (1H, s); 8.47 (1H, s); 7.94 (1H, s); 7.94-7.89 (1H, d, J 8.2 Hz); 7.87 (2H, d, J 8.4 Hz); 7.82 (1H, d, J 7.7 Hz); 7.74 (1H, d, J 7.8 Hz); 7.54 (2H, d, J 8.4 Hz); 4.65-4.55 (2H, m); 4.14-4.01 (2H, m); 3.17 (3H, s); 2.16 (3H, s); 1.25-1.15 (3H, m).

APCI-MS m/z: 595.2 [MH$^+$].

b) 5-(5-Hydroxy-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide The title compound was prepared according to the procedure described in Example 38 (c) starting from 0.015 g (0.025 mmol) of the compound obtained in step (a). The reaction time was 4 days. The product was obtained as a white solid (0.008 g, 58%) after purification on preparative HPLC and freeze-drying of the pure fractions.

$^1$H NMR (DMSO-$d_6$): δ 12.61 (1H, bs); 9.73 (1H, t, J 6.2 Hz); 8.63 (1H, s); 7.99 (1H, s); 7.93 (1H, d, J 8.0 Hz); 7.87 (2H, d, J 8.2 Hz); 7.85 (1H, t, J 7.8 Hz); 7.78 (1H, d, J 7.8 Hz); 7.55 (2H, d, J 8.2 Hz); 4.64-4.55 (2H, m); 3.17 (3H, s); 2.30 (3H, s).

APCI-MS m/z: 549.1 [MH$^+$].

EXAMPLE 41

6-Methyl-5-(5-methyl-4H-[1,2,4]triazol-3-yl)-2-oxo-1-(3-trifluoromethyl-phenyl)-1,2-dihydro-pyridine-3-carboxylic acid 4-methylsulfonyl-benzylamide The compound of Example 38 (a) (0.017 g, 0.0325 mmol), toluene (1 ml), NMP (0.5 ml), triethylamine (0.5 ml), ethyl acetamidate hydrochloride (0.030 g, 0.24 mmol) and a magnetic stirrer bar were placed in a glass vial. The vial was sealed and the mixture was heated with stirring at 100° C. overnight. The mixture was allowed to cool and was then concentrated in vacuo. Purification by preparative HPLC and subsequent freeze-drying of the pure fractions afforded the title compound (0.005 g, 28%) as a white solid.

$^1$H NMR (DMSO-$d_6$): δ 13.79 (1H, bs); 9.89 (1H, t, J 6.0 Hz); 8.99 (1H, s); 7.97 (1H, s); 7.90 (1H, d, J 8.0 Hz); 7.87 (2H, d, J 8.2 Hz); 7.83 (1H, t, J 7.9 Hz); 7.78 (1H, d, J 7.9 Hz); 7.55 (2H, d, J 8.3 Hz); 4.67-4.55 (2H, m); 3.17 (3H, s); 2.41 (3H, s); 2.41 (3H, s).

APCI-MS m/z: 546.2 [MH$^+$].

EXAMPLE 42

5-(4,5-Dimethyl-4H-[1,2,4]triazol-3-yl)-6-methyl-2-oxo-1-(3-trifluoromethyl-phenyl)-1,2-dihydro-pyridine-3-carboxylic acid 4-methanesulfonyl-benzylamide A solution of $POCl_3$ (0.030 g, 0.2 mmol) in $CHCl_3$ (1 ml) and pyridine (1 ml) was added to N-methylacetamide (0.015 g, 0.2 mmol) and the mixture was cooled in an ice-water bath and stirred for 90 minutes. To this solution was added a solution of 5-hydrazinocarbonyl-6-methyl-2-oxo-1-(3-trifluoromethyl-phenyl)-1,2-dihydro-pyridine-3-carboxylic acid 4-methanesulfonyl-benzylamide (Example 38 (a), 0.040 g, 0.076 mmol) in $CHCl_3$ (2 ml) and the mixture was stirred overnight at room temperature. Purification by preparative HPLC gave the linear intermediate (0.020 g). This material was suspended in EtOAc (2 ml) and was heated (90° C.) with stirring for 4 h, giving rise to a mixture of three components. This mixture was purified on preparative HPLC giving the title compound (0.003 g, 7%) after freeze-drying the pure fractions.

$^1$H NMR (DMSO-$d_6$): δ 9.89 (1H, t, J 6.1 Hz); 8.29 (1H, s); 8.04 (1H, s); 7.94-7.89 (1H, m); 7.87 (2H, d, J 8.6 Hz); 7.87-7.83 (2H, m); 7.55 (2H, d, J 8.3 Hz); 4.66-4.55 (2H, m); 3.45 (3H, s); 3.17 (3H, s); 2.39 (3H, s); 1.87 (3H, s).

APCI-MS m/z: 560.2 [MH$^+$].

EXAMPLE 43

5-(5-Methoxymethyl-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide a) 5-[N$^1$-(2-Methoxy-acetyl)-hydrazinocarbonyl]-6-methyl-2-oxo-1-(3-trifluoromethyl-phenyl)-1,2-dihydro-pyridine-3-carboxylic acid 4-methanesulfonyl-benzylamide The compound obtained in Example 38 (a) (0.028 g, 0.053 mmol) in dry THF (2 ml) was treated with triethylamine (0.020 g, 0.20 mmol) and 2-methoxyacetyl chloride (0.02 g, 0.18 mmol). The mixture was stirred for 5 minutes and LC-MS showed complete conversion of the starting material to a mixture of three compounds. The reaction was quenched by the addition of MeOH, and subsequent evaporation and purification on preparative HPLC afforded the subtitle compound (0.015 g, 47%) as a white solid after freeze-drying the pure fractions.

$^1$H NMR (DMSO-$d_6$): δ10.29 (1H, s); 9.95 (1H, s); 9.79 (1H, t, J 6.3 Hz); 8.51 (1H, s); 7.93 (1H, s); 7.94-7.89 (1H, m); 7.87 (2H, d, J 8.3 Hz); 7.82 (1H, d, J 7.8 Hz); 7.74 (1H, d, J 7.7 Hz); 7.55 (2H, d, J 8.1 Hz); 4.65-4.55 (2H, m); 3.97 (2H, s); 3.36 (3H, s); 3.17 (3H, s); 2.18 (3H, s).

APCI-MS m/z: 595.2 [MH$^+$].

b) 5-(5-Methoxymethyl-[1,3,4]oxadiazol-2-yl)-6-methyl-2-oxo-1-(3-trifluoromethyl-phenyl-1,2-dihydro-pyridine-3-carboxylic acid 4-methanesulfonyl-benzylamide Prepared according to the procedure described in Example 38 (c) starting from 0.015 g (0.025 mmol) of the compound obtained in step (a). The title compound (0.011 g, 80%) was obtained as a white solid after purification on preparative HPLC and freeze-drying of the pure fractions.

$^1$H NMR (DMSO-$d_6$): δ 9.73 (1H, t, J 6.1 Hz); 8.79 (1H, s); 8.01 (1H, s); 7.94 (1H, d, J 7.9 Hz); 7.87 (2H, d, J 8.14 Hz); 7.86-7.84 (1H, m); 7.71 (1H, d, J 7.9 Hz); 7.56 (2H, d, J 8.1 Hz); 4.75 (2H, s); 4.65-4.55 (2H, m); 3.39 (3H, s); 3.17 (3H, s); 2.45 (3H, s).

APCI-MS m/z: 577.2 [MH$^+$].

EXAMPLE 44

N-[4-(Isopropylsulfonyl)benzyl]-6-methyl-5-(5-methyl-1,3,4-oxadiazol-2-yl)-2-oxo-1-[3-(trifluoromethyl)phenyl]-1,2-dihydropyridine-3-carboxamide The title compound was prepared by an analogous method to that described in Example 14.

$^1$H NMR (CDCl$_3$): δ 9.96 (1H, bt); 9.08 (1H, s); 7.89-7.78 (4H, m); 7.55-7.45 (4H, m); 4.78-4.65 (2H, m); 3.20-3.13 (1H, m); 2.68 (3H, s); 2.62 (3H, s); 1.28 (6H, d, J 6.9 Hz).

APCI-MS m/z: 575 [MH$^+$].

EXAMPLE 45

N-[4-(Ethylsulfonyl)benzyl]-6-methyl-5-(5-methyl-1,3,4-oxadiazol-2-yl)-2-oxo-1-[3-(trifluoromethyl)phenyl]-1,2-dihydropyridine-3-carboxamide The title compound was prepared by an analogous method to that described in Example 14.

$^1$H NMR (CDCl$_3$): δ 9.80-9.71 (1H, m); 9.09 (1H, s); 7.90-7.74 (4H, m); 7.56-7.42 (4H, m); 4.79-4.63 (2H, m); 3.08 (2H, q, J 7.5 Hz); 2.64 (3H, s); 2.62 (3H, s); 1.27 (3H, t, J 7.4 Hz).

APCI-MS m/z: 561.1 [MH$^+$].

EXAMPLE 46

N-[4-(Cyclopropylsulfonyl)benzyl]-6-methyl-5-(5-methyl-1,3,4-oxadiazol-2-yl)-2-oxo-1-[3-(trifluoromethyl)phenyl]-1,2-dihydropyridine-3-carboxamide The title compound was prepared by an analogous method to that described in Example 14.

$^1$H NMR (CDCl$_3$): δ 9.74 (1H, bt); 9.09 (1H, s); 7.87-7.77 (4H, m); 7.54-7.45 (4H, m); 4.75-4.64 (2H, m); 2.64 (3H, s); 2.62 (3H, s); 2.46-2.39 (1H, m); 1.35-1.31 (2H, m); 1.04-0.99 (2H, m).

APCI-MS m/z: 573 [MH$^+$].

EXAMPLE 47

6-Methyl-5-[1,3,4]oxadiazol-2-yl-2-oxo-1-(3-trifluoromethyl-phenyl)-1,2-dihydro-pyridine-3-carboxylic acid 4-(propane-2-sulfonyl)-benzylamide The title compound (0.025 g, 64%) was prepared by an analogous method to that described in Example 39.

$^1$H NMR (DMSO-$d_6$): δ 9.75 (1H, t, J 6.2 Hz); 9.38 (1H, s); 8.82 (1H, s); 8.02 (1H, s); 7.94 (1H, d, J 7.5 Hz); 7.89-7.82 (2H, m); 7.80 (2H, d, J 8.2 Hz); 7.56 (2H, d, J 8.2 Hz); 4.68-4.56 (2H, m); 3.37 (1H, p, J 6.8 Hz); 2.45 (3H, s); 1.13 (6H, d, J 6.2 Hz).

APCI-MS m/z: 561.2 [MH$^+$].

EXAMPLE 48

6-Methyl-5-[1,3,4]oxadiazol-2-yl-2-oxo-1-(3-trifluoromethyl-phenyl)-1,2-dihydro-pyridine-3-carboxylic acid 4-cyclopropanesulfonyl-benzylamide The title compound (0.023 g, 80%) was prepared by an analogous method to that described in Example 39.

$^1$H NMR (DMSO-d$_6$): δ 9.74 (1H, t, J 6.2 Hz); 9.38 (1H, s); 8.82 (1H, s); 8.01 (1H, s); 7.94 (1H, d, J 7.7 Hz); 7.89-7.80 (2H, m); 7.84 (2H, d, J 8.2 Hz); 7.55 (2H, d, J 8.2 Hz); 4.66-4.56 (2H, m); 2.84-2.77 (1H, m); 2.44 (3H, s); 1.12-1.05 (2H, m); 1.05-0.97 (2H, m).

APCI-MS m/z: 559.2 [MH$^+$].

EXAMPLE 50

6-Methyl-5-(2-methyl-1,3-oxazol-4-yl)-N-[4-(methylsulfonyl)benzyl]-2-oxo-1-[3-(trifluoromethyl)phenyl]-1,2-dihydropyridine-3-carboxamide a) 5-(1-Butoxyvinyl)-6-methyl-N-[4-(methylsulfonyl)benzyl]-2-oxo-1-[3-(trifluoromethyl)phenyl]-1,2-dihydropyridine-3-carboxamide 5-Iodo-6-methyl-N-[4-(methylsulfonyl)benzyl]-2-oxo-1-[3-(trifluoromethyl)phenyl]-1,2-dihydropyridine-3-carboxamide (Example 1 (d), 101.5 mg, 0.17 mmol), bis[1,2-bis(diphenylphosphino)ethane]-palladium (0) (16.5 mg, 18.3 µmmol), n-butyl vinyl ether (60 µl, 0.46 mmol), triethylamine (0.5 ml, 3.6 mmol) and DMF (6 ml) were placed in a Schlenk vessel equipped with a magnetic stirring bar. The vessel was purged with argon, sealed, and heated at 100° C. overnight. The reaction mixture was cooled and partitioned between ethyl acetate and water. The organic layer was dried over sodium sulphate, filtered and concentrated in vacuo. The residue was purified by preparative HPLC to give the title compound as a white solid (27.3 mg, 28%).

$^1$H NMR (CDCl$_3$): δ 9.96 (1H, t, J 5.8 Hz); 8.64 (1H, s); 7.89 (2H, d, J 8.3 Hz); 7.82 (1H, d, J 8.0 Hz); 7.75 (1H, t, J 7.9 Hz); 7.56-7.50 (3H, m); 7.46 (1H, d, J 7.8 Hz); 4.69 (2H, ddd, J 22.1, 15.7, 6.2 Hz); 4.43 (1H, d, J 2.6 Hz); 4.26 (1H, d, J 2.6 Hz); 3.83 (2H, t, J 6.5 Hz); 3.03 (3H, s); 2.11 (3H, s); 1.74 (2H, quintet, J 9.2 Hz); 1.46 (2H, sextet, J 9.1 Hz); 0.98 (3H, t, J 7.4 Hz).

APCI-MS m/z: 563 [MH$^+$].

b) 5-Acetyl-6-methyl-N-[4-(methylsulfonyl)benzyl]-2-oxo-1-[3-(trifluoromethyl)phenyl]-1,2-dihydropyridine-3-carboxamide Aqueous hydrochloric acid (2.0M, 50 µl) was added to a solution of 5-(1-butoxyvinyl)-6-methyl-N-[4-(methylsulfonyl)benzyl]-2-oxo-1-[3-(trifluoromethyl)phenyl]-1,2-dihydropyridine-3-carboxamide (38 mg, 67.5 µmol) in DMF (0.5 ml). After 20 min. the solution was neutralized with aqueous sodium hydrogen carbonate. The reaction mixture was purified by preparative HPLC to give the title compound as a white solid (17.6 mg, 51%).

$^1$H NMR (CDCl$_3$): δ 9.75 (1H, t, J 5.7 Hz); 9.08 (1H, s); 7.90 (2H, d, J 8.3 Hz); 7.85 (1H, d, 7.9 Hz); 7.78 (1H, t, 7.9 Hz); 7.54 (2H, J 8.3 Hz); 7.50 (1H, s); 7.42 (1H, J 8.0 Hz); 4.70 (2H, t, J 6.0 Hz); 3.03 (3H, s); 2.66 (3H, s); 2.43 (3H, s).

APCI-MS m/z: 507 [MH$^+$].

c) 5-Bromoacetyl-6-methyl-N-[4-(methylsulfonyl)benzyl]-2-oxo-1-[3-(trifluoromethyl)phenyl]-1,2-dihydropyridine-3-carboxamide Bromine (34 µl, 0.66 mmol) in THF (5 ml) was added to a solution of 5-acetyl-6-methyl-N-[4-(methylsulfonyl)benzyl]-2-oxo-1-[3-(trifluoromethyl)phenyl]-1,2-dihydropyridine-3-carboxamide (320 mg, 0.63 mmol) in THF (10 ml). After 2 h, the yellow colour had disappeared. The reaction mixture was partitioned between water and ethyl acetate, the organic phase was separated, evaporated, and the residue was chromatographed on silica using ethyl acetate/heptane (1/1, 2/1, 4/1) as eluent. Fractions containing the product were combined and evaporated to give the title compound (150 mg, 41%).

$^1$H NMR (CDCl$_3$): δ 9.67 (1H, t); 9.00 (1H, s); 7.89 (2H, d); 7.86 (1H, d); 7.78 (1H, t); 7.52 (2H, d); 7.50 (1H, s); 7.42 (1H, d); 4.69 (2H, m); 4.41 (2H, s); 3.02 (3H, s); 2.42 (3H, s).

d) 6-Methyl-5-(2-methyl-1,3-oxazol-4-yl)-N-[4-(methylsulfonyl)benzyl]-2-oxo-1-[3-(trifluoromethyl)phenyl]-1,2-dihydropyridine-3-carboxamide A mixture of 5-(bromoacetyl)-6-methyl-N-[4-(methylsulfonyl)benzyl]-2-oxo-1-[3-(trifluoromethyl)phenyl]-1,2-dihydropyridine-3-carboxamide (90 mg, 0.15 mmol) and acetamide (44 mg, 0.75 mmol), xylene (300 µl) and conc. H$_2$SO$_4$ (10 µl) was heated with stirring for 3 h. The reaction was diluted with water and CH$_3$CN and purified on preparative HPLC affording the title compound (37 mg, 45%).

$^1$H NMR (CDCl$_3$): δ 10.08 (1H, t); 8.69 (1H, s); 7.88 (2H, d); 7.82 (1H, d); 7.76 (1H, t); 7.72 (1H, s); 7.54 (1H, s); 7.52 (2H, d); 7.46 (1H, d); 4.69 (2H, m); 3.02 (3H, s); 2.56 (3H, s); 2.19 (3H, s).

APCI-MS m/z: 546.4 [MH$^+$].

EXAMPLE 51

6-Methyl-N-[4-(methylsulfonyl)benzyl]-5-(1,3-oxazol-4-yl)-2-oxo-1-[3-(trifluoromethyl)phenyl]-1,2-dihydropyridine-3-carboxamide A mixture of 5-(bromoacetyl)-6-methyl-N-[4-(methylsulfonyl)benzyl]-2-oxo-1-[3-(trifluoromethyl)phenyl]-1,2-dihydropyridine-3-carboxamide (Example 50 (c), 100 mg, 0.17 mmol), formamide (135 µl, 3.4 mmol), xylene (300 µl) and conc. H$_2$SO$_4$ (10 µl) was heated with stirring for 2 h. The reaction was diluted with water and CH$_3$CN and purified on preparative HPLC, affording the title compound (23 mg, 31%).

$^1$H NMR (CDCl$_3$): δ 9.95 (1H, t); 8.75 (1H, s); 7.99 (1H, d); 7.88 (2H, d); 7.86 (1H, d); 7.83 (1H, d); 7.76 (1H, t); 7.72 (1H, s); 7.52 (2H, d); 7.47 (1H, d); 4.69 (2H, m); 3.03 (3H, s); 2.24 (3H, s).

APCI-MS m/z: 523.3 [MH$^+$].

EXAMPLE 52

5-(2-Amino-thiazol-4-yl)-6-methyl-2-oxo-1-(3-trifluoromethyl-phenyl)-1,2-dihydro-pyridine-3-carboxylic acid 4-methanesulfonyl-benzylamide 5-Bromoacetyl-6-methyl-2-oxo-1-(3-trifluoromethyl-phenyl)-1,2-dihydro-pyridine-3-carboxylic acid 4-methanesulfonyl-benzylamide (Example 50 (c), 0.04 g, 0.067 mmol), thiourea (0.0067 g, 0.086 mmol), NaOAc (0.011 g, 0.136 mmol), EtOH (2 ml) and a magnetic stirrer bar were placed in a tube designed for microwave synthesis. The vial was sealed and the mixture was heated in a CEM Discover Microwave apparatus (100 W, 90° C.) for 20 minutes, giving complete conversion of the starting material to a single product according to LC-MS. The solvents were evaporated to give a crude mixture which was purified on preparative HPLC giving the title compound (0.026 g, 66%) as a slightly yellowish solid after freeze-drying the pure fractions.

$^1$H NMR (DMSO-d$_6$): δ 9.92 (1H, t, J 6.1 Hz); 8.64 (1H, s); 7.94 (1H, s); 7.90 (1H, d, J 8.0 Hz); 7.87 (2H, d, J 8.3 Hz); 7.81 (1H, d, J 7.7 Hz); 7.75 (1H, d, J 7.75 Hz); 7.54 (2H, d, J 8.2 Hz); 7.11 (2H, bs); 6.64 (1H, s); 4.65-4.55 (2H, m); 3.17 (3H, s); 2.17 (3H, s).

APCI-MS m/z: 563 [MH$^+$].

EXAMPLE 53

5-(2,5-Dimethyl-1,3-oxazol-4-yl)-6-methyl-N-[4-(methylsulfonyl)benzyl]-2-oxo-1-[3-(trifluoromethyl)phenyl]-1,2-dihydropyridine-3-carboxamide a) 6-Methyl-N-[4-(methylsulfonyl)benzyl]-2-oxo-5-propionyl-1-[3-(trifluoromethyl)phenyl]-1,2-dihydropyridine-3-carboxamide A solution of 5-iodo-6-methyl-N-[4-(methylsulfonyl)benzyl]-2-oxo-1-[3-(trifluoromethyl)phenyl]-1,2-dihydropyridine-3-carboxamide (Example 1 (d), 1500 mg, 2.5 mmol), bis[1,2-bis(diphenylphosphino)ethane]palladium(0) (230 mg, 0.25 mmol), triethylamine (7.5 ml, 54 mmol) and ethylpropenyl ether (900 µl, 7.5 mmol) in DMF (45 ml) was heated at 100° C. overnight. After cooling, the reaction mixture was poured into water and extracted with ethyl acetate and the solvent was removed under reduced pressure. The crude product was then dissolved in DMF (25 ml) and 2M HCl (25 ml) and then stirred for 1.5 h. The reaction mixture was then poured into aqueous NaHCO$_3$ and extracted with ethyl acetate. The extracts were separated, evaporated under reduced pressure, and the residue was chromatographed on silica using ethyl acetate/heptane (2/1, 4/1, 10/1) as eluent. Fractions containing the product were combined and evaporated to give the title compound (1.3 g, >99%).

$^1$H NMR (CDCl$_3$): δ 9.76 (1H, t); 9.06 (1H, s); 7.89 (2H, d); 7.84 (1H, d); 7.76 (1H, t); 7.52 (2H, d); 7.49 (1H, s); 7.40 (1H, d); 4.68 (2H, m); 3.02 (3H, s); 3.00 (2H, q); 2.39 (3H, s); 1.22 (3H, t).

b) 5-(2-Bromopropanoyl)-6-methyl-N-[4-methylsulfonyl)benzyl]-2-oxo-1-[3-(trifluoromethyl)phenyl]-1,2-dihydropyridine-3-carboxamide Bromine (84 µl, 1.61 mmol) in THF (5 ml) was added to a solution of 6-methyl-N-[4-(methylsulfonyl)benzyl]-2-oxo-5-propionyl-1-[3-(trifluoromethyl)phenyl]-1,2-dihydropyridine-3-carboxamide (700 mg, 1.34 mmol) in THF (10 ml). After 2 h, the yellow colour had disappeared. The reaction mixture was partitioned between water and ethyl acetate, the organic phase was separated, dried and evaporated under reduced pressure to give the title compound (800 mg, 99%).

$^1$H NMR (CDCl$_3$): δ 9.71 (1H, t); 8.97 (1H, s); 7.89 (2H, d); 7.85 (1H, d); 7.77 (1H, t); 7.52 (2H, d); 7.46 (1H, d); 7.40 (1H, d); 5.28 (1H, q); 4.69 (2H, m); 3.02 (3H, s); 2.36 (3H, s); 1.90 (3H, d).

c) 5-(2,5-Dimethyl-1,3-oxazol-4-yl)-6-methyl-N-[4-(methylsulfonyl)benzyl]-2-oxo-1-[3-trifluoromethyl)phenyl]-1,2-dihydropyridine-3-carboxamide A mixture of 5-(2-bromopropanoyl)-6-methyl-N-[4-(methylsulfonyl)benzyl]-2-oxo-1-(3-(trifluoromethyl)phenyl)-1,2-dihydropyridine-3-carboxamide (130 mg, 0.22 mmol), acetamide (262 mg, 4.4 mmol), xylene (300 µl) and conc. H$_2$SO$_4$ (10 µl) was heated with stirring for 2 h. The reaction was diluted with water and CH$_3$CN and purified on preparative HPLC, affording the title compound (45 mg, 36%).

$^1$H NMR (CDCl$_3$): δ 10.00 (1H, t); 8.54 (1H, s); 7.88 (2H, d); 7.82 (1H, d); 7.75 (1H, t); 7.54 (1H, d); 7.52 (2H, d); 7.47 (1H, d); 4.68 (2H, m); 3.02 (3H, s); 2.51 (3H, s); 2.34 (3H, s); 2.11 (3H, s).

APCI-MS m/z: 560.4 [MH$^+$].

EXAMPLE 54

6-Methyl-5-(5-methyl-1,3-oxazol-4-yl)-N-[4-(methylsulfonyl)benzyl]-2-oxo-1-[3-(trifluoromethyl)phenyl]-1,2-dihydropyridine-3-carboxamide A mixture of 5-(2-bromopropanoyl)-6-methyl-N-[4-(methylsulfonyl)benzyl]-2-oxo-1-[3-(trifluoromethyl)phenyl]-1,2-dihydropyridine-3-carboxamide (Example 53 (b), 130 mg, 0.22 mmol), formamide (176 µl, 4.4 mmol), xylene (300 µl) and conc. H$_2$SO$_4$ (10 µl) was heated with stirring for 2 h. The reaction was diluted with water and CH$_3$CN and purified on preparative HPLC, affording the title compound (27 mg, 23%).

$^1$H NMR (CDCl$_3$): δ 10.02 (1H, t); 8.57 (1H, d); 7.89 (1H, s); 7.88 (2H, d); 7.83 (1H, d); 7.76 (1H, t); 7.55 (1H, d); 7.52 (2H, d); 7.48 (1H, d); 4.69 (2H, m); 3.02 (3H, s); 2.41 (3H, s); 2.09 (3H, s).

APCI-MS m/z: 546.3 [MH$^+$].

EXAMPLE 55

5-(2-Amino-5-methyl-thiazol-4-yl)-6-methyl-2-oxo-1-(3-trifluoromethyl-phenyl)-1,2-dihydro-pyridine-3-carboxylic acid 4-methanesulfonyl-benzylamide 5-(2-Bromopropanoyl)-6-methyl-N-[4-(methylsulfonyl)benzyl]-2-oxo-1-[3-(trifluoromethyl)phenyl]-1,2-dihydropyridine-3-carboxamide (Example 53 (b), 0.04 g, 0.067 mmol), thiourea (0.0067 g, 0.086 mmol), NaOAc (0.011 g, 0.136 mmol), EtOH (2 ml) and a magnetic stirrer bar were placed in a tube designed for microwave synthesis. The vial was sealed and the mixture was heated in a CEM Discover Microwave apparatus (100 W, 90° C.) for 20 minutes, giving complete conversion of the starting material to a single product according to LC-MS. The solvents were evaporated to give a crude mixture which was purified on preparative HPLC, giving the title compound (0.026 g, 66%) as a slightly yellowish solid after freeze-drying the pure fractions.

$^1$H NMR (DMSO-d$_6$): δ 9.90 (1H, t, J 6.2 Hz); 8.32 (1H, s); 7.98 (1H, s); 7.91 (1H, d, J 7.9 Hz); 7.87 (2H, d, J 8.3 Hz); 7.83 (1H, t, J 7.8 Hz); 7.77 (1H, d, J 7.8 Hz); 7.54 (2H, d, J 8.2 Hz); 4.67-4.55 (2H, m); 3.18 (3H, s); 2.12 (3H, s); 1.91 (3H, s).

APCI-MS m/z: 577.1 [MH$^+$].

EXAMPLE 56

5-(2-Hydroxymethyl-5-methyl-thiazol-4-yl)-6-methyl-2-oxo-1-(3-trifluoromethyl-phenyl)-1,2-dihydro-pyridine-3-carboxylic acid 4-methanesulfonyl-benzylamide 5-(2-Bromopropanoyl)-6-methyl-N-[4-(methylsulfonyl)benzyl]-2-oxo-1-[3-(trifluoromethyl)phenyl]-1,2-dihydropyridine-3-carboxamide (Example 53 (b), 0.06 g, 0.10 mmol), 2-amino-2-thioxoethyl pivalate (0.022 g, 0.125 mmol), EtOH (2 ml) and a magnetic stirrer bar were placed in a tube designed for microwave synthesis. The vial was sealed and the mixture was heated in a CEM Discover Microwave apparatus (100 W, 80° C.) for 40 minutes, giving complete conversion of the starting material to a single product according to LC-MS. The solvents were evaporated to give a crude mixture which was purified on silica giving 0.045 g (76%) of the intermediate pivalyl ester. This compound was dissolved in THF (2 ml) and water (2 ml). To this solution was added NaOH (0.2 mmol, 0.1 ml of a 2M solution), and the mixture was stirred at room temperature overnight. The THF was evaporated off and the water phase was acidified, extracted, and the extracts were evaporated. Purification by preparative HPLC gave pure fractions which were freeze-dried to give the title compound (0.040 g, 68%) as a white solid.

$^1$H NMR (DMSO-$d_6$): δ 9.92 (1H, t, J 6.2 Hz); 8.30 (1H, s); 8.02 (1H, s); 7.92-7.88 (1H, d); 7.87 (2H, d, J 8.5 Hz); 7.88-7.78 (2H, m); 7.54 (2H, d, J 8.4 Hz); 6.02 (1H, J 5.8 Hz); 4.69 (2H, d, J 5.8 Hz); 4.64-4.54 (2H, m); 3.17 (3H, s); 2.34 (3H, s); 1.89 (3H, s)

APCI-MS m/z: 592.1 [MH$^+$].

EXAMPLE 57

6-Methyl-5-(5-methyl-[1,2,4]oxadiazol-3-yl)-2-oxo-1-(3-trifluoromethyl-phenyl)-1,2-dihydro-pyridine-3-carboxylic acid 4-methanesulfonyl-benzylamide a) 5-Cyano-6-methyl-N-[4-(methylsulfonyl)benzyl]-2-oxo-1-[3-(trifluoromethyl)phenyl]-1,2-dihydropyridine-3-carboxamide A mixture of 5-iodo-6-methyl-N-[4-(methylsulfonyl)benzyl]-2-oxo-1-[3-(trifluoromethyl)phenyl]-1,2-dihydropyridine-3-carboxamide (Example 1 (d), 120 mg, 0.20 mmol) and copper (I) cyanide (66.7 mg, 0.74 mmol) in NMP (2.5 ml) was stirred overnight at 140° C. The reaction mixture was cooled and partitioned between ethyl acetate and water. The organic layer was dried over sodium sulphate, filtered and concentrated in vacuo. The residue was first purified by preparative HPLC and then by flash chromatography eluting with dichloromethane/methanol (10:0.2) to give the title compound as a white solid (24 mg, 24%).

$^1$H NMR (DMSO-$d_6$): δ 9.55 (1H, t, J 6.1 Hz); 8.49 (1H, s); 7.96 (1H, s); 7.93 (1H, d, J 7.8 Hz); 7.88-7.81 (3H, m); 7.77 (1H, d, 3" 8.0 Hz); 7.52 (2H, d, J 8.4 Hz); 4.56 (2H, d, J 6.2 Hz); 3.16 (3H, s); 2.22 (3H, s).

APCI-MS m/z: 490 [MH$^+$].

b) 5-(N-Hydroxycarbamimidoyl)-6-methyl-2-oxo-1-(3-trifluoromethyl-phenyl)-1,2-dihydro-pyridine-3-carboxylic acid 4-methanesulfonyl-benzylamide 5-Cyano-6-methyl-N-[4-(methylsulfonyl)benzyl]-2-oxo-1-[3-(trifluoromethyl)phenyl]-1,2-dihydropyridine-3-carboxamide (0.040 g, 0.082 mmol), hydroxylamine hydrochloride (0.015 g, 0.209 mmol), NaOAc (0.017 g, 0.209 mmol), ethanol (3 ml), water (0.1 ml) and a magnetic stirrer bar were placed in a vial. The mixture was heated (90° C.) overnight. LC-MS showed a 50:50 mixture of two components, one of which had the expected MW. The product was isolated by preparative HPLC giving 0.012 g (28%) of the intermediate N-hydroxyamidine.

$^1$H NMR (DMSO-$d_6$): δ 9.85 (1H, t, J 6.2 Hz); 9.53 (1H, s); 8.33 (1H, s); 7.91 (1H, d, J 7.6 Hz); 7.86 (2H, d, J 8.2 Hz); 7.85 (1H, s); 7.83 (1H, t, J 7.8 Hz); 7.69 (1H, d, J 7.8 Hz); 7.54 (2H, d, J 8.3 Hz); 5.88 (2H, bs); 4.64-4.55 (2H, m); 3.17 (3H, s); 2.07 (3H, s).

APCI-MS m/z: 523.2 [MH$^+$].

c) 6-Methyl-5-(5-methyl-[1,2,4]oxadiazol-3-yl)-2-oxo-1-(3-trifluoromethyl-phenyl)-1,2-dihydro-pyridine-3-carboxylic acid 4-methanesulfonyl-benzyl amide 5-(N-Hydroxycarbamimidoyl)-6-methyl-2-oxo-1-(3-trifluoromethyl-phenyl)-1,2-dihydro-pyridine-3-carboxylic acid 4-methanesulfonyl-benzylamide (0.011 g, 0.021 mmol), acetic anhydride (0.02 g, 0.195 mmol), toluene (2 ml) and a magnetic stirrer bar were placed in a vial. The vial was sealed and was heated (110° C.) with stirring for 5 h. LC-MS confirmed the consumption of the starting material and the formation of a product with the expected MW. Evaporation and purification on preparative HPLC gave the title compound (0.004 g, 35%) as a white solid after freeze-drying the pure fractions.

$^1$H NMR (DMSO-$d_6$): δ 9.77 (1H, t, J 6.2 Hz); 8.90 (1H, s); 8.01 (1H, s); 7.93 (1H, d, J 7.5 Hz); 7.87 (2H, d, J 8.3 Hz); 7.87-7.79 (2H, m); 7.55 (2H, d, J 8.3 Hz); 7.67-7.53 (2H, m); 3.17 (3H, s); 2.69 (3H, s); 2.37 (3H, s).

APCI-MS m/z: 547.2 [MH$^+$].

EXAMPLE 58

6-Methyl-5-[1,2,4]oxadiazol-3-yl-2-oxo-1-(3-trifluoromethyl-phenyl)-1,2-dihydro-pyridine-3-carboxylic acid 4-methanesulfonyl-benzylamide 5-Cyano-6-methyl-N-[4-(methylsulfonyl)benzyl]-2-oxo-1-[3-(trifluoromethyl)phenyl]-1,2-dihydropyridine-3-carboxamide (Example 57 (a), 0.040 g, 0.082 mmol), hydroxylamine hydrochloride (0.015 g, 0.209 mmol), NaOAc (0.017 g, 0.209 mmol), ethanol (3 ml), water (0.1 ml) and a magnetic stirrer bar were placed in a vial. The mixture was heated (90° C.) overnight. The solvents were evaporated in vacuo. The residue was dissolved in triethyl-orthoformate (3 ml) in a vial and a magnetic stirrer bar was added. The vial was sealed and heated (130° C.) with stirring for 2 h. LC-MS confirmed formation of a product with the expected MW. The volatiles were removed in vacuo, and the residue was purified on preparative HPLC giving the title compound (0.012 g, 27%) as a white solid after freeze-drying the pure fractions.

$^1$H NMR (DMSO-$d_6$): δ 9.78 (1H, s); 9.77 (1H, t, J 6.2 Hz); 8.93 (1H, a); 8.03 (1H, s); 7.93 (1H, d, J 7.7 Hz); 7.87 (2H, d, J 8.2 Hz); 7.86-7.80 (2H, m); 7.56 (2H, d, J 8.2 Hz); 4.65-4.55 (2H, m); 3.17 (3H, s); 2.39 (3H, s).

APCI-MS m/z: 533.2 [MH$^+$].

EXAMPLE 59

6-Methyl-2-oxo-5-(1H-tetrazol-5-yl)-1-(3-trifluoromethyl-phenyl)-1,2-dihydro-pyridine-3-carboxylic acid 4-methanesulfonyl-benzylamide 5-Cyano-6-methyl-N-[4-(methylsulfonyl)benzyl]-2-oxo-1-[3-(trifluoromethyl)phenyl]-1,2-dihydropyridine-3-carboxamide (Example 57 (a), 0.018 g, 0.037 mmol), NaN$_3$ (0.020 g, 0.307 mmol), NH$_4$Cl (0.016 g, 0.307 mmol), NMP (1 ml) and a magnetic stirrer bar were placed in a tube designed for microwave synthesis. The vial was sealed and the mixture was heated in a CEM Discover Microwave apparatus (100 W, 140° C.) for 30 minutes, giving complete conversion of the nitrile according to LC-MS. The crude mixture was dissolved in acetonitrile (2 ml) and water (2 ml) and was purified directly on preparative HPLC under acidic conditions, giving the title compound (0.012 g, 61%) as a beige solid after freeze-drying the pure fractions.

$^1$H NMR (DMSO-d$_6$): δ 9.81 (1H, t, J 6.1 Hz); 8.79 (1H, bs); 8.02 (1H, bs); 7.93 (1H, d, 7.89 Hz); 7.87 (2H, d, J 8.5 Hz); 7.88-7.85 (1H, m); 7.82 (1H, d, J 8.2 Hz); 7.56 (2H, d, J 8.4 Hz); 4.67-4.55 (2H, m); 3.17 (3H, s); 2.34 (3H, s).

APCI-MS m/z: 533.2 [MH$^+$].

EXAMPLE 60

6-Methyl-5-(4-methyl-oxazol-2-yl)-2-oxo-1-(3-trifluoromethyl-phenyl)-1,2-dihydro-pyridine-3-carboxylic acid 4-methanesulfonyl-benzylamide 6-Methyl-2-oxo-1-(3-trifluoromethyl-phenyl)-1,2-dihydro-pyridine-3,5-dicarboxylic acid 5-amide 4-methanesulfonyl-benzylamide [prepared from the acid chloride of 5-(4-methanesulfonyl-benzylcarbamoyl)-2-methyl-6-oxo-1-(3-trifluoromethyl-phenyl)-1,6-dihydro-pyridine-3-carboxylic acid [described in Example 14 (b)] and ammonia] (0.05 g, 0.098 mmol), 1-chloroacetone (0.025 g, 0.27 mmol), CaCO$_3$ (0.015 g, 0.15 mmol), NMP (1.5 ml) and a magnetic stirrer bar were placed in a tube designed for microwave synthesis. The vial was sealed and the mixture was heated in a CEM Discover Microwave apparatus (100 W, 155° C.) for 60 minutes, giving complete conversion of the amide according to LC-MS. The crude mixture was dissolved in acetonitrile (2 ml) and water (2 ml) and was purified directly on preparative HPLC giving the title compound (0.006 g, 11%) as a solid after freeze-drying the pure fractions.

$^1$H NMR (DMSO-d$_6$): δ 9.79 (1H, t, J 6.1 Hz); 8.89 (1H, s); 7.98 (1H, bs); 7.97-7.95 (1H, m); 7.92 (1H, d, J 7.8 Hz); 7.87 (2H, d, J 8.1 Hz); 7.85 (1H, t, J 7.9 Hz); 7.79 (1H, d, J 7.9 Hz); 7.55 (2H, d, J 8.2 Hz); 4.66-4.55 (2H, m); 3.17 (3H, s); 2.45 (3H, s); 2.17 (3H, s).

APCI-MS m/z: 546.2 [MH$^+$].

EXAMPLE 61

5-(4,5-Dimethyl-oxazol-2-yl)-6-methyl-2-oxo-1-(3-trifluoromethyl-phenyl)-1,2-dihydro-pyridine-3-carboxylic acid 4-methanesulfonyl-benzylamide 6-Methyl-2-oxo-1-(3-trifluoromethyl-phenyl)-1,2-dihydro-pyridine-3,5-dicarboxylic acid 5-amide 4-methanesulfonyl-benzylamide (see Example 60, 0.05 g, 0.098 mmol), 3-bromo-2-butanone (0.020 g, 0.20 mmol), CaCO$_3$ (0.015 g, 0.15 mmol), NMP (1.5 ml) and a magnetic stirrer bar were placed in a tube designed for microwave synthesis. The vial was sealed and the mixture was heated in a CEM Discover Microwave apparatus (100 W, 140° C.) for 2 h. The reaction was stopped and the crude mixture was dissolved in acetonitrile (2 ml) and water (2 ml) and was purified directly on preparative HPLC, giving the title compound (0.007 g, 13%) as a slightly brownish solid after freeze-drying the pure fractions.

$^1$H NMR (DMSO-d$_6$): δ 9.81 (1H, t, J 6.1 Hz); 8.85 (1H, s); 7.98 (1H, bs); 7.92 (1H, d, J 7.8 Hz); 7.87 (2H, d, J 8.1 Hz); 7.85 (1H, t, J 7.8 Hz); 7.78 (1H, d, J 7.9 Hz); 7.55 (2H, d, J 8.2 Hz); 4.66-4.55 (2H, m); 3.17 (3H, s); 2.44 (3H, s); 2.33 (3H, s); 2.17 (3H, s)

APCI-MS m/z: 560.2 [MH$^+$].

EXAMPLE 63

N-(Cyclohexylmethyl)-6-methyl-2-oxo-5-phenyl-1-[3-(trifluoromethyl)phenyl]-1,2-dihydropyridine-3-carboxamide a) Ethyl 6-methyl-2-oxo-1-[3-(trifluoromethyl)phenyl]-1,2-dihydropyridine-3-carboxylate A suspension of 6-methyl-2-oxo-1-[3-(trifluoromethyl)phenyl]-1,2-dihydropyridine-3-carboxylic acid (Example 1 (b), 13.1 g, 43.9 mmol), sodium carbonate (5.2 g, 48.3 mmol) and iodoethane (10.6 g, 67.7 mmol) in NMP (60 ml) was stirred at ambient temperature for 19 h under a nitrogen atmosphere. The reaction mixture was partitioned between ethyl acetate and water. The organic phase was collected, washed with water and brine, dried over sodium sulphate, filtered and concentrated in vacuo. The residue was purified by flash chromatography on silica eluting with tert-butyl methyl ether/methanol (10:0.4) to give the title compound as a light brown solid (12.5 g, 87%).

$^1$H NMR (CDCl$_3$): δ 8.21 (1H, d, J 7.4 Hz); 7.75 (1H, d, J 7.8 Hz); 7.68 (1H, t, J 7.8 Hz); 7.49 (1H, s); 7.42 (1H, d, J 7.8 Hz); 6.25 (1H, d, J 7.4 Hz); 4.36 (2H, q, J 7.2 Hz); 2.03 (3H, s); 1.37 (3H, t, J 7.2 Hz).

APCI-MS m/z: 326.1 [MH$^+$].

b) Ethyl 5-iodo-6-methyl-2-oxo-1-[3-(trifluoromethyl)phenyl]-1,2-dihydropyridine-3-carboxylate N-Iodosuccinimide (6.89 g, 30.6 mmol) was added to a solution of ethyl 6-methyl-2-oxo-1-[3-(trifluoromethyl)phenyl]-1,2-dihydropyridine-3-carboxylate (9.9 g, 30.5 mmol) in DCM (45 ml) and TFA (38 ml) under a nitrogen atmosphere. After 19 h stirring at ambient temperature the solvent was concentrated in vacuo. Saturated aqueous sodium hydrogen carbonate solution and ethyl acetate were added to the residue to neutralize the remaining TFA. The organic phase was collected, washed with water and brine, dried over sodium sulfate, filtered and concentrated in vacuo. The residue was purified by flash chromatography on silica eluting with DCM/methanol (10:0.2) to give the title compound as a yellow solid (11.4 g, 83%).

$^1$H NMR (CDCl$_3$): δ 8.52 (1H, s); 7.76 (1H, d, J 7.8 Hz); 7.69 (1H, t, J 7.9 Hz); 7.46 (1H, s); 7.38 (1H, d, J 7.7 Hz); 4.36 (2H, q, J 7.1 Hz); 2.26 (3H, s); 1.37 (3H, t, J 7.2 Hz).

APCI-MS m/z: 452.0 [MH$^+$].

c) Ethyl 6-methyl-2-oxo-5-phenyl-1-[3-(trifluoromethyl)phenyl]-1,2-dihydropyridine-3-carboxylate Ethyl 5-iodo-6-methyl-2-oxo-1-[3-(trifluoromethyl)phenyl]-1,2-dihydropyridine-3-carboxylate (2.6 g, 5.76 mmol), phenyltributylstannane (2.24 mg, 6.10 mmol), tetrakis(triphenylphosphine)palladium(0) (17.3 mg, 0.02 mmol), toluene (15 ml) and anhydrous DME (1.5 ml) were placed in a Schlenk vessel equipped with a magnetic stirring bar. The vessel was purged with argon, sealed and heated at 100° C. overnight. After cooling to room temperature, the mixture was partitioned between ethyl acetate and water. The organic layer was washed with water and brine, dried over sodium sulfate, filtered and concentrated in vacuo. The residue was purified by preparative HPLC to give the title compound as a white solid (0.8 g, 35%).

$^1$H NMR (CDCl$_3$): δ 8.26 (1H, s); 7.72 (2H, m); 7.56 (1H, s); 7.51-7.36 (4H, m); 7.34-7.28 (2H, m); 4.37 (2H, q, J 7.1 Hz); 1.97 (3H, s); 1.37 (3H, t).

APCI-MS m/z: 402.3 [MH$^+$].

d) 6-Methyl-2-oxo-5-phenyl-1-[3-(trifluoromethyl)phenyl]-1,2-dihydropyridine-3-carboxylic acid Aqueous 2M sodium hydroxide solution (2.5 ml, 5.0 mmol) was added to a solution of ethyl 6-methyl-2-oxo-5-phenyl-1-[3-(trifluoromethyl)phenyl]-1,2-dihydropyridine-3-carboxylate (0.85 g, 2.12 mmol) in THF (5 ml), methanol (3 ml) and water (1 ml). The reaction mixture was stirred at room temperature for 2 h and then concentrated in vacuo. Acetonitrile (3 ml) was added to the residue and the solution was acidified using TFA. The resulting solid was collected by filtration, washed with water and acetone and air dried to give the title compound as white solid (0.62 g, 78%).

$^1$H NMR (CDCl$_3$): δ 13.75 (1H, s); 8.59 (1H, s); 7.87 (1H, d, J 8.1 Hz); 7.80 (1H, t, J 7.9 Hz); 7.61 (1H, s); 7.54 (1H, d, J 7.6 Hz); 7.51-7.40 (3H, m); 7.31 (2H, m); 2.08 (3H, s).

APCI-MS m/z: 374.2 [MH$^+$].

e) N-(Cyclohexyl-6-methyl-2-oxo-5-phenyl-1-[3-(trifluoromethyl)phenyl]-1,2-dihydropyridine-3-carboxamide (Cyclohexylmethyl)amine in NMP (135 μl, 0.3M, 0.04 mmol) was added to a mixture of 6-methyl-2-oxo-5-phenyl-1-[3-(trifluoromethyl)-phenyl]-1,2-dihydro-pyridine-3-carboxylic acid (12 mg, 0.03 mmol), HATU (15 mg, 0.04 mmol), HOAT (7 mg, 0.04 mmol) and DIEA (13 mg, 0.1 mmol) in NMP (160 μl). The reaction mixture was stirred for 17 h at room temperature. The solvent was removed in vacuo, and the residue was dissolved in acetonitrile/water, 50/50, to a total volume of 1.6 ml, and purified using preparative HPLC to give the title compound (7 mg, 50%).

RT (C$_{18}$, UV 220 nm): 7.0 min.

APCI-MS m/z: 469.1 [MH$^+$].

Using the general procedure described in Example 63 and the appropriate amine, the compounds of Examples 64 to 90 were prepared.

EXAMPLE 64

6-Methyl-N-(2-morpholin-4-ylethyl)-2-oxo-5-phenyl-1-[3-(trifluoromethyl)-phenyl]-1,2-dihydropyridine-3-carboxamide RT (C$_{18}$, UV 220 nm): 4.6 min.

APCI-MS m/z: 486.2 [MH$^+$].

EXAMPLE 65

6-Methyl-2-oxo-5-phenyl-N-(1H-1,2,4-triazol-3-yl)-1-[3-(trifluoromethyl)phenyl]-1,2-dihydropyridine-3-carboxamide RT (C$_{18}$, UV 220 nm): 5.2 min.

APCI-MS m/z: 440.2 [MH$^+$].

EXAMPLE 66

N-[2-(1H-Indol-3-yl)ethyl]-6-methyl-2-oxo-5-phenyl-1-[3-(trifluoromethyl)-phenyl]-1,2-dihydropyridine-3-carboxamide RT (C$_{18}$, UV 220 nm): 6.5 min.

APCI-MS m/z: 516.2 [MH$^+$].

EXAMPLE 67

6-Methyl-2-oxo-5-phenyl-N-(1-phenylethyl)-1-[3-(trifluoromethyl)phenyl]-1,2-dihydropyridine-3-carboxamide RT (C$_{18}$, UV 220 nm): 6.8 min.

APCI-MS m/z: 477.2 [MH$^+$].

EXAMPLE 68

6-Methyl-2-oxo-5-phenyl-N-(2-phenylethyl)-1-[3-(trifluoromethyl)phenyl]-1,2-dihydropyridine-3-carboxamide RT (C$_{18}$, UV 220 nm): 6.7 min.

APCI-MS m/z: 477.2 [MH$^+$].

EXAMPLE 69

6-Methyl-2-oxo-5-phenyl-N-[(2R)-2-phenylcyclopropyl]-1-[3-(trifluoromethyl)-phenyl]-1,2-dihydropyridine-3-carboxamide RT (C$_{18}$, UV 220 nm): 6.9 min.

APCI-MS m/z: 489.2 [MH$^+$].

EXAMPLE 70

N-(2,3-Dihydro-1H-inden-2-yl)-6-methyl-2-oxo-5-phenyl-1-[3-(trifluoromethyl)-phenyl]-1,2-dihydropyridine-3-carboxamide RT (C$_{18}$, UV 220 nm): 6.8 min.

APCI-MS m/z: 489.2 [MH$^+$].

EXAMPLE 71

N-[(1-Ethylpyrrolidin-2-yl)methyl]-6-methyl-2-oxo-5-phenyl-1-[3-(trifluoro-methyl)phenyl]-1,2-dihydropyridine-3-carboxamide RT (C$_H$, UV 220 nm): 4.7 min.

APCI-MS m/z: 484.2 [MH$^+$].

EXAMPLE 72

6-Methyl-N-(1-naphthylmethyl)-2-oxo-5-phenyl-1-[3-(trifluoromethyl)phenyl]-1,2-dihydropyridine-3-carboxamide RT ($C_{18}$, UV 220 nm): 7.0 min.,
APCI-MS m/z: 513.2 [MH$^+$].

EXAMPLE 73

N-(1,3-Benzodioxol-5-ylmethyl)-6-methyl-2-oxo-5-phenyl-1-[3-(trifluoromethyl)-phenyl]-1,2-dihydropyridine-3 carboxamide RT ($C_{18}$, UV 220 nm): 6.5 min.
APCI-MS m/z: 507.2 [MH$^+$].

EXAMPLE 74

N-(2-Chloro-4-fluorobenzyl)-6-methyl-2-oxo-5-phenyl-1-[3-(trifluoromethyl)-phenyl]-1,2-dihydropyridine-3-carboxamide RT ($C_{18}$, UV 220 nm): 7.0 min.
APCI-MS m/z: 515.2 [MH$^+$].

EXAMPLE 75

6-Methyl-2-oxo-5-phenyl-N-(2-thienylmethyl)-1-[3-(trifluoromethyl)phenyl]-1,2-dihydropyridine-3-carboxamide RT ($C_{18}$, UV 220 nm): 6.5 min.
APCI-MS m/z: 469.1 [MH$^+$].

EXAMPLE 76

N-(2-Cyclohex-1-en-1-ylethyl)-6-methyl-2-oxo-5-phenyl-1-[3-trifluoromethyl)-phenyl]-1,2-dihydropyridine-3-carboxamide RT ($C_{18}$, UV 220 nm): 7.2 min.
APCI-MS m/z: 481.3 [MH$^+$].

EXAMPLE 77

6-Methyl-2-oxo-N-(4-phenoxybenzyl)-5-phenyl-1-[3-(trifluoromethyl)phenyl]-1,2-dihydropyridine-3-carboxamide RT ($C_{18}$, UV 220 nm): 7.3 min.
APCI-MS m/z: 555.2 [MH$^+$].

EXAMPLE 78

N-[(2,5-Dimethyl-3-furyl)methyl]-6-methyl-2-oxo-5-phenyl-1-[3-(trifluoro-methyl)phenyl]-1,2-dihydropyridine-3-carboxamide APCI-MS m/z: 481.4 [MH$^+$].

EXAMPLE 79

N-{2-[4-(Aminosulfonyl)phenyl]ethyl}-6-methyl-2-oxo-5-phenyl-1-[3-(trifluoro-methyl)phenyl]-1,2-dihydropyridine-3-carboxamide RT ($C_{18}$, UV 220 nm): 5.8 min.
APCI-MS m/z: 556.1 [MH$^+$].

EXAMPLE 80

6-Methyl-2-oxo-5-phenyl-N-[4-1H-pyrazol-1-yl)benzyl]-1-[3-(trifluoromethyl)-phenyl]-1,2-dihydropyridine-3-carboxamide RT ($C_{18}$, UV 220 nm): 6.4 min.
APCI-MS m/z: 529.1 [MH$^+$].

EXAMPLE 81

6-Methyl-2-oxo-N-phenoxy-5-phenyl-1-[3-(trifluoromethyl)phenyl]-1,2-dihydro-pyridine-3-carboxamide RT ($C_{18}$, UV 220 nm): 6.6 min.
APCI-MS m/z: 465.1 [MH$^+$].

EXAMPLE 82

N-[(6-Fluoro-4H-1,3-benzodioxin-8-yl)methyl]-6-methyl-2-oxo-5-phenyl-1-[3-(trifluoromethyl)phenyl]-1,2-dihydropyridine-3-carboxamide RT ($C_{18}$, UV 220 nm): 6.6 min.
APCI-MS m/z: 539.2 [MH$^+$].

EXAMPLE 83

6-Methyl-2-oxo-5-phenyl-N-[2-(tetrahydro-2H-pyran-4-yl)ethyl]-1-[3-(trifluoro-methyl)phenyl]-1,2-dihydropyridine-3-carboxamide RT ($C_{18}$, UV 220 nm): 6.0 min.
APCI-MS m/z: 485.2 [MH$^+$].

EXAMPLE 84

6-Methyl-2-oxo-5-phenyl-N-[3-(1H-pyrazol-1-yl)propyl]-1-[3-trifluoromethyl-phenyl]-1,2-dihydropyridine-3-carboxamide RT ($C_{18}$, UV 220 nm): 5.7 min.
APCI-MS m/z: 481.1 [MH$^+$].

EXAMPLE 85

6-Methyl-N-[(1-methyl-1H-pyrazol-4-yl)methyl]-2-oxo-5-phenyl-1-[3-trifluoro-methyl)phenyl]-1,2-dihydropyridine-3-carboxamide RT ($C_{18}$, UV 220 nm): 5.4 min.
APCI-MS m/z: 467.2 [MH$^+$].

EXAMPLE 86

6-Methyl-2-oxo-5-phenyl-N-[(1-phenyl-1H-pyrazol-4-yl)methyl]-1-[3-(trifluoro-methyl)phenyl]-1,2-dihydropyridine-3-carboxamide RT ($C_{18}$, UV 220 nm): 6.5 min.
APCI-MS m/z: 529.1 [MH$^+$].

EXAMPLE 87

N-[(5-Methoxy-4-oxo-4H-pyran-2-yl)methyl]-6-methyl-2-oxo-5-phenyl-1-[3-(trifluoro methyl)phenyl]-1,2-dihydropyridine-3-carboxamide RT ($C_{18}$, UV 220 nm): 5.4 min.
APCI-MS m/z: 511.1 [MH$^+$].

EXAMPLE 88

N-(3-Azepan-1-ylpropyl)-6-methyl-2-oxo-5-phenyl-1-[3-(trifluoromethyl)phenyl]-1,2-dihydropyridine-3-carboxamide RT ($C_{18}$, UV 220 nm): 5.0 min.
APCI-MS m/z: 512.3 [MH$^+$].

EXAMPLE 89

N-(4-Cyanobenzyl)-6-methyl-2-oxo-5-phenyl-1-[3-(trifluoromethyl)phenyl]-1,2-dihydropyridine-3-carboxamide RT ($C_{18}$, UV 220 nm): 6.4 min.
APCI-MS m/z: 488.2 [MH$^+$].

EXAMPLE 90

6-Methyl-2-oxo-N-[3-(5-oxo-4,5-dihydro-1H-pyrazol-4-yl)propyl]-5-phenyl-1-[3-(trifluoromethyl)phenyl]-1,2-dihydropyridine-3-carboxamide RT ($C_{18}$, UV 220 nm): 5.0 min.
APCI-MS m/z: 497.2 [MH$^+$].

EXAMPLE 91

6-Methyl-5-(2-methyl-2H-pyrazol-3-yl)-2-oxo-1-(3-trifluoromethyl-phenyl)-1,2-dihydro-pyridine-3-carboxylic acid (3-methyl-isoxazol-5-ylmethyl)-amide a) 6-Methyl-2-oxo-1-(3-trifluoromethyl-phenyl)-1,2-dihydro-pyridine-3-carboxylic acid prop-2-ynylamide $SOCl_2$ (10 ml) was added in one portion to a solution of 6-methyl-2-oxo-1-(3-trifluoromethyl-phenyl)-1,2-dihydro-pyridine-3-carboxylic acid (Example 1 (b), 1.0 g, 3.36 mmol) in DCM (10 ml). The solution was stirred magnetically for 1 h at which time LC-MS showed complete conversion. The crude mixture was evaporated in vacuo, giving the intermediate acid chloride as a yellow solid. This solid was dissolved in 1,4-dioxane (10 ml, dried over molecular sieves) and propargylamine (0.23 g, 4.17 mmol) and triethylamine (1 ml) were added. The mixture was stirred for 10 minutes, and LC-MS showed complete formation of the product. The mixture was concentrated in vacuo and the residue was purified on silica giving the subtitle compound (0.93 g, 83%) as a yellowish solid after evaporating the pure fractions.

$^1$H NMR (DMSO-$d_6$): δ 9.82 (1H, t, J 7.4 Hz); 8.36 (1H, d, J 7.7 Hz); 7.91 (1H, s); 7.90 (1H, d); 7.82 (1H, t, J 8.1 Hz); 7.73 (1H, d, J 8.1 Hz); 6.63 (1H, d, J 7.5 Hz); 4.10-4.04 (2H, m); 3.11 (1H, t, J 2.4 Hz); 2.02 (3H, s).
APCI-MS m/z: 335.1 [MH$^+$].

b) 6-Methyl-2-oxo-1-(3-trifluoromethylphenyl)-1,2-dihydro-pyridine-3-carboxylic acid (3-methyl-isoxazol-5-ylmethyl)-amide The compound obtained in step (a) (0.050 g, 0.15 mmol) was dissolved in EtOAc (15 ml) under magnetic stirring. To this solution was added N-hydroxyacetimidoyl chloride (0.15 g, 1.6 mmol), water (0.3 ml) and $KHCO_3$ (0.16 g, 1.6 mmol). The mixture was stirred for 2 days at which time LC-MS showed 90% conversion. The reaction was stopped and the mixture was partitioned between EtOAc (25 ml) and water (25 ml). The organic phase was washed (water, brine) and dried. Filtration and evaporation gave a crude mixture which was purified by chromatography on silica. Freeze-drying the pure fractions afforded the subtitle compound (0.031 g, 53%) as a white powder.

$^1$H NMR (DMSO-$d_6$): δ 9.86 (1H, t, J 5.9 Hz); 8.37 (1H, d, j 7.6 Hz); 7.91 (1H, s); 7.90 (1H, d); 7.81 (1H, t, J 7.9 Hz); 7.72 (1H, d, J 7.7 Hz); 6.63 (1H, d, J 7.6 Hz); 6.15 (1H, s); 4.58 (2H, d, 5.9 Hz); 2.17 (3H, s); 2.03 (3H, s).
APCI-MS m/z: 392.2.2 [MH$^+$].

c) 6-Methyl-5-(2-methyl-2H-pyrazol-3-yl)-2-oxo-1-(3-trifluoromethyl-phenyl)-1,2-dihydro-pyridine-3-carboxylic acid (3-methyl-isoxazol-5-ylmethyl)-amide The compound obtained in step (b) (0.019 g, 0.048 mmol) was dissolved in DCM (1.5 ml) and TFA (1.5 ml). A magnetic stirrer bar and N-iodosuccinimide (0.011 g, 0.048 mmol) were added and the vial was sealed and stirred for 90 minutes at room temperature. LC-MS showed complete conversion of the starting material. The volatiles were removed in vacuo and the crude material was purified on silica, giving the 5-iodinated intermediate (0.014 g). This intermediate was dissolved in DME (2.5 ml) in a vial, and 5-trimethylstannyl-1-methyl-1H-pyrazole (0.02 g, 0.082 mmol) and Pd(PPh$_3$)$_4$ (0.010 g, 8.7 mol) were added. The vial was sealed and the mixture was heated (130° C.) with stirring for 1 h. LC-MS now showed complete conversion of the iodide to a product with the expected MW. Evaporation and purification by preparative HPLC afforded the title compound (0.008 g, 35%, two steps) as a white solid after freeze-drying the pure fractions.

$^1$H NMR (DMSO-$d_6$): δ 9.82 (1H, t, J 6.0 Hz); 8.21 (1H, s); 8.02 (1H, s); 7.92 (1H, d, J 7.6 Hz); 7.88-7.78 (2H, m); 7.53 (1H, d, J 1.9 Hz); 6.33 (1H, d, J 1.9 Hz); 6.16 (1H, s); 4.60 (2H, d, J 6.1 Hz); 3.72 (3H, s); 2.17 (3H, s); 1.82 (3H, s).
APCI-MS m/z: 472.1 [MH$^+$].

EXAMPLE 92

6-Methyl-5-(2-methyl-2H-pyrazol-3-yl)-2-oxo-1-(3-trifluoromethyl-phenyl)-1,2-dihydro-pyridine-3-carboxylic acid (5-methanesulfonylmethyl-[1,2,4]oxadiazol-3-ylmethyl)-amide a) 6-Methyl-5-(2-methyl-2H-pyrazol-3-yl)-2-oxo-1-(5-trifluoromethyl-phenyl)-1,2-dihydro-pyridine-3-carboxylic acid Ethyl 5-iodo-6-methyl-2-oxo-1-[3-(trifluoromethyl)phenyl]-1,2-dihydropyridine-3-carboxylate (Example 63 (b), 0.77 g, 1.7 mmol), DME (25 ml), 5-trimethylstannyl-1-methyl-1H-pyrazole (0.49 g, 2 mmol), Pd(PPh$_3$)$_4$ (0.10 g, 0.087 mmol) and a magnetic stirrer bar were placed in a pressure safe glass vessel. The vessel was sealed and heated (130° C.) with stirring overnight. LC-MS showed complete formation of the product. The mixture was allowed to cool, and was then diluted with EtOAc (50 ml), washed with water and brine, and further dried with Na$_2$SO$_4$. Filtration and evaporation and subsequent purification on silica gave the intermediate ester. This material was dissolved in THF (10 ml) and water (5 ml) and NaOH (2M, 1 ml, 2 mmol) was added. The mixture was stirred at 50° C. for 1 h. The TIM was evaporated off and the aqueous solution was acidified whereupon the product precipitated. The product was extracted with EtOAc. The extracts were dried (Na$_2$SO$_4$) and evaporated to give the carboxylic acid (0.3 g, 47%) as yellowish solid.

$^1$H NMR (DMSO-d$_6$): δ 13.80 (1H, s); 8.25 (1H, s); 8.07 (1H, s); 7.99-7.93 (1H, m); 7.90-7.85 (2H, m); 7.54 (1H, d, J 1.8 Hz); 6.36 (1H, d, J 1.8 Hz); 3.73 (3H; s); 1.86 (3H, s).

APCI-MS m/z: 363.3 [MH$^+$].

b) 6-Methyl-5-(2-methyl-2H-pyrazol-3-yl)-2-oxo-1-(3-trifluoromethyl-phenyl)-1,2-dihydro-pyridine-3-carboxylic acid cyanomethyl amide The compound obtained in step (a) (0.2 g, 0.53 mmol) was dissolved in 1,4-dioxane (5 ml), HBTU (0.19 g, 0.5 mmol) and DMA (0.32 g, 2.5 mmol). The mixture was stirred for 10 minutes and aminoacetonitrile hydrochloride (0.55 g, 0.6 mmol) was added. After 1 h the mixture was evaporated and the residue purified by chromatography on silica to give the amide (0.15 g, 72%) as a white solid.

$^1$H NMR (DMSO-d$_6$): δ 9.75 (1H, t, J 5.9 Hz); 8.22 (1H, s); 8.03 (1H, s); 7.93 (1H, d, J 7.25 Hz); 7.88-7.81 (2H, m); 7.54 (1H, d, J 1.8 Hz); 6.34 (1H, d, J 1.8 Hz); 4.31 (2H, d, J 5.9 Hz); 3.72 (3H, s); 1.83 (3H, s).

APCI-MS m/z: 416.2 [MH$^+$]. Retention time 2.2 minutes.

c) 6-Methyl-5-(2-methyl-2H-pyrazol-3-yl)-2-oxo-1-(3-trifluoromethylphenyl)-1,2-dihydro-pyridine-3-carboxylic acid (N-hydroxycarbamimidoylmethyl)-amide The compound obtained in step (b) (0.21 g, 0.5 mmol), hydroxylamine hydrochloride (0.070 g, 1 mmol), NaOAc (0.080 g, 1 mmol), EtOH (2 ml) and a magnetic stirrer bar were placed in a vial. The vial was sealed and the mixture was heated (90° C.) with stirring for 3 h. LC-MS showed complete conversion of the nitrile into a mixture of two compounds with the masses 449 and 465 ([MH$^+$]). Evaporation and purification on preparative HPLC gave a mixture of the two products containing 90% of the desired compound. This material was used without further purification.

APCI-MS m/z: 449.2 [MH$^+$].

d) 6-Methyl-5-(2-methyl-2H-pyrazol-3-yl)-2-oxo-1-(3-trifluoromethylphenyl)-1,2-dihydro-pyridine-3-carboxylic acid (5-methanesulfonylmethyl-[1,2,4]oxadiazol-3-ylmethyl)-amide The compound obtained in step (c) (0.019 g, 0.042 mmol) was dissolved in 1,4-dioxane (dry, 1 ml) and CH$_3$CN (dry, 1 ml) in a vial. 2-Methanesulfonylacetylchloride (prepared according to literature procedures, 0.015 g, 0.095 mmol) was added, the vial was sealed and the mixture was stirred at room temperature for 1 h. Isolation of this material and purification by preparative HPLC gave, after freeze-drying, the required intermediate (0.011 g). This solid was dissolved in 1,4-dioxane (2 ml) in a vial and acetic acid (5 drops) was added. The vial was sealed and the mixture was heated (90° C.) with stirring for 5 h (monitoring the reaction by LC-MS). When reaction was complete, the mixture was allowed to cool and the volatiles were removed in vacuo. The crude mixture was purified by preparative HPLC to give the title compound (0.008 g, 35%, 2 steps) as a white solid after freeze-drying the pure fractions.

$^1$H NMR (DMSO-d$_6$): δ 9.93 (1H, t, J 6.0 Hz); 8.21 (1H, s); 8.04 (1H, s); 7.93 (1H, d, J 7.93 Hz); 7.88-7.82 (2H, m); 7.53 (1H, d, J 1.9 Hz); 6.33 (1H, d, J 1.9 Hz); 5.18 (2H, s); 4.70 (2H, d, J 6.0 Hz); 3.72 (3H, s); 3.19 (3H, s); 1.83 (3H, s).

APCI-MS m/z: 551.2 [MH$^+$].

EXAMPLE 93

6-Methyl-5-(2-methyl-2H-pyrazol-3-yl)-2-oxo-1-(3-trifluoromethyl-phenyl)-1,2-dihydro-pyridine-3-carboxylic acid ([1,2,4]oxadiazol-3-ylmethyl)-amide 6-Methyl-5-(2-methyl-2H-pyrazol-3-yl)-2-oxo-1-(3-trifluoromethyl-phenyl)-1,2-dihydro-pyridine-3-carboxylic acid (N-hydroxycarbamimidoylmethyl)-amide (Example 92 (c), 0.017 g, 0.038 mmol), triethyl-orthoformate (1 ml) and a magnetic stirrer bar were placed in a vial. The vial was sealed and the mixture was heated (130° C.) with stirring for 3 h. LC-MS showed complete conversion of the starting material to a product with the expected MW. The volatiles were removed in vacuo and the residue was purified by preparative HPLC. Pure fractions were freeze-dried to give the title compound (0.009 g, 53%) as a white solid.

$^1$H NMR (DMSO-d$_6$): δ 9.92 (1H, t, J 5.9 Hz); 9.54 (1H, s); 8.21 (1H, s); 8.03 (1H, s); 7.93 (1H, d, J 7.0 Hz); 7.88-7.82 (2H, m), 7.53 (1H, d, J 1.8 Hz); 6.33 (1H, d, J 1.8 Hz); 4.69 (2H, d, J 5.9 Hz); 3.72 (3H, s); 1.83 (3H, s).

APCI-MS m/z: 459.1 [MH$^+$].

EXAMPLE 94

6-Methyl-5-(1-methyl-1H-pyrazol-5-yl)-N-{[5-(methylsulfonyl)pyridin-2-methyl}-2-oxo-(trifluoromethyl)phenyl]-1,2-dihydropyridine-3-carboxamide a) 5-(Methylthio)pyridine-2-carbonitrile 5-Bromo-pyridine-2-carbonitrile (2.63 g, 13.7 mmol), sodium methanethiolate (1.44 g, 20.5 mmol), potassium carbonate (3.79 g, 27.4 mmol) in NMP (60 ml) were stirred in a sealed flask overnight. The mixture was partitioned between ethyl acetate and water. The organic phase was washed with water several times, brine and dried over sodium sulphate. The solvent was removed in vacuo to afford the title compound as a yellow solid (2.0 g, 99%).

$^1$H NMR (CD$_3$OD): δ 8.54 (1H, d, J 2.3 Hz); 7.83-7.71 (2H, m); 2.60 (3H, s).

b) 5-(Methylsulfonyl)pyridine-2-carbonitrile 5-(Methylthio)pyridine-2-carbonitrile (2.0 g, 13.3 mmol) was dissolved in DCM (20 ml) and cooled to −15° C. and 3-chloroperoxybenzoic acid (6.75 g, 27.4 mmol) was added in portions while the temperature was kept between −15° C. to −10° C. When the addition was complete, the cooling bath was removed and the mixture was stirred at room temperature for 2 h. 2M KOH and DCM were added. The organic phase was separated, washed twice with 2M KOH, water and brine, dried over sodium sulphate and evaporated to afford the title compound as a white solid (2.15 g, 89%).

$^1$H NMR (CD$_3$OD): δ 9.22 (1H, d, J 2.3 Hz); 8.54 (1H, dd, J 8.1, 2.3 Hz); 8.13 (1H, d, J 8.3 Hz); 3.27 (3H, s).

c) {[5-(Methylsulfonyl)pyridin-2-yl]methyl}amine hydrochloride 5-(Methylsulfonyl)pyridine-2-carbonitrile (2.15 g, 11.8 mmol) was dissolved in methanol (230 ml). 6M HCl (1 ml) and 10% palladium on carbon (2.34 mg) were added and the mixture was stirred under an atmosphere pressure of hydrogen overnight. The catalyst was removed by filtration through celite and the solvent was evaporated, water was added and the solution was freeze-dried to afford the title compound as a yellow powder (2.34 g, 89%).

$^1$H NMR (CD$_3$OD); δ 9.10 (1H, d, J 2.2 Hz); 8.36 (1H, dd, J 8.2, 2.4 Hz); 7.68 (1H, d, J 8.8 Hz); 4.29 (2H, s); 3.22 (3H, s).

d) 6-Methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide HBTU (30 mg, 0.079 mmol) was added to {[5-(methylsulfonyl)pyridin-2-yl]methyl}amine hydrochloride (20 mg, 0.090 mmol), 6-methyl-5-(2-methyl-2H-pyrazol-3-yl)-2-oxo-1-(3-trifluoromethyl-phenyl)-1,2-dihydro-pyridine-3-carboxylic acid (Example 92 (a), 27 mg, 0.072 mmol) and DMA (23 μl, 0.31 mmol) in NMP (0.25 ml) and the mixture was stirred in a sealed vial overnight. The product was purified by preparative HPLC and freeze-dried to give the title compound as a white solid (8 mg, 20%).

$^1$H NMR (CD$_3$OD): δ 9.01 (1H, d, J 2.2 Hz); 8.37 (1H, s); 8.28 (1H, dd, J 8.4, 2.3 Hz); 7.93-7.80 (3H, m); 7.73-7.60 (2H, m); 7.57 (1H, d, J 2.0 Hz); 6.38 (1H, d, J 2.0 Hz); 4.83 (2H, s); 3.79 (3H, s); 3.18 (3H, s); 1.94 (3H, s).

APCI-MS m/z: 546.1 [MH$^+$].

EXAMPLE 95

5-(3,5-Dimethylisoxazol-4-yl)-6-methyl-N-{[5-(methylsulfonyl)pyridin-2-yl]methyl}-2-oxo-1-[3-(trifluoromethyl)phenyl]-1,2-dihydropyridine-3-carboxamide a) 5-(3,5-Dimethylisoxazol-4-yl)-6-methyl-2-oxo-1-[3-(trifluoromethyl)phenyl]-1,2-dihydropyridine-3-carboxylic acid Ethyl 5-iodo-6-methyl-2-oxo-1-[3-(trifluoromethyl)phenyl]-1,2-dihydropyridine-3-carboxylate (Example 63 (b), 0.72 g, 1.6 mmol), DME (20 ml), 3,5-dimethylisoxazolyl-4-boronic acid (0.28 g, 2 mmol), Pd$_2$(dba)$_3$ (0.036 g, 0.039 mmol), PPh$_3$ (0.062 g, 0.23 mmol), 2M Na$_2$CO$_3$ (10 ml) and a magnetic stirrer bar were placed in a pressure safe glass vessel. The vessel was sealed and heated (120° C.) with stirring overnight. LC-MS showed complete formation of the required product (including hydrolysis of the ester). The mixture was allowed to cool, the aqueous phase was acidified, and the organic phase was diluted with EtOAc (50 ml) and the phases were allowed to separate. The organic phase was washed with water and brine, and further dried with Na$_2$SO$_4$. Filtration and evaporation gave a crude mixture which was purified by preparative HPLC giving the carboxylic acid (0.27 g, 43%) as yellowish solid.

$^1$H NMR (DMSO-d$_6$): δ 13.93 (1H, s); 8.25 (1H, s); 8.07 (1H, s); 7.99-7.93 (1H, m); 7.89-7.85 (2H, m); 2.35 (3H, m); 2.15-2.10 (3H, m); 1.85 (3H, s).

APCI-MS m/z: 393.1 [MH$^+$].

b) 5-(3,5-Dimethylisoxazol-4-yl)-6-methyl-N-{[5-(methylsulfonyl)pyridin-2-yl]methyl}-2-oxo-1-[3-(trifluoromethyl)phenyl]-1,2-dihydropyridine-3-carboxamide The title compound was prepared from 5-(3,5-dimethylisoxazol-4-yl)-6-methyl-2-oxo-1-[3-(trifluoromethyl)phenyl]-1,2-dihydropyridine-3-carboxylic acid using a method analogous to that described in Example 94.

$^1$H NMR (CD$_3$OD): δ 9.01 (1H, d, J 1.8 Hz); 8.31 (1H, s); 8.28 (1H, dd, J 8.2, 2.4 Hz); 7.92-7.80 (3H, m); 7.70 (1H, d, J 7.9 Hz); 7.62 (1H, d, J 8.2 Hz); 4.82 (2H, s); 3.18 (3H, s); 2.34 (3H, d, J 2.2 Hz); 2.18 (3H, d, J 2.0 Hz); 1.93 (3H, s).

APCI-MS m/z: 561.1 [MH$^+$].

Screen

Human Neutrophil Elastase Quenched-FRET Assay

The assay uses Human Neutrophil Elastase (FINE) purified from serum (Calbiochem art. 324681; Ref. Baugh, R. J. et al., 1976, Biochemistry. 15, 836-841). HNE was stored in 50 mM NaOAc, 200 mM NaCl, pH 5.5 with added 30% glycerol at −20° C. The protease substrate used was Elastase Substrate V Fluorogenic, MeOSuc-AAPV-AMC (Calbiochem art. 324740; Ref. Castillo, M. J. et al., 1979, Anal. Biochem. 99, 53-64). The substrate was stored in DMSO at −20° C. The assay additions were as follows: Test compounds and controls were added to black 96-well flat-bottom plates (Greiner 655076), 1 μL in 100% DMSO, followed by 30 μL HNE in assay buffer with 0.01% TritonX-100. The assay buffer constitution was: 100 mM Tris (pH 7.5) and 500 mM NaCl. The enzyme and the compounds were incubated at room temperature for 15 minutes. Then 30 μl substrate in assay buffer was added. The assay was stopped after 30 minutes incubation at room temperature by adding 60 μl stop solution (140 mM acetic acid, 200 mM sodium monochloroacetate, 60 mM sodium acetate, pH 4.3). Fluorescence was measured on a Wallac 1420 Victor 2 instrument at settings: Excitation 380 nm, Emission 460 nm. IC$_{50}$ values were determined using Xlfit curve fitting using model 205.

When tested in the above screen, the compounds of the Examples gave IC$_{50}$ values for inhibition of human neutrophil elastase activity of less than 30 μM, indicating that the compounds of the invention are expected to possess useful therapeutic properties. Specimen results are shown in the following Table:

| Compound | Inhibition of Human Neutrophil Elastase IC$_{50}$ (nM) |
| --- | --- |
| Example 2 | 46 |
| Example 5 | 48 |
| Example 1 | 47 |
| Example 32 | 3 |
| Example 36 | 17 |
| Example 46 | 7 |
| Example 91 | 12 |

The invention claimed is:
1. A compound of formula (I)

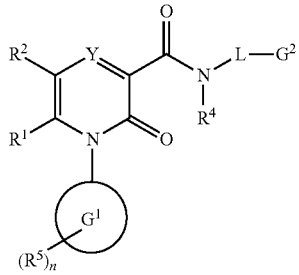

wherein:
Y represents $CR^3$ or N;
$R^1$ represents H or C1 to 6 alkyl;
$R^2$ represents phenyl or a five- or six-membered heteroaromatic ring containing 1 to 4 heteroatoms independently selected from O, S and N; said aromatic ring being optionally substituted by 1 to 3 substituents selected independently from OH, halogen, C1 to 6 alkyl, C1 to 6 alkoxy, $NR^{58}COR^{50}$, $COOR^{51}$, $COR^{52}$, $CONR^{53}R^{54}$ and $NR^{47}R^{48}$; said alkyl being optionally further substituted by OH, C1 to 6 alkoxy, CN or $CO_2R^{49}$;
$R^{47}$ and $R^{48}$ independently represent H, C1 to 6 alkyl or C2 to 6 alkanoyl;
$R^3$ represents H or F;
$G^1$ represents phenyl or a five- or six-membered heteroaromatic ring containing 1 to 3 heteroatoms independently selected from O, S and N;
$R^5$ represents H, halogen, C1 to 6 alkyl, CN, C1 to 6 alkoxy, $NO_2$, $NR^{14}R^{15}$, C1 to 3 alkyl substituted by one or more F atoms or C1 to 3 alkoxy substituted by one or more F atoms;
$R^{14}$ and $R^{15}$ independently represent H or C1 to 3 alkyl; said alkyl being optionally further substituted by one or more F atoms;
n represents an integer 1, 2 or 3 and when n represents 2 or 3, each $R^5$ group is selected independently;
$R^4$ represents H or C1 to 6 alkyl; said alkyl being optionally further substituted by OH or C1 to 6 alkoxy;
or $R^4$ and L are joined together such that the group —$NR^4L$ represents a 5 to 7 membered azacyclic ring optionally incorporating one further heteroatom selected from O, S and $NR^{16}$;
L represents C1 to 6 alkyl; said alkyl optionally incorporating a heteroatom selected from O, S and $NR^{16}$; and said alkyl being optionally further substituted by OH or OMe;
$G^2$ represents a monocyclic ring system selected from:
i) phenyl or phenoxy,
ii) a 5 or 6 membered heteroaromatic ring containing one to three heteroatoms independently selected from O, S and N,
iii) a C3 to 6 saturated or partially unsaturated cycloalkyl, or
iv) a C4 to 7 saturated or partially unsaturated heterocyclic ring containing one or two heteroatoms independently selected from O, $S(O)_p$ and $NR^{17}$ and optionally further incorporating a carbonyl group; or
$G^2$ represents a bicyclic ring system in which each of the two rings is independently selected from:
i) phenyl,
ii) a 5 or 6 membered heteroaromatic ring containing one to three heteroatoms independently selected from O, S and N,
iii) a C3 to 6 saturated or partially unsaturated cycloalkyl, or
iv) a C4 to 7 saturated or partially unsaturated heterocyclic ring containing one or two heteroatoms independently selected from O, $S(O)_p$ and $NR^{17}$ and optionally further incorporating a carbonyl group;
and the two rings are either fused together, or are bonded directly together or are separated by a linker group selected from O, $S(O)_q$ or $CH_2$,
said monocyclic or bicyclic ring system being optionally further substituted by one to three substituents independently selected from CN, OH, C1 to 6 alkyl, C1 to 6 alkoxy, halogen, $NR^{18}R^{19}$, $NO_2$, $OSO_2R^{38}$, $CO_2R^{20}$, $C(=NH)NH_2$, $C(O)NR^{21}R^{22}$, $C(S)NR^{23}R^{24}$, $SC(=NH)NH_2$, $NR^{31}C(=NH)NH_2$, $S(O)_sR^{25}$, $SO_2NR^{26}R^{27}$, C1 to 3 alkoxy substituted by one or more F atoms and C1 to 3 alkyl substituted by $SO_2R^{39}$, $NR^{56}R^{57}$ or by one or more F atoms;
or
$G^2$ may also represent H;
at each occurrence, p, q, s and t independently represent an integer 0, 1 or 2;
$R^{18}$ and $R^{19}$ independently represent H, C1 to 6 alkyl, formyl, C2 to 6 alkanoyl, $S(O)_tR^{32}$ or $SO_2NR^{33}R^{34}$; said alkyl group being optionally further substituted by halogen, CN, C1 to 4 alkoxy or $CONR^{41}R^{42}$;
$R^{25}$ represents H, C1 to 6 alkyl or C3 to 6 cycloalkyl; said alkyl group being optionally further substituted by one or more substituents selected independently from OH, CN, $CONR^{35}R^{36}$, $CO_2R^{37}$, $OCOR^{40}$, C3 to 6 cycloalkyl, a C4 to 7 saturated heterocyclic ring containing one or two heteroatoms independently selected from O, $S(O)_p$ and $NR^{43}$ and phenyl or a 5 or 6 membered heteroaromatic ring containing one to three heteroatoms independently selected from O, S and N; said aromatic ring being optionally further substituted by one or more substituents selected independently from halogen, CN, C1 to 4 alkyl, C1 to 4 alkoxy, OH, $CONR^{44}R^{45}$, $CO_2R^{46}$, $S(O)_sR^{55}$ and $NHCOCH_3$;
$R^{32}$ represents H, C1 to 6 alkyl or C3 to 6 cycloalkyl;
$R^{16}$, $R^{17}$, $R^{20}$, $R^{21}$, $R^{22}$, $R^{23}$, $R^{24}$, $R^{26}$, $R^{27}$, $R^{29}$, $R^{31}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{49}$, $R^{50}$, $R^{51}$, $R^{52}$, $R^{53}$, $R^{54}$, $R^{55}$, $R^{56}$, $R^{57}$ and $R^{58}$ independently represent H or C1 to 6 alkyl;
or a pharmaceutically acceptable salt thereof.
2. A compound of formula (I), according to claim 1, or a pharmaceutically acceptable salt thereof, wherein Y represents $CR^3$.
3. A compound of formula (I), according to claim 1, or a pharmaceutically acceptable salt thereof, wherein $G^1$ represents phenyl.
4. A compound of formula (I), of claim 1, or a pharmaceutically acceptable salt thereof, wherein $R^5$ represents Cl, $CH_3$, CN or $CF_3$.
5. A compound of formula (I), according to claim 1 selected from:
N-[4-(methylsulfonyl)benzyl]-2-oxo-5-phenyl-1-[3-(trifluoromethyl)phenyl]-1,2-dihydropyridine-3-carboxamide;
5-[4-(hydroxymethyl)phenyl]-6-methyl-N-[4-(methylsulfonyl)benzyl]-2-oxo-1-[3-(trifluoromethyl)phenyl]-1,2-dihydropyridine-3-carboxamide;

5-furan-3-yl-6-methyl-2-oxo-1-(3-trifluoromethylphenyl)-1,2-dihydro-pyridine-3-carboxylic acid 4-methanesulfonyl-benzylamide;

6'-methoxy-2-methyl-N-[4-(methylsulfonyl)benzyl]-6-oxo-1-[3-(trifluoromethyl)phenyl]-1,6-dihydro-3,3'-bipyridine-5-carboxamide;

5-(2-methoxypyrimidin-5-yl)-6-methyl-N-[4-(methylsulfonyl)benzyl]-2-oxo-1-[3-(trifluoromethyl)phenyl]-1,2-dihydropyridine-3-carboxamide;

5-[4-(acetylamino)phenyl]-6-methyl-N-[4-(methylsulfonyl)benzyl]-2-oxo-1-[3-(trifluoromethyl)phenyl]-1,2-dihydropyridine-3-carboxamide;

6-methyl-2-oxo-5-(1H-pyrrol-3-yl)-1-(3-trifluoromethylphenyl)-1,2-dihydro-pyridine-3-carboxylic acid 4-methanesulfonyl-benzylamide;

5-furan-2-yl-6-methyl-2-oxo-1-(3-trifluoromethylphenyl)-1,2-dihydro-pyridine-3-carboxylic acid 4-methanesulfonyl-benzylamide;

6-methyl-2-oxo-5-thiophen-3-yl-1-(3-trifluoromethylphenyl)-1,2-dihydro-pyridine-3-carboxylic acid 4-methanesulfonyl-benzylamide;

6-methyl-2-oxo-5-thiophen-2-yl-1-(3-trifluoromethylphenyl)-1,2-dihydro-pyridine-3-carboxylic acid 4-methanesulfonyl-benzylamide;

5-(3,5-dimethyl-isoxazol-4-yl)-6-methyl-2-oxo-1-(3-trifluoromethylphenyl)-1,2-dihydro-pyridine-3-carboxylic acid 4-methanesulfonyl-benzylamide;

5-(2,4-dimethoxy-pyrimidin-5-yl)-6-methyl-2-oxo-1-(3-trifluoromethylphenyl)-1,2-dihydro-pyridine-3-carboxylic acid 4-methanesulfonyl-benzylamide;

5-(2,4-dioxo-1,2,3,4-tetrahydro-pyrimidin-5-yl)-6-methyl-2-oxo-1-(3-trifluoromethyl-phenyl)-1,2-dihydro-pyridine-3-carboxylic acid 4-methanesulfonyl-benzylamide;

6-methyl-5-(5-methyl-[1,3,4]oxadiazol-2-yl)-2-oxo-1-(3-trifluoromethylphenyl)-1,2-dihydro-pyridine-3-carboxylic acid 4-methanesulfonyl-benzylamide;

6-methyl-2-oxo-5-(5-propyl-[1,3,4]oxadiazol-2-yl)-1-(3-trifluoromethylphenyl)-1,2-dihydro-pyridine-3-carboxylic acid 4-methanesulfonyl-benzylamide;

{5-[5-(4-methanesulfonyl-benzylcarbamoyl)-2-methyl-6-oxo-1-(3-trifluoromethyl-phenyl)-1,6-dihydro-pyridin-3-yl]-[1,3,4]oxadiazol-2-yl}-acetic acid ethyl ester;

5-(5-cyanomethyl-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

5-(5-amino-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

5-(5-amino-[1,3,4]thiadiazol-2-yl)-6-methyl-2-oxo-1-(3-trifluoromethylphenyl)-1,2-dihydro-pyridine-3-carboxylic acid 4-methanesulfonyl-benzylamide;

5-(5-ethylamino-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

5-(5-N,N-dimethylamino-[1,3,4]oxadiazol-2-yl)-6-methyl-2-oxo-1-(3-trifluoromethyl-phenyl)-1,2-dihydro-pyridine-3-carboxylic acid 4-methanesulfonyl-benzylamide;

6-methyl-N-[4-(methylsulfonyl)benzyl]-2-oxo-5-pyrazin-2-yl-1-[3-(trifluoro-methyl)phenyl]-1,2-dihydropyridine-3-carboxamide;

6-methyl-5-oxazol-2-yl-2-oxo-1-(3-trifluoromethylphenyl)-1,2-dihydro-pyridine-3-carboxylic acid 4-methanesulfonyl-benzylamide;

6-methyl-5-(1-methyl-1H-imidazol-2-yl)-2-oxo-1-(3-trifluoromethylphenyl)-1,2-dihydro-pyridine-3-carboxylic acid 4-methanesulfonyl-benzylamide;

6-methyl-2-oxo-5-(1H-pyrazol-4-yl)-1-(3-trifluoromethylphenyl)-1,2-dihydro-pyridine-3-carboxylic acid 4-methanesulfonyl-benzylamide;

6-methyl-N-[4-(methylsulfonyl)benzyl]-2-oxo-5-pyrimidin-2-yl-1-[3-(trifluoro-methyl)phenyl]-1,2-dihydropyridine-3-carboxamide;

6-methyl-5-(2-methyl-2H-pyrazol-3-yl)-2-oxo-1-(trifluoromethylphenyl)-1,2-dihydro-pyridine-3-carboxylic acid 4-methanesulfonyl-benzylamide;

6-methyl-5-(3-methylisoxazol-4-yl)-N-[4-(methylsulfonyl)benzyl]-2-oxo-1-[3-(trifluoromethyl)phenyl]-1,2-dihydropyridine-3-carboxamide;

6-methyl-5-(3-methyl-[1,2,4]oxadiazol-5-yl)-2-oxo-1-(3-trifluoromethylphenyl)-1,2-dihydro-pyridine-3-carboxylic acid 4-mathanesulfonyl-benzylamide;

6-methyl-5-(3-methylisoxazol-5-yl)-N-[4-(methylsulfonyl)benzyl]-2-oxo-1-[3-(trifluoromethyl)phenyl]-1,2-dihydropyridine-3-carboxamide;

5-(3,5-dimethylisoxazol-4-yl)-N-[4-(isopropylsulfonyl)benzyl]-6-methyl-2-oxo-1-[3-(trifluoromethyl)phenyl]-1,2-dihydropyridine-3-carboxamide;

5-(3,5-dimethylisoxazol-4-yl)-N-[4-(ethylsulfonyl)benzyl]-6-methyl-2-oxo-1-[3-(trifluoromethyl)phenyl]-1,2-dihydropyridine-3-carboxamide;

N-[4-(cyclopropylsulfonyl)benzyl]-5-(3,5-dimethylisoxazol-4-yl)-6-methyl-2-oxo-1-[3-(trifluoromethyl)phenyl]-1,2-dihydropyridine-3-carboxamide;

1-(3-cyanophenyl)-5-(3,5-dimethylisoxazol-4-yl)-6-methyl-N-[4-(methylsulfonyl)benzyl]-2-oxo-1,2-dihydro-pyridine-3-carboxamide;

1-(3-chlorophenyl)-5-(3,5-dimethyl-isoxazol-4-yl)-6-methyl-2-oxo-1,2-dihydro-pyridine-3-carboxylic acid 4-methanesulfonyl-benzylamide;

5-(3,5-dimethyl-isoxazol-4-yl)-6-methyl-2-oxo-1-m-tolyl-1,2-dihydro-pyridine-3-carboxylic acid 4-methanesulfonyl-benzylamide;

5-(5-isopropyl-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

6-methyl-5-[1,3,4]oxadiazol-2-yl)-2-oxo-1-(3-trifluoromethylphenyl)-1,2-dihydro-pyridine-3-carboxylic acid 4-methanesulfonyl-benzylamide;

5-(5-hydroxy-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

6-methyl-5-(5-methyl-4H-[1,2,4]triazol-3-yl)-2-oxo-1-(3-trifluoromethylphenyl)-1,2-dihydro-pyridine-3-carboxylic acid 4-methylsulfonyl-benzylamide;

5-(4,5-dimethyl-4H-[1,2,4]triazol-3-yl)-6-methyl-2-oxo-1-(3-trifluoromethylphenyl)-1,2-dihydro-pyridine-3-carboxylic acid 4-methanesulfonyl-benzylamide;

5-(5-methoxymethyl-[1,3,4]oxadiazol-2-yl)-6-methyl-2-oxo-1-(3-trifluoromethylphenyl)-1,2-dihydro-pyridine-3-carboxylic acid 4-methanesulfonyl-benzylamide;

N-[4-(isopropylsulfonyl)benzyl]-6-methyl-5-(5-methyl-1,3,4-oxadiazol-2-yl)-2-oxo-1-[3-(trifluoromethyl)phenyl]-1,2-dihydropyridine-3-carboxamide;

N-[4-(ethylsulfonyl)benzyl]-6-methyl-5-(5-methyl-1,3,4-oxadiazol-2-yl)-2-oxo-1-[3-(trifluoromethyl)phenyl]-1,2-dihydropyridine-3-carboxamide;

N-[4-(cyclopropylsulfonyl)benzyl]-6-methyl-5-(5-methyl-1,3,4-oxadiazol-2-yl)-2-oxo-1-[3-(trifluoromethyl)phenyl]-1,2-dihydropyridine-3-carboxamide;

6-methyl-5-[1,3,4]oxadiazol-2-yl-2-oxo-1-(3-trifluoromethylphenyl)-1,2-dihydro-pyridine-3-carboxylic acid 4-(propane-2-sulfonyl)-benzylamide;

6-methyl-5-[1,3,4]oxadiazol-2-yl-2-oxo-1-(3-trifluoromethylphenyl)-1,2-dihydro-pyridine-3-carboxylic acid 4-cyclopropanesulfonyl-benzylamide;

6-methyl-5-(2-methyl-1,3-oxazol-4-yl)-N-[4-(methylsulfonyl)benzyl]-2-oxo-1-[3-(trifluoromethyl)phenyl]-1,2-dihydropyridine-3-carboxamide;

6-methyl-N-[4-(methylsulfonyl)benzyl]-5-(1,3-oxazol-4-yl)-2-oxo-1-[3-(trifluoromethyl)phenyl]-1,2-dihydropyridine-3-carboxamide;

5-(2-amino-thiazol-4-yl)-6-methyl-2-oxo-1-(3-trifluoromethylphenyl)-1,2-dihydro-pyridine-3-carboxylic acid 4-methanesulfonyl-benzylamide;

5-(2,5-dimethyl-1,3-oxazol-4-yl)-6-methyl-N-[4-(methylsulfonyl)benzyl]-2-oxo-1-[3-(trifluoromethyl)phenyl]-1,2-dihydropyridine-3-carboxamide;

6-methyl-5-(5-methyl-1,3-oxazol-4-yl)-N-[4-(methylsulfonyl)benzyl]-2-oxo-1-[3-(trifluoromethyl)phenyl]-1,2-dihydropyridine-3-carboxamide;

5-(2-amino-5-methyl-thiazol-4-yl)-6-methyl-2-oxo-1-(3-trifluoromethylphenyl)-1,2-dihydro-pyridine-3-carboxylic acid 4-methanesulfonyl-benzylamide;

5-(2-hydroxymethyl-5-methyl-thiazol-4-yl)-6-methyl-2-oxo-1-(3-trifluoromethylphenyl)-1,2-dihydro-pyridine-3-carboxylic acid 4-methanesulfonyl-benzylamide;

6-methyl-5-(5-methyl-[1,2,4]oxadiazol-3-yl)-2-oxo-1-(3-trifluoromethylphenyl)-1,2-dihydro-pyridine-3-carboxylic acid 4-methanesulfonyl-benzylamide;

6-methyl-5-[1,2,4]oxadiazol-3-yl-2-oxo-1-(3-trifluoromethylphenyl)-1,2-dihydro-pyridine-3-carboxylic acid 4-methanesulfonyl-benzylamide;

6-methyl-2-oxo-5-(1H-tetrazol-5-yl)-1-(3-trifluoromethylphenyl)-1,2-dihydro-pyridine-3-carboxylic acid 4-methanesulfonyl-benzylamide;

6-methyl-5-(4-methyl-oxazol-2-yl)-2-oxo-1-(3-trifluoromethylphenyl)-1,2-dihydro-pyridine-3-carboxylic acid 4-methanesulfonyl-benzylamide;

5-(4,5-dimethyl-oxazol-2-yl)-6-methyl-2-oxo-1-(3-trifluoromethylphenyl)-1,2-dihydro-pyridine-3-carboxylic acid 4-methanesulfonyl-benzylamide;

N-(cyclohexylmethyl)-6-methyl-2-oxo-5-phenyl-1-[3-(trifluoromethyl)phenyl]-1,2-dihydropyridine-3-carboxamide;

6-methyl-N-(2-morpholin-4-ylethyl)-2-oxo-5-phenyl-1-[3-(trifluoromethyl)phenyl]-1,2-dihydropyridine-3-carboxamide;

N-[2-(1H-indol-3-yl)ethyl]-6-methyl-2-oxo-5-phenyl-1-[3-(trifluoromethyl)phenyl]-1,2-dihydropyridine-3-carboxamide;

6-methyl-2-oxo-5-phenyl-N-(1-phenylethyl)-1-[3-(trifluoromethyl)phenyl]-1,2-dihydropyridine-3-carboxamide;

6-methyl-2-oxo-5-phenyl-N-(2-phenylethyl)-1-[3-(trifluoromethyl)phenyl]-1,2-dihydropyridine-3-carboxamide;

N-[(1-ethylpyrrolidin-2-yl)methyl]-6-methyl-2-oxo-5-phenyl-1-[3-(trifluoromethyl)-phenyl]-1,2-dihydropyridine-3-carboxamide;

6-methyl-N-(1-naphthylmethyl)-2-oxo-5-phenyl-1-[3-(trifluoromethyl)phenyl]-1,2-dihydropyridine-3-carboxamide;

N-(1,3-benzodioxol-5-ylmethyl)-6-methyl-2-oxo-5-phenyl-1-[3-(trifluoromethyl)phenyl]-1,2-dihydropyridine-3-carboxamide;

N-(2-chloro-4-fluorobenzyl)-6-methyl-2-oxo-5-phenyl-1-[3-(trifluoromethyl)phenyl]-1,2-dihydropyridine-3-carboxamide;

6-methyl-2-oxo-5-phenyl-N-(2-thienylmethyl)-1-[3-(trifluoromethyl)phenyl]-1,2-dihydropyridine-3-carboxamide;

N-(2-cyclohex-1-en-1-ylethyl)-6-methyl-2-oxo-5-phenyl-1-[3-(trifluoromethyl)phenyl]-1,2-dihydropyridine-3-carboxamide;

6-methyl-2-oxo-N-(4-phenoxybenzyl)-5-phenyl-1-[3-(trifluoromethyl)phenyl]-1,2-dihydropyridine-3-carboxamide;

N-[(2,5-dimethyl-3-furyl)methyl]-6-methyl-2-oxo-5-phenyl-1-[3-(trifluoromethyl)-phenyl]-1,2-dihydropyridine-3-carboxamide;

N-{2-[4-(aminosulfonyl)phenyl]ethyl}-6-methyl-2-oxo-5-phenyl-1-[3-(trifluoromethyl)-phenyl]-1,2-dihydropyridine-3-carboxamide;

6-methyl-2-oxo-5-phenyl-N-[4-(1H-pyrazol-1-yl)benzyl]-1-[3-(trifluoromethyl)phenyl]-1,2-dihydropyridine-3-carboxamide;

6-methyl-2-oxo-N-phenoxy-5-phenyl-1-[3-(trifluoromethyl)phenyl]-1,2-dihydro-pyridine-3-carboxamide;

N-[(6-fluoro-4H-1,3-benzodioxin-8-yl)methyl]-6-methyl-2-oxo-5-phenyl-1-[3-(trifluoromethyl)phenyl]-1,2-dihydropyridine-3-carboxamide;

6-methyl-2-oxo-5-phenyl-N-[2-(tetrahydro-2H-pyran-4-yl)ethyl]-1-[3-(trifluoromethyl)-phenyl]-1,2-dihydropyridine-3-carboxamide;

6-methyl-2-oxo-5-phenyl-N-[3-(1H-pyrazol-1-yl)propyl]-1-[3-(trifluoromethyl)phenyl]-1,2-dihydropyridine-3-carboxamide;

6-methyl-N-[(1-methyl-1H-pyrazol-4-yl)methyl]-2-oxo-5-phenyl-1-[3-(trifluoromethyl)-phenyl]-1,2-dihydropyridine-3-carboxamide;

6-methyl-2-oxo-5-phenyl-N-[(1-phenyl-1H-pyrazol-4-yl)methyl]-1-[3-(trifluoromethyl)-phenyl]-1,2-dihydropyridine-3-carboxamide;

N-[(5-methoxy-4-oxo-4H-pyran-2-yl)methyl]-6-methyl-2-oxo-5-phenyl-1-[3-(trifluoromethyl)phenyl]-1,2-dihydropyridine-3-carboxamide;

N-(3-azepan-1-ylpropyl)-6-methyl-2-oxo-5-phenyl-1-[3-(trifluoromethyl)phenyl]-1,2-dihydropyridine-3-carboxamide;

N-(4-cyanobenzyl)-6-methyl-2-oxo-5-phenyl-1-[3-(trifluoromethyl)phenyl]-1,2-dihydropyridine-3-carboxamide;

6-methyl-2-oxo-N-[3-(5-oxo-4,5-dihydro-1H-pyrazol-4-yl)propyl]-5-phenyl-1-[3-(trifluoromethyl)phenyl]-1,2-dihydropyridine-3-carboxamide;

6-methyl-5-(2-methyl-2H-pyrazol-3-yl)-2-oxo-1-(3-trifluoromethylphenyl)-1,2-dihydro-pyridine-3-carboxylic acid (3-methyl-isoxazol-5-ylmethyl)-amide;

6-methyl-5-(2-methyl-2H-pyrazol-3-yl)-2-oxo-1-(3-trifluoromethylphenyl)-1,2-dihydro-pyridine-3-carboxylic acid (5-methanesulfonylmethyl-[1,2,4]oxadiazol-3-ylmethyl)-amide;

6-methyl-5-(2-methyl-2H-pyrazol-3-yl)-2-oxo-1-(3-trifluoromethylphenyl)-1,2-dihydro-pyridine-3-carboxylic acid ([1,2,4]oxadiazol-3-ylmethyl)-amide;

6-methyl-5-(1-methyl-1H-pyrazol-5-yl)-N-{[5-(methylsulfonyl)pyridin-2-yl]methyl}-2-oxo-1-[3-(trifluoromethyl)phenyl]-1,2-dihydropyridine-3-carboxamide;

5-(3,5-dimethylisoxazol-4-yl)-6-methyl-N-{[5-(methylsulfonyl)pyridin-2-yl]methyl}-2-oxo-1-[3-(trifluoromethyl)phenyl]-1,2-dihydropyridine-3-carboxamide;

or a pharmaceutically acceptable salt thereof.

6. A compound of formula (I) as defined in claim 1, which is 5-(3,5-dimethyl-isoxazol-4-yl)-6-methyl-2-oxo-1-(3-trifluoromethyl-phenyl)-1,2-dihydro-pyridine-3-carboxylic acid 4-methanesulfonyl-benzylamide, or a pharmaceutically acceptable salt thereof.

7. A pharmaceutical formulation comprising a compound of formula (I), as defined in claim 1, or a pharmaceutically acceptable salt thereof, optionally in admixture with a pharmaceutically acceptable diluent or carrier.

8. A process for the preparation of a compound of formula (I), as defined in claim 1, or tautomer thereof or a pharmaceutically acceptable salt thereof, which comprises:

a) reacting a compound of formula (II)

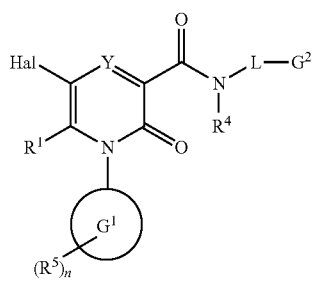

(II)

wherein $R^1$, $R^4$, $R^5$, Y, $G^1$, $G^2$, L and n are as defined in formula (I) and Hal represents a halogen atom;

with a nucleophile $R^2$-M wherein $R^2$ is as defined in formula (I) and M represents an organo-tin or organo boronic acid group; or b) when $R^2$ represents a 1,3,4-oxadiazol-2-yl or a 1,3,4-thiadiazol-2-yl ring, reacting a compound of formula (III)

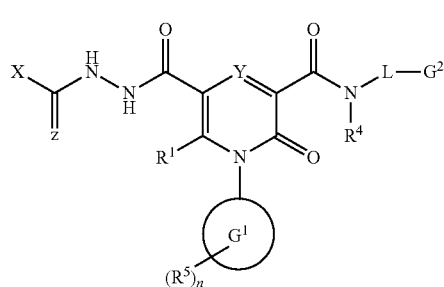

(III)

wherein $R^1$, $R^4$, $R^5$, Y, $G^1$, $G^2$, L and n are as defined in formula (I), Z represents O or S and X represents C1 to 6 alkyl or $NR^{47}R^{48}$ and $R^{47}$ and $R^{48}$ are as defined in formula (I);

with a suitable dehydrating agent; or c) reacting a compound of formula (XV)

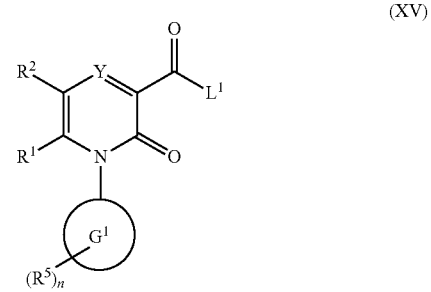

(XV)

wherein $R^1$, $R^2$, $R^5$, n, $G^1$ and Y are as defined in formula (I) and $L^1$ represents a leaving group, with a compound of formula (IX) or a salt thereof

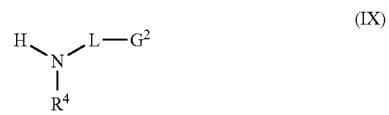

(IX)

wherein $R^4$, $G^2$ and L are as defined in formula (I);

and where desired or necessary converting the resultant compound of formula (I), or another salt thereof, into a pharmaceutically acceptable salt thereof; or converting one compound of formula (I) into another compound of formula (I); and where desired converting the resultant compound of formula (I) into an optical isomer thereof.

9. A process according to claim 8, wherein Hal represents Br or I, and the dehydrating agents is phosphoryl chloride or trimethylsilyl polyphosphate.

* * * * *